(12) United States Patent
Martin et al.

(10) Patent No.: US 10,537,322 B2
(45) Date of Patent: Jan. 21, 2020

(54) SURGICAL SUTURING INSTRUMENT CARTRIDGE WITH NEEDLE RELEASE FEATURE

(71) Applicant: ETHICON LLC, Guaynabo, PR (US)

(72) Inventors: David T. Martin, Milford, OH (US); Daniel J. Mumaw, Liberty Township, OH (US); William J. White, West Chester, OH (US); Andrew C. Deck, Dayton, OH (US); James G. Lee, Cincinnati, OH (US); Michael D. Cronin, Cincinnati, OH (US); Alexandra Monnin, Cincinnati, OH (US); J. Bernar Ogzewalla, Maysville, KY (US); Daniel L. Geiger, Ft. Thomas, KY (US)

(73) Assignee: Ethicon LLC, Guaynabo, PR (US)

( * ) Notice: Subject to any disclaimer, the term of this patent is extended or adjusted under 35 U.S.C. 154(b) by 42 days.

(21) Appl. No.: 15/407,905

(22) Filed: Jan. 17, 2017

(65) Prior Publication Data

US 2018/0199934 A1 Jul. 19, 2018

(51) Int. Cl.
| | | |
|---|---|---|
| *A61B 17/04* | (2006.01) | |
| *A61B 17/062* | (2006.01) | |
| *A61B 17/06* | (2006.01) | |
| *A61B 17/00* | (2006.01) | |
| *A61B 90/00* | (2016.01) | |

(52) U.S. Cl.
CPC ...... *A61B 17/0625* (2013.01); *A61B 17/0469* (2013.01); *A61B 17/06133* (2013.01); *A61B 2017/00473* (2013.01); *A61B 2017/00477* (2013.01); *A61B 2017/0608* (2013.01); *A61B 2090/034* (2016.02)

(58) Field of Classification Search
CPC .......... A61B 17/0491; A61B 17/06133; A61B 17/0469; A61B 17/0625; A61B 2017/00477; A61B 2017/06142
See application file for complete search history.

(56) References Cited

U.S. PATENT DOCUMENTS

| | | |
|---|---|---|
| 8,702,732 B2 | 4/2014 | Woodard et al. |
| 9,168,037 B2 | 10/2015 | Woodard et al. |
| 9,357,998 B2 | 6/2016 | Martin et al. |
| 9,375,212 B2 | 6/2016 | White et al. |

(Continued)

*Primary Examiner* — Eric J Rosen
*Assistant Examiner* — Andrew P. Restaino
(74) *Attorney, Agent, or Firm* — Frost Brown Todd LLC

(57) ABSTRACT

A surgical instrument includes a body, a shaft, a cartridge receiving assembly, a suture cartridge, and a cage securement. The suture cartridge is configured to be received within the cartridge receiving assembly and has a cartridge body, a needle, a drive assembly, and a cage. The cage is movably secured to the cartridge body to selectively move relative to the cartridge body from a closed position to an opened position. In the closed position, the cage is configured to contain the needle within the cartridge body. In the opened position, the cage is configured such that the needle is removable from the cartridge body. The cage securement is configured to move from a first position to a second position to inhibit movement of the cage from the closed position toward the opened position, yet release movement of the cage for selectively moving the cage to the opened position.

19 Claims, 48 Drawing Sheets

(56) References Cited

U.S. PATENT DOCUMENTS

| | | | |
|---|---|---|---|
| 9,474,522 B2 | 10/2016 | Deck et al. | |
| 2002/0193809 A1* | 12/2002 | Meade | A61B 17/0469 606/144 |
| 2004/0133216 A1* | 7/2004 | Wulc | A61B 17/0482 606/144 |
| 2013/0153634 A1* | 6/2013 | Carter | A61B 17/072 227/176.1 |
| 2015/0351756 A1* | 12/2015 | Martin | A61B 17/0469 606/144 |
| 2016/0367243 A1* | 12/2016 | Martin | A61B 17/0469 |

\* cited by examiner

SURGICAL SUTURING INSTRUMENT CARTRIDGE WITH NEEDLE RELEASE FEATURE

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, issued as U.S. Pat. No. 9,168,037 on Oct. 27, 2015, the disclosure of which is incorporated by reference herein; U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; and U.S. Pat. No. 9,474,522, entitled "Jawed Receiver for Needle Cartridge," issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
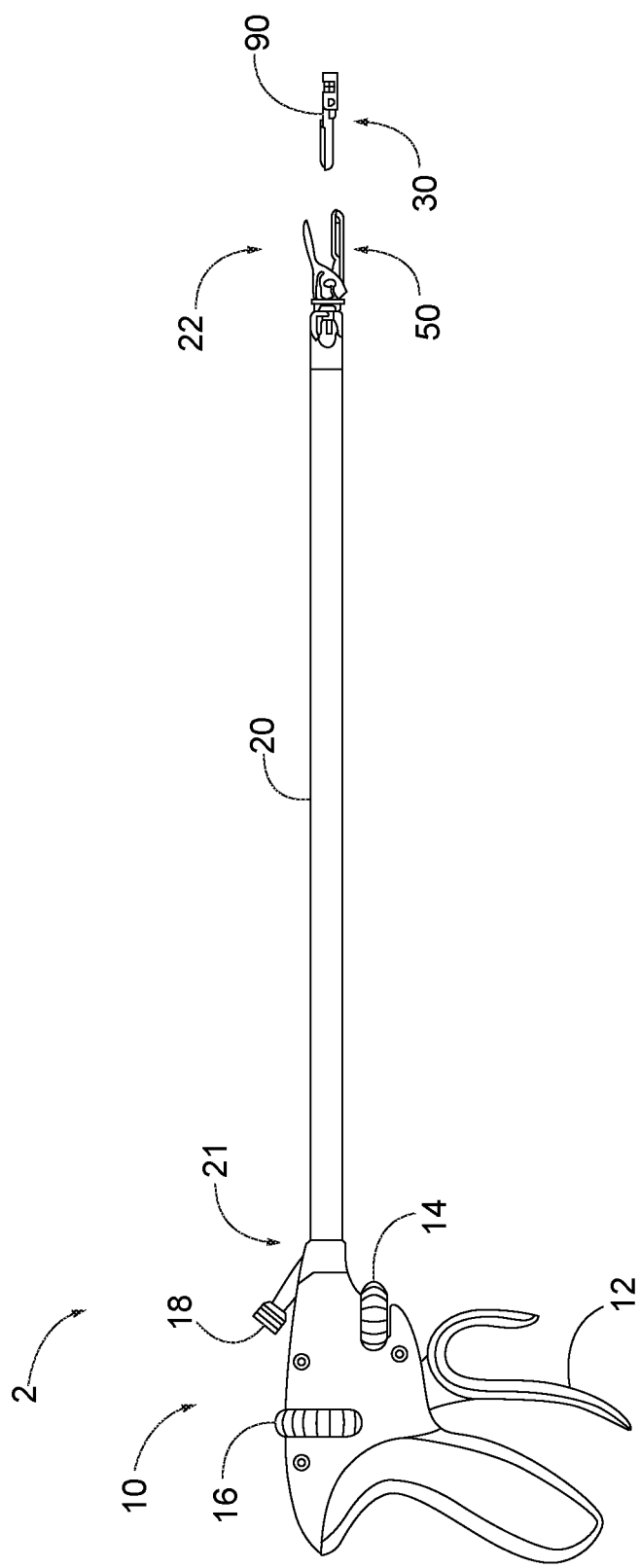
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", and "lower" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The term "upper" refers to the position of the element closer to a top of the surgical instrument when viewed by the operator from above, and the term "lower" refers to the position of the element closer to a bottom of the surgical instrument when viewed by the operator from below. As such, proximal and distal portions are generally in longitudinal opposition as described herein, whereas upper and lower portions are generally in transverse opposition as described herein. In addition, the terms "clockwise," "counterclockwise," "left," and "right" are used below with reference to views as illustrated for clarity and are not intended to limit the invention described herein.

I. Overview of Exemplary Surgical Suturing Instrument

FIG. 1 illustrates an example of a surgical suturing instrument (2). Instrument (2) comprises a handle assembly (10) and a shaft assembly (19) having an elongate shaft (20) extending from a distal end portion (21) to a proximal end portion (22) thereof. Distal end portion (21) includes a cartridge receiving assembly (50), which is operable to receive a needle applier cartridge (30). Shaft (20) defines a longitudinal axis extending from proximal end portion (22) to distal end portion (21). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger that pivots between opened and closed positions, may be used to selectively actuate needle applier cartridge (30). The trigger may be spring biased to return the trigger to its opened position. A second user input member (14), shown here as a rotary knob, may be used to selectively articulate shaft (20). A third user input member (16), shown here as a rotary knob, may be used to selectively rotate needle applier cartridge (30) about shaft (20). Of course, the number, type, configuration, and operation of input members (12, 14, 16) may vary.

Shaft (20) includes an articulation joint (23). Rotary knob (14) is operable to selectively articulate joint (23) via a joint drive assembly (118). Rotary knob (14) rotates in a plane spaced below and generally parallel with shaft (20). An axle (121) connects rotary knob (14) to a disk (not shown) in housing (11) that also rotates in a plane generally parallel with the shaft (20) for position distal end portion (21) of shaft assembly (19) relative to proximal end portion (22).

Figure 2A:
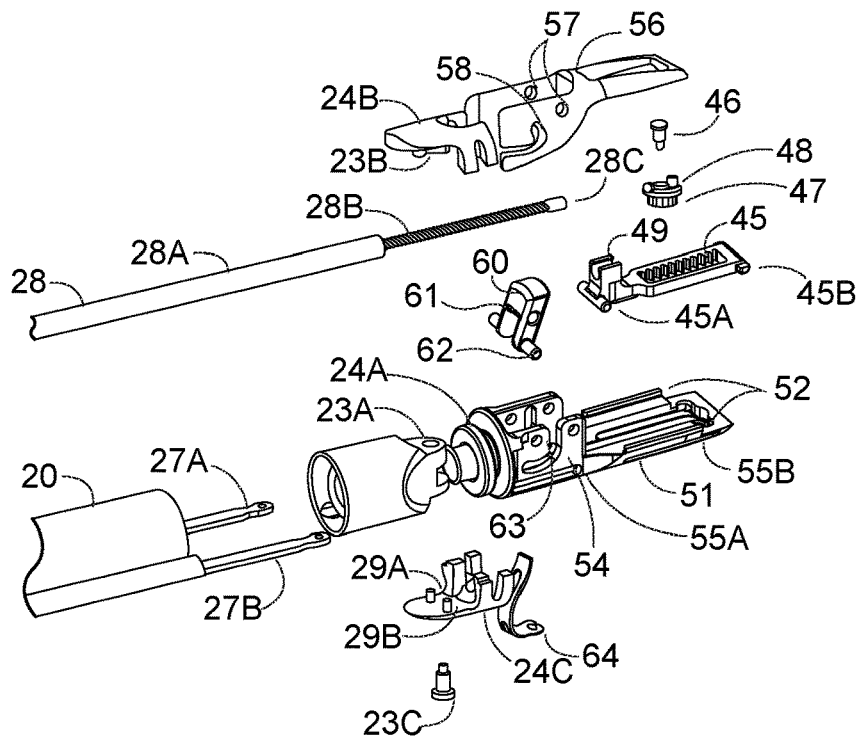
FIG. 2A depicts top perspective exploded view of a cartridge receiving assembly of the instrument of FIG. 1.
Figure 2B:
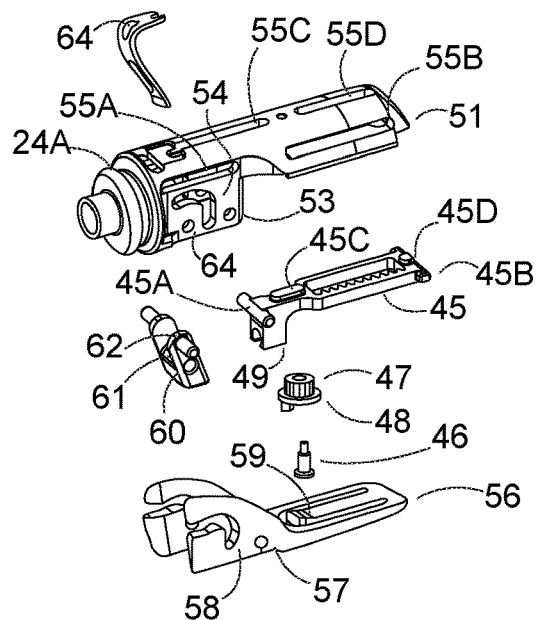
FIG. 2B depicts bottom perspective exploded view of the cartridge receiving assembly of FIG. 2A.

FIGS. 2A-2B illustrate exploded views of cartridge receiving assembly (50) of the present example. Distal end portion (22) of shaft (20) comprises articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Cartridge receiving assembly (50) includes a transmission mechanism (44) configured to transfer force from input trigger (12) to cartridge (30) for actuation thereof. Transmission mechanism (44) includes rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by a pin (46) in the rack (45) such that longitudinal reciprocation of the rack (45) is converted into rotational reciprocation of pinion (47). A key (48) of transmission mechanism (44) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3:
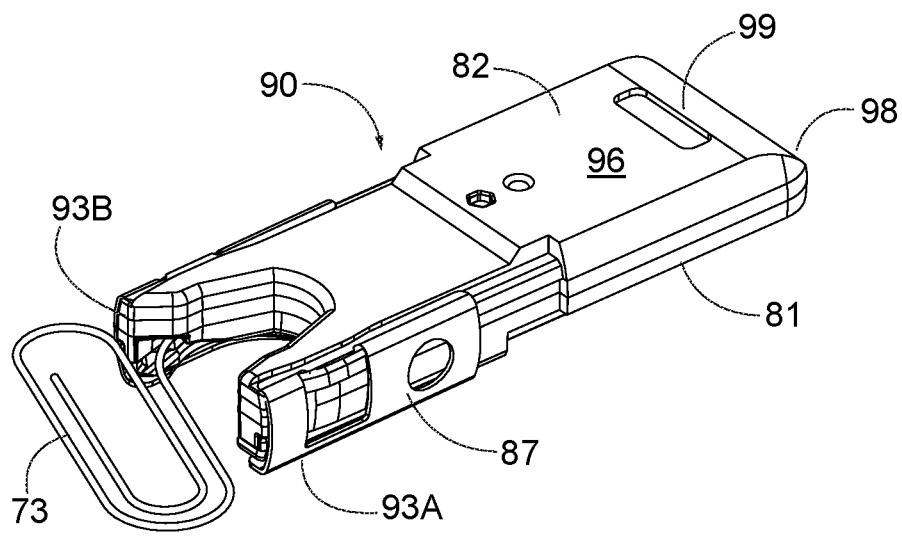
FIG. 3 depicts a top perspective view of an exemplary cartridge configured for receipt in the cartridge receiving assembly of FIG. 2A.
Figure 4:
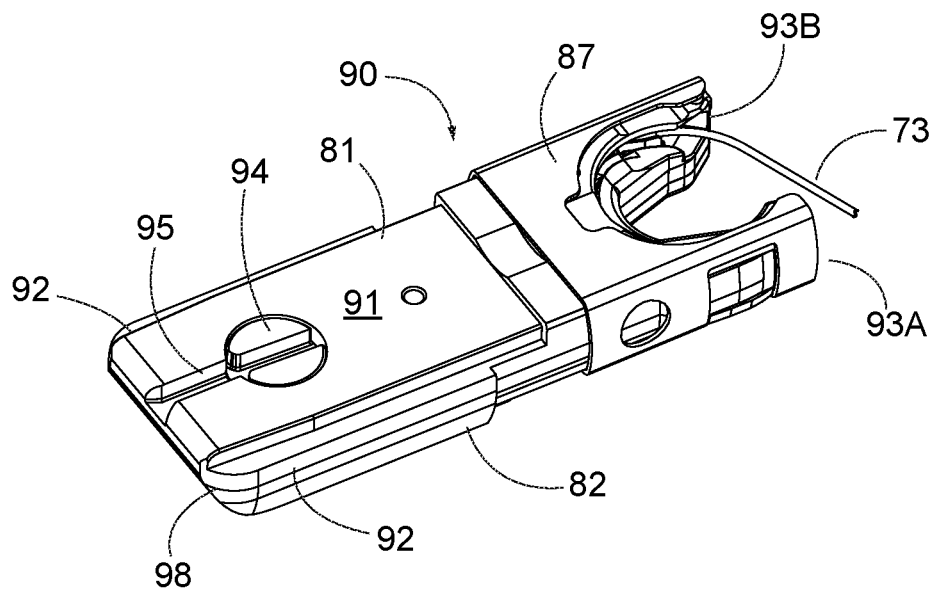
FIG. 4 depicts a bottom perspective view of the cartridge of FIG. 3.

FIGS. 3-4 illustrate cartridge body (90) of the present example in greater detail. A lower face (91) of cartridge body (90) is adapted to engage lower jaw (51); and an upper face (96) is adapted to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 5:
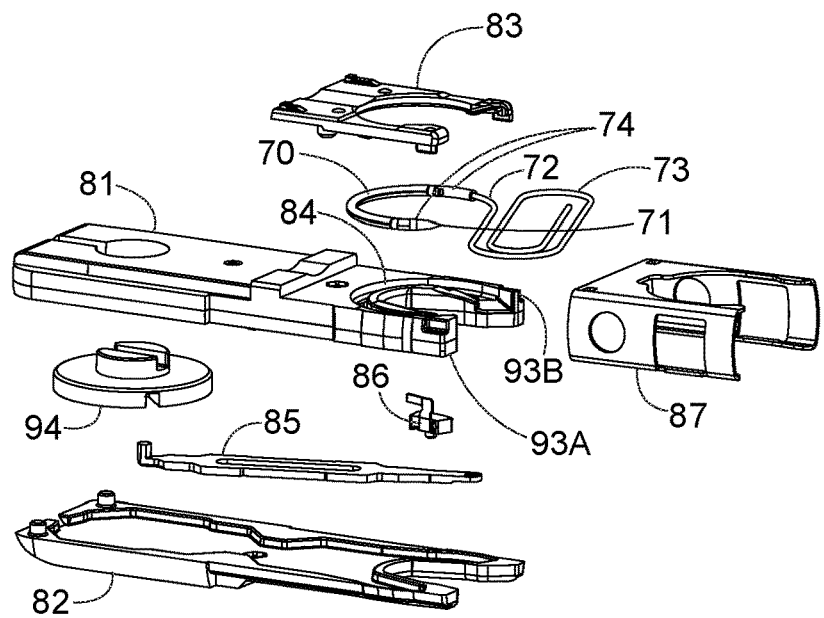
FIG. 5 depicts an exploded view of the cartridge of FIG. 3.

As shown in FIGS. 3-5, cartridge body (90) further comprises a lower body (81), an upper body (82), a needle (70), a needle cover (83) and a drive assembly (80) configured to drive needle (70). Drive assembly (80) includes a needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from a trailing end (72) thereof. Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 6A:
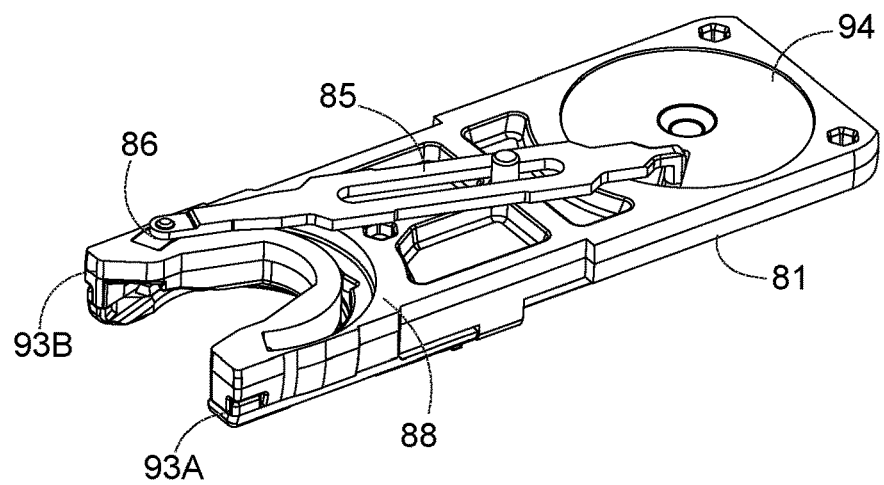
FIG. 6A depicts a perspective view of a drive assembly of the cartridge of FIG. 3, with the drive assembly at one end of its stroke.
Figure 6B:
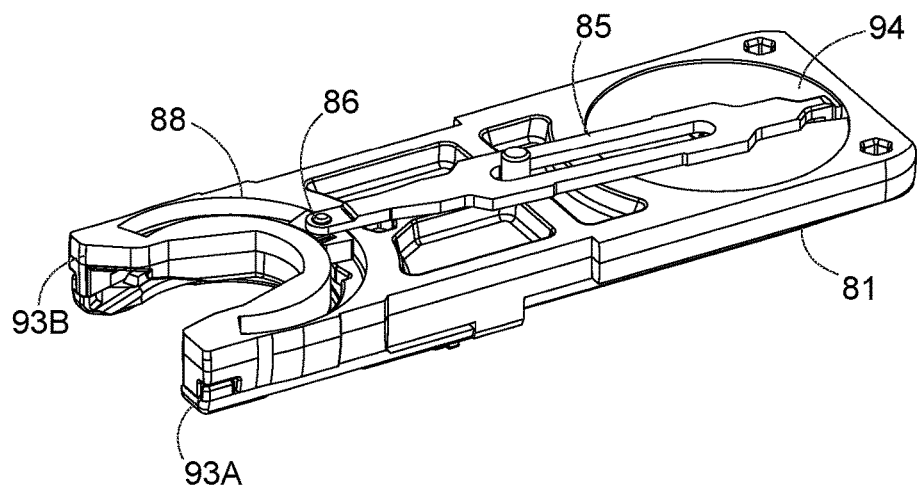
FIG. 6B depicts a perspective view of the drive assembly of FIG. 6A, with the drive assembly at mid-stroke.
Figure 6C:
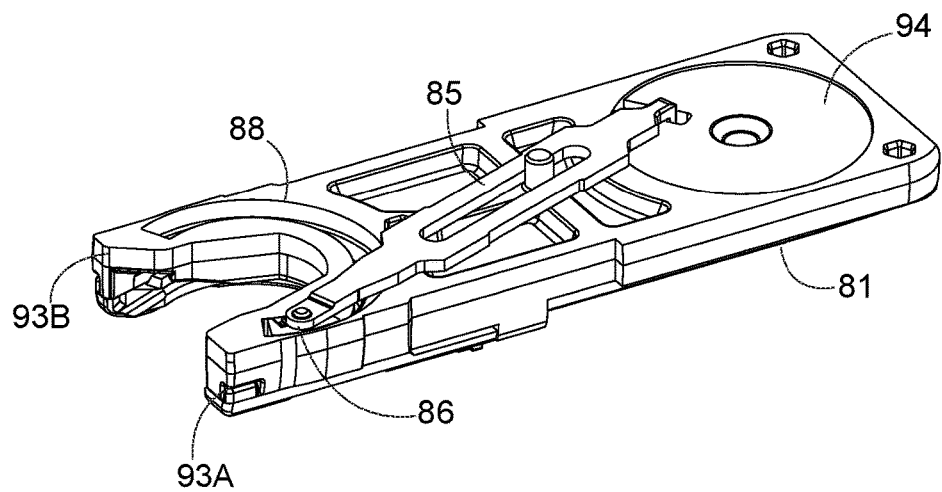
FIG. 6C depicts a perspective view of the drive assembly of FIG. 6A, with the drive assembly at the other end of its stroke.

FIGS. 6A-6C illustrate an example of a drive stroke of the transmission in cartridge body (90) for driving needle (70) in a circular, orbital path. However, it should be understood that needle (70) and suture (73) are omitted from FIGS. 6B-6C for clarity. Needle driver (86) rides in a carrier track (88) and extends into needle track (84) (see FIG. 5) to engage and drive needle (70). Link (85) connects rotary input (94) to needle driver (86). FIG. 6A shows needle driver (86) positioned at one end of its stroke in carrier track (88). As shown in FIG. 6B, counterclockwise rotation of rotary input (94) will translate needle driver (86) clockwise along carrier track (88), thereby driving needle (70) clockwise. As shown in FIG. 6C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 7:
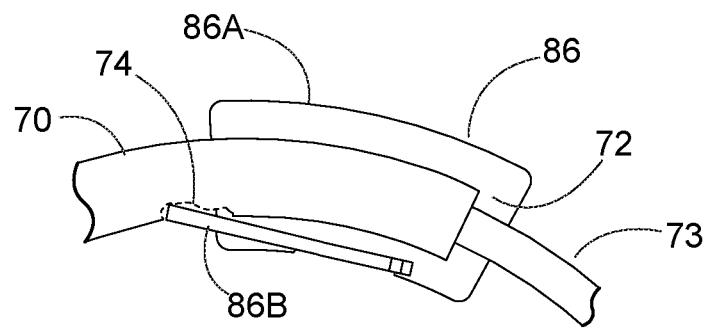
FIG. 7 depicts a partial plan view of a needle driver of the cartridge of FIG. 3 engaging a needle of the cartridge of FIG. 3.

FIG. 7 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (86A) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 6A-6C and FIG. 7, when first user input member (12) (see FIG. 1) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (97A) and entrance port (97B). Tissue interposed between arms (93A, 93B) will be pierced by leading end (71) of needle (70).

When first user input member (12) (see FIG. 1) is released and the spring return opens the trigger, needle driver (86) reciprocates through its return stroke where it orbits along an angular range of motion about 180 degrees clockwise back to the return position shown in FIG. 6A. During the return stroke, driver (86B) slides over the needle (70). Driver (86B) is then adjacent the distal notch (74). When first user input member (12) is depressed again closing the trigger, needle driver (86) will again be actuated through its drive stroke where it orbits along an angular range of motion about 180 degrees counterclockwise to the driven position as shown in FIG. 6C. During the drive stroke, driver (86B) engages distal notch (74) and will in unison drive needle (70) orbitally along an angular range of motion about 180 degrees back to its retracted position. Suture (73) (see FIG. 3) will follow needle (70) and be threaded through the pierced tissue.

When first user input member (12) (see FIG. 1) is again released and the spring return opens the trigger, needle driver (86) again reciprocates through its return stroke where it orbits along an angular range of motion about 180 degrees clockwise back to its returned position as shown in FIG. 6A. During the return stroke, driver (86B) slides over needle (70). Thus, needle (70) is driven in a complete circular path spanning an angular range of 360° in response to first user input member (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; U.S. Pat. No. 9,474,522, entitled "Jawed Cartridge Receiving Assembly for Needle Cartridge," issued Oct. 25, 2016, the disclosure of which is incorporated by reference herein; U.S. Pat. No. 9,375,212, entitled "Circular Needle Applier with Cleats," issued Jun. 28, 2016, the disclosure of which is incorporated by reference herein; and U.S. patent application Ser. No. 14/740,724, entitled "Suturing Instrument with Motorized Needle Drive," filed Jun. 16, 2015, issued as U.S. Pat. No. 9,888,914 on Feb. 13, 2018, the disclosure of which is incorporated by reference herein. It should be understood that such details, explanations, examples, and alternative embodiments may be readily applied to the above-described instrument (10) and subcomponents thereof.

II. Exemplary Cartridge Receiving Assembly and Needle Release Feature

In some instances, it may be desirable to remove needle (70) from cartridge body (90) during a suturing procedure within a patient. For example, needle (70) may become difficult to move, or even jam entirely, within cartridge body (90), with adjacent tissue and/or adjacent surgical equipment unintentionally captured therein. Attempting to force needle (70) through such tissue or a relatively hard object may greatly increase the force required to displace needle (70) and, in turn, increase the forces being transmitted through surgical instrument (2). Such forces may increase the likelihood that needle (70), cartridge (30), or another portion of surgical instrument (2) may be damaged during use. The operator may then need to replace cartridge (30), repair surgical instrument (2) or, in the event that the damage to surgical instrument (2) is beyond repair, replace surgical instrument (2) with a new, undamaged surgical instrument (2). Moreover, the increased driving force of needle (70) may also result in damage to surrounding tissue or adjacent surgical equipment.

Damage to surgical equipment and/or tissue may be costly and time consuming to correct, particularly in a fast paced and complex surgical procedure. In some instances, surgical instrument (2), or more particularly cartridge (30), may thus be configured such that needle (70) may be efficiently removed during the surgical procedure and either repaired or replaced for continuing the remainder of the surgical procedure. It may be desirable to provide a cartridge receiving assembly (102), which operates substantially similar to cartridge receiving assembly (50), but has an elongate slot (104) distal of a pair of longitudinal rails (106), such as cartridge receiving assembly (102) shown in FIG. 8. Elongate slot (104) is configured to provide proximal clearance for a cage (87) of cartridge (30) discussed below with respect to FIGS. 8-71B to selectively move proximally from a closed position, which contains needle (70) within cartridge body (90), to an opened position, which allows removal of needle (70) during the surgical procedure.

While elongate slot (104) provides ample clearance for proximal movement of cage (87) to access needle cover (83) for removal of needle (70), a cage securement (206, 306, 406, 506, 606, 706, 806, 906, 1006, 1006a, 1106, 1206, 1306, 1406, 1406a, 1506, 1506a, 1606, 1706, 1806, 1906, 2006, 2106, 2206, 2306, 2306a, 2406, 2506, 2606, 2706, 2806, 2906, 3006, 3106, 3206, 3206a, 3206b, 3306, 3406) is further provided to inhibit inadvertent proximal movement of cage (87) due to a variety of forces that cage (87) may encounter during normal use, such as a proximal force while being introduced into the patient. Cage securement (206, 306, 406, 506, 606, 706, 806, 906, 1006, 1006a, 1106, 1206, 1306, 1406, 1406a, 1506, 1506a, 1606, 1706, 1806, 1906, 2006, 2106, 2206, 2306, 2306a, 2406, 2506, 2606, 2706, 2806, 2906, 3006, 3106, 3206, 3206a, 3206b 3306, 3406) is configured to inhibit proximal movement of cage (87) from the closed position to the opened position for repairing or replacing needle (70).

Various examples of cage securements (206, 306, 406, 506, 606, 706, 806, 906, 1006, 1006a, 1106, 1206, 1306, 1406, 1406a, 1506, 1506a, 1606, 1706, 1806, 1906, 2006, 2106, 2206, 2306, 2306a, 2406, 2506, 2606, 2706, 2806, 2906, 3006, 3106, 3206, 3206a, 3206b, 3306, 3406) will be described in greater detail below; while other examples, such as those having various combinations of features described herein, will be apparent to those of ordinary skill in the art according to the teachings herein. It should be understood that instruments (2) incorporating the examples described below may function substantially similar to instrument (2) described above. In particular, the surgical suturing instruments, cartridge receiving assemblies, and cartridges described below may be used to suture tissue as described above. To this end, like numbers referenced below indicate like features discussed herein in greater detail.

A. Chamfered Tab Cage Securement

Figure 8:
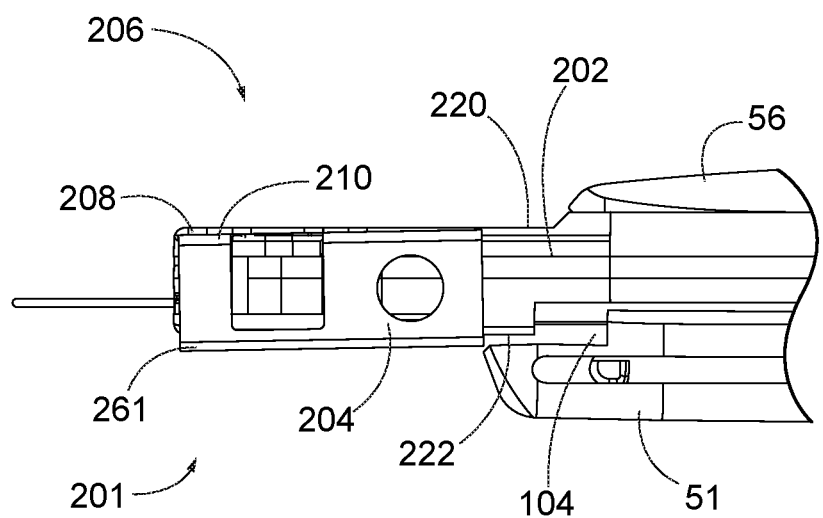
FIG. 8 depicts an enlarged side view of another exemplary cartridge positioned in the cartridge receiving assembly of FIG. 2A, with an exemplary chamfered tab cage securement.
Figure 9:
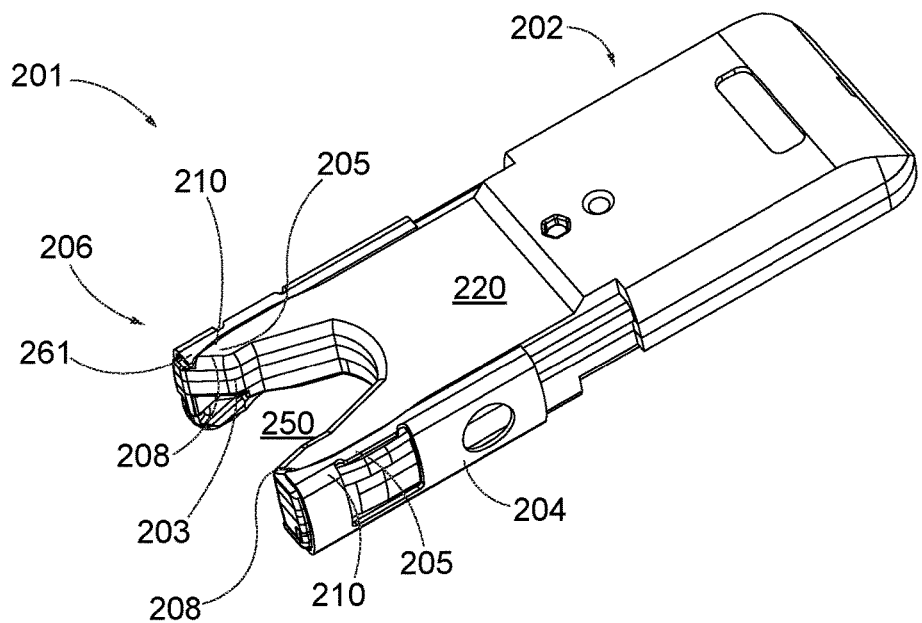
FIG. 9 depicts a top perspective view of the cartridge and chamfered tab cage securement of FIG. 8.
Figure 10A:
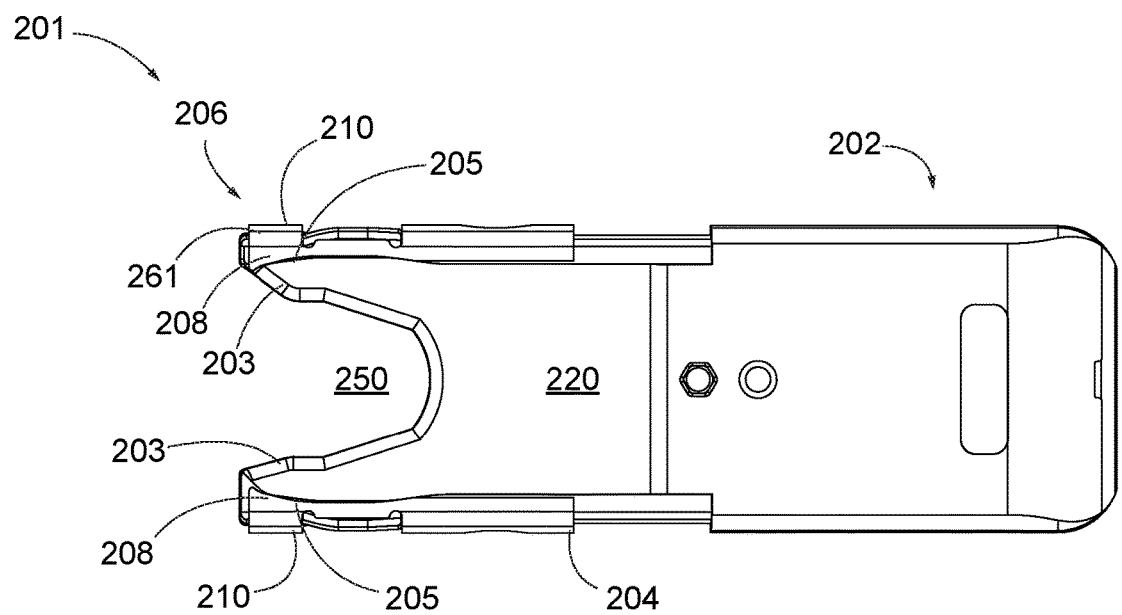
FIG. 10A depicts a top view of the cartridge and the chamfered tab cage securement of FIG. 8, with the cage in a closed position.
Figure 10B:
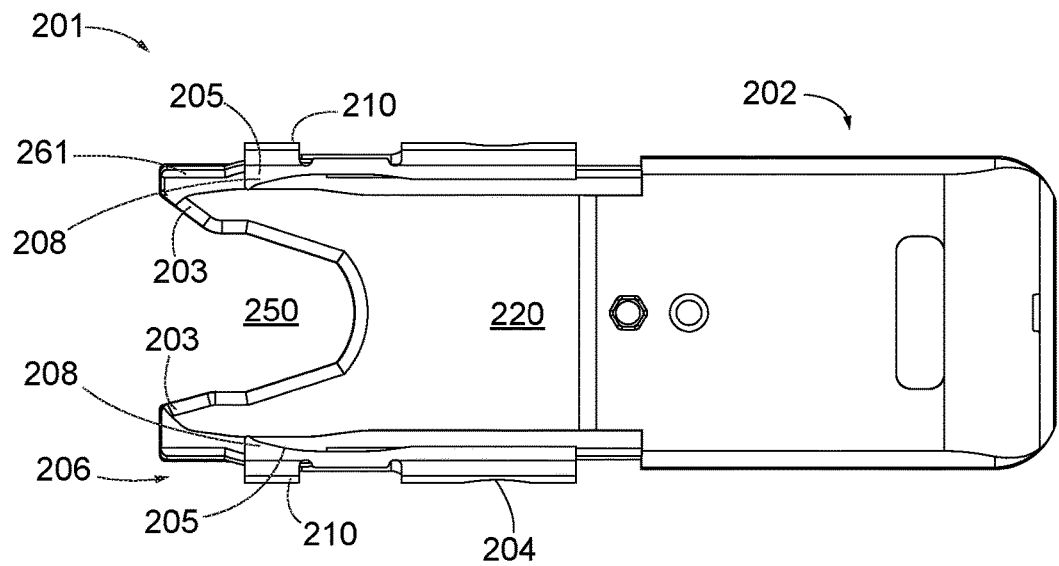
FIG. 10B depicts a top view of the cartridge and the chamfered tab cage securement of FIG. 8, with the cage in an opened position.

FIGS. 8-9 illustrate a cartridge (201) with an exemplary chamfered tab cage securement (206). It should be understood that cartridge (201) of this example may be configured and operable just like cartridge (30) described above, except for the differences explicitly noted herein. Chamfered tab cage securement (206) comprises a tab abutment (208) projecting from a distal end portion (261) of a cage (204) and extending inwardly toward a cavity (250). Chamfered tab cage securement (206) of cage (204) is sized and shaped to associate tab abutment (208) with a distal end portion of a cartridge body (202) to provide resistance of cage (204) against cartridge body (202) and inhibit movement of cage (204) from a closed position to an opened position within elongate slot (104). Elongate slot (104) of cartridge receiving assembly (102) is sized and configured to provide clearance for the proximal movement of cage (204). As depicted in FIGS. 10A-10B, upon exertion by an operator of a predetermined opening force greater than that amount of resistance generated by chamfered tab cage securement (206), tab abutment (208) of chamfered tab cage securement (206) deflects outwardly at a deflector (210) of cage (204) and allows cage (204) to slidably translate away from the closed position and toward the opened position into an elongate slot (104).

In the present example, tab abutment (208) of chamfered tab cage securement (206) is chamfered along sidewalls (205) at distal end portion (261) of cage (204) and shaped in proportional correspondence to a respective pair of tapered ends (203) along an upper surface (220) of cartridge body (202). As shown in the present example, chamfered tab cage securement (206) includes tab abutment (208) on each side of cage (204). Deflector (210) comprises a portion of cage (204) integrally attached to tab abutment (208) in that tab abutment (208) and deflector (210) of chamfered tab cage securement (206) are integrally and unitarily formed. Although tab abutment (208) and deflector (210) of the present example are shown as being integrally and unitarily formed, it should be understood that in other examples each may comprise separately formed features of varying sizes, shapes, and/or lengths. In the present example, cage (204) is configured to resiliently bias tab abutment (208) inwardly to engage tapered ends (203) and thereby substantially retain cage (204) in the closed position. Upon exertion by the operator of the predetermined opening force to overcome the resilient bias, tab abutments (208) deflect laterally and outwardly at deflectors (210) and allow cage (204) to slidably translate proximally from the closed position and toward the opened position through elongate slot (104). Positioning cage (204) proximally toward elongate slot (104) allows the operator to access needle cover (83) (see FIG. 5) in order to remove needle (70) (see FIG. 5) from cartridge body (202).

In some instances, it may be desirable to include tab abutment (208) of chamfered tab cage securement (206) on a lower surface (222) (see FIG. 8) of cartridge body (202) to securely fit against tapered end (203) of cartridge body (202). By way of further example, it may be desirable to include chamfered tab cage securement (206) on a proximal end portion (260) of cage (204). As with other components described herein, chamfered tab cage securement (206) may be relocated, varied, modified, substituted, or supplemented in a variety of ways and configurations. Chamfered tab cage securement (206) of cage (204) is made from a material similar to that of cage (204). However, chamfered tab cage securement (206) may be made from various materials that resiliently and/or plastically deflect.

B. Notch Cage Securement

Figure 11:
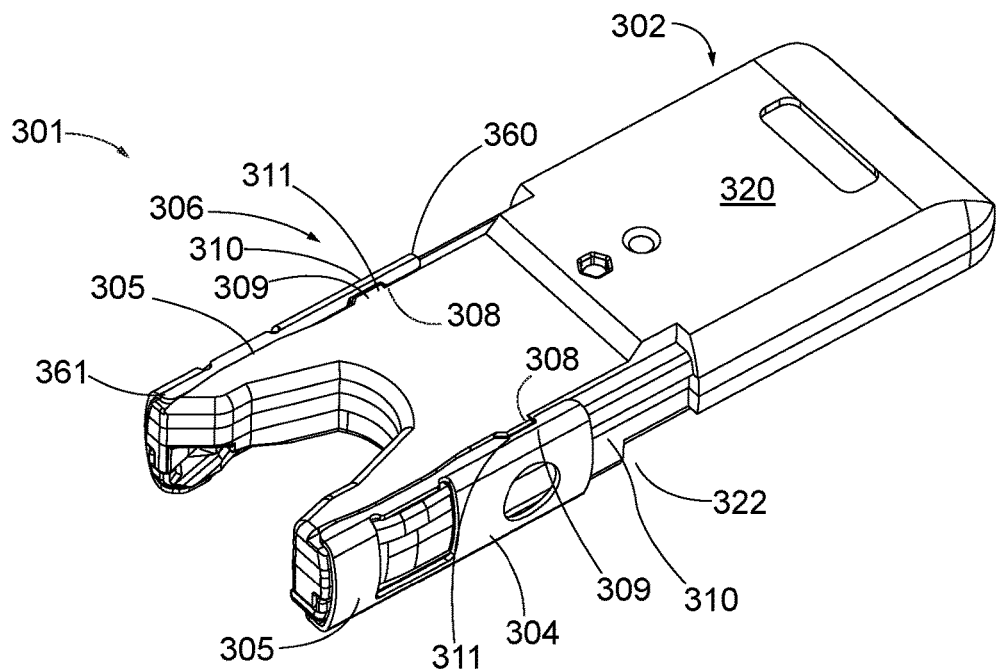
FIG. 11 depicts a top perspective view of another exemplary cartridge configured for receipt in the cartridge receiving assembly of FIG. 2A, with a first exemplary notch cage securement.
Figure 12A:
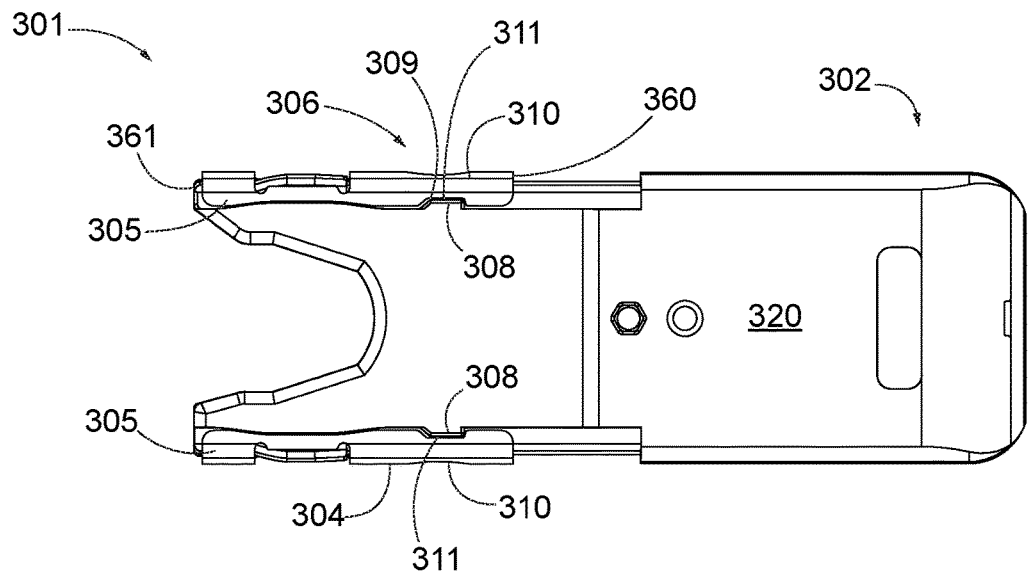
FIG. 12A depicts a top view of the cartridge and the notch cage securement of FIG. 11, with the cage in a closed position.
Figure 12B:
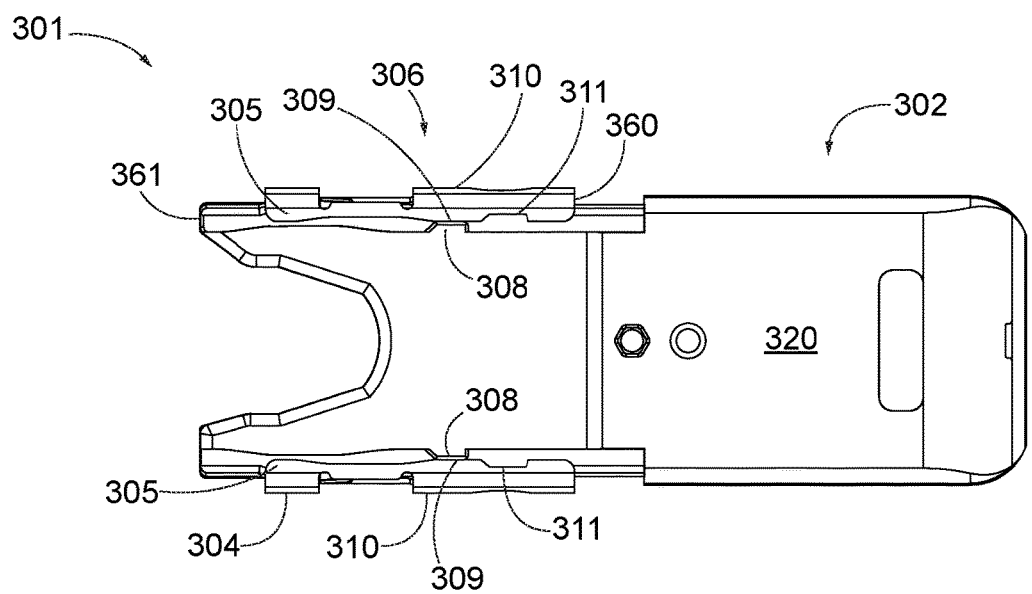
FIG. 12B depicts a top view of the cartridge and the notch cage securement of FIG. 11, with the cage in an opened position.

FIG. 11 shows a cartridge (301) with a first exemplary notch cage securement (306) comprising a notch abutment (308) projecting from a cartridge body (302) and extending laterally and outwardly to be received in a corresponding deflector (310) of a cage (304). It should be understood that cartridge (301) of this example may be configured and operable just like cartridge (30) described above, except for the differences explicitly noted herein. In this example, notch cage securement (306) is positioned at a portion of cage (304) between a distal end portion (361) and a proximal end portion (360). Notch cage securement (306) is sized and shaped to associate notch abutment (308) of cartridge body (302) with deflector (310) along a top portion of sidewalls (305) of cage (304) to provide resistance of cage (304) against cartridge body (302). Notch cage securement (306) thereby inhibits movement of cage (304) from the closed position to the opened position through elongate slot (104) (see FIG. 8). As depicted in FIGS. 12A-12B, upon exertion by the operator of the predetermined opening force greater than that amount of resistance generated by notch cage securement (306), notch abutment (308) causes deflector (310) of cage (304) to deflect laterally and outwardly. Cage (304) is thus configured to slidably translate from the closed position toward the opened position into elongate slot (104).

In the present example, an upper surface (320) of cartridge body (302) includes two notch abutments (308) fixedly attached to corresponding deflectors (310) of cage (304) at a portion of cage (304). More particularly, notch abutments (308) include tapered protrusions (309) sized and shaped to securely fit respectively into a pair of notches (311) on deflectors (310), which are in sidewalls (305) of cage (304). In some other versions, notch abutments (308) are positioned on a lower surface (322) (see FIG. 11) of cartridge body (302) to correspond with the varied location of deflectors (310). By way of further example, it may be desirable to include notch cage securement (306) on a distal end portion (361) of cage (304) to correspond with the varied location of notch abutment (308) of cartridge body (302). As depicted in FIGS. 12A-12B, notch abutments (308) are configured to resiliently engage tapered protrusions (309) and thereby substantially retain cage (304) in the closed position. Upon exertion by the operator of the predetermined opening force to overcome the resilient bias, notch abutments (308) cause deflectors (310) of cage (304) to deflect laterally and outwardly. Notch cage securement (306) thus allows cage (304) to slidably translate from the closed position toward the opened position through elongate slot (104) (see FIG. 8).

Figure 13:
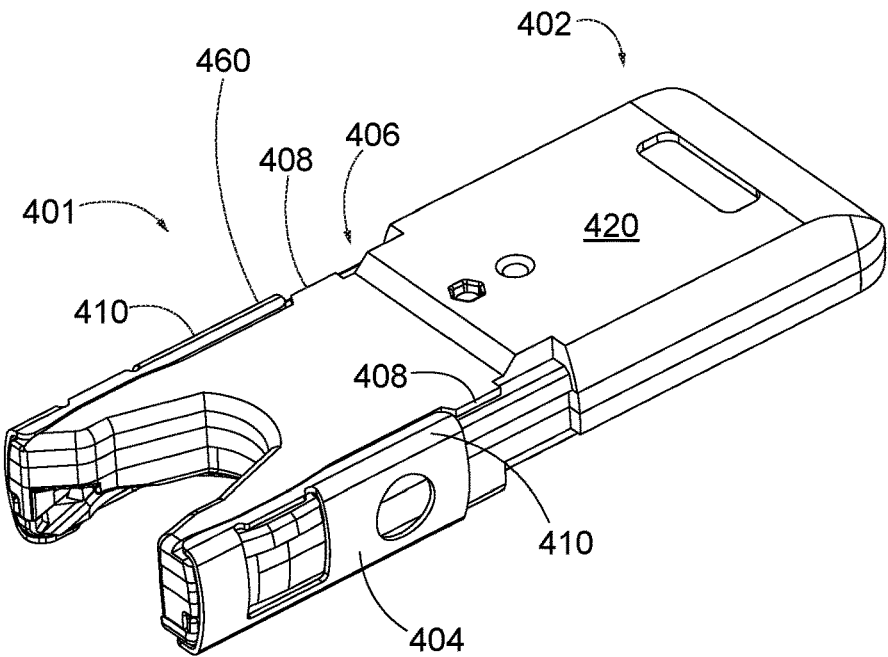
FIG. 13 depicts a top perspective view of another exemplary cartridge configured for receipt in the cartridge receiving assembly of FIG. 2A, with a second exemplary notch cage securement.
Figure 14A:
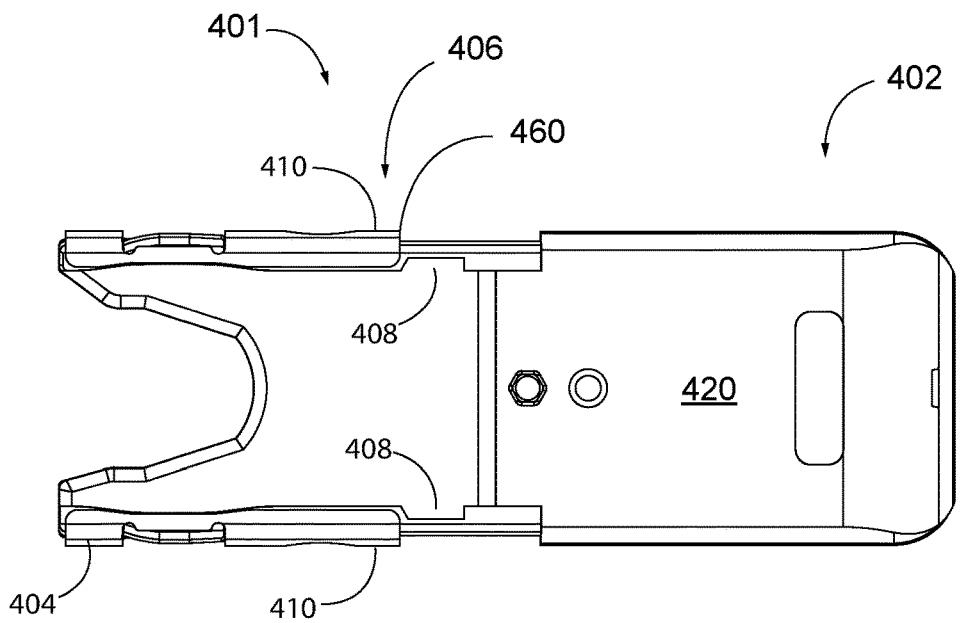
FIG. 14A depicts a top view of the cartridge and the notch cage securement of FIG. 13, with the cage in a closed position.
Figure 14B:
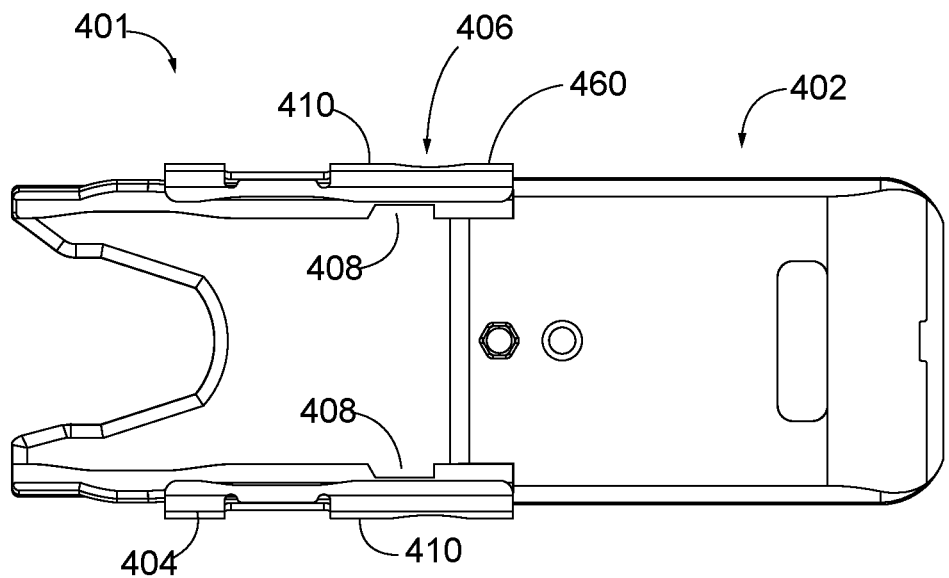
FIG. 14B depicts a top view of the cartridge and the notch cage securement of FIG. 13, with the cage in an opened position.

As shown in FIG. 13, another cartridge (401) has a second exemplary notch cage securement (406) that comprises notch abutments (408) projecting from cartridge body (402) adjacent a proximal end portion (460) of a cage (404). It should be understood that cartridge (401) of this example may be configured and operable just like cartridge (30) described above, except for the differences explicitly noted herein. Notch cage securement (406) is sized and shaped to associate notch abutments (408) of cartridge body (402) with deflectors (410) of cage (404) at proximal end portion (460) of cage (404) to provide resistance of cage (404) against cartridge body (402) and inhibit movement of cage (404) from the closed position. As depicted in FIGS. 14A-14B, notch abutment (408) is configured to resiliently engage proximal end (460) to thereby substantially retain cage (404) in the closed position. Upon exertion by the operator of the predetermined opening force to overcome the resilient bias, notch abutments (408) cause deflectors (410) of cage (404) to deflect laterally and outwardly. Notch abutments (408) thus allow cage (404) to slidably translate from the closed position toward the opened position.

C. Bump Cage Securement

Figure 15:
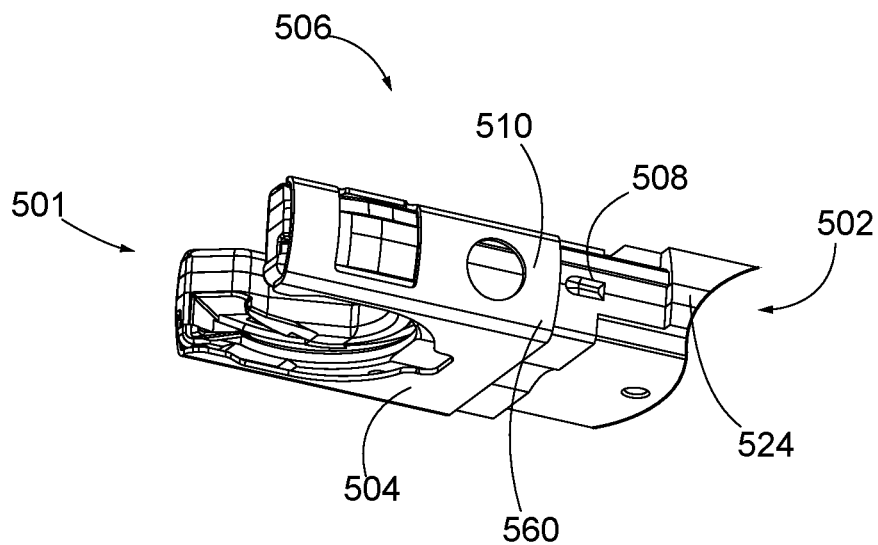
FIG. 15 depicts an enlarged bottom perspective view of another exemplary cartridge configured for receipt in the cartridge receiving assembly of FIG. 2A, with a first exemplary bump cage securement.

FIG. 15 illustrates a cartridge (501) with a first exemplary bump cage securement (506) comprising a bump abutment (508) projecting from a cartridge body (502) adjacent a proximal end portion (560) of a cage (504). It should be understood that cartridge (501) of this example may be configured and operable just like cartridge (30) described above, except for the differences explicitly noted herein. Bump cage securement (506) is sized and shaped to associate bump abutment (508) of cartridge body (502) with a deflector (510) located at proximal end portion (560) of cage (504). Bump abutment (508) and deflector (510) thereby provide resistance of cage (504) against cartridge body (502) and inhibit movement of cage (504) from the closed position toward the opened position within the elongate slot (104) (see FIG. 8). Upon exertion by the operator of the predetermined opening force greater than that amount of resistance generated by bump cage securement (506), bump abutment (508) causes deflector (510) of cage (504) to deflect laterally and outwardly to allow cage (504) to slidably translate from the closed position toward the opened position.

In the present example, a lateral side (524) of cartridge body (502) includes bump abutment (508) extending outwardly adjacent to proximal end portion (560) of cage (504). Although bump abutment (508) extends along the lateral length of lateral side (524) of cartridge body (502) over a relatively small length, it should be understood that the size and shape of bump abutment (508) may vary. While the present example includes one bump abutment (508) on lateral side (524) of cartridge body (502) and one deflector (510) on proximal end portion (560) of cage (504), alternative examples may have multiple bump abutments (508) and deflectors (510) along either one of both lateral side (524) of cartridge body (502) and cage (504).

Figure 16:
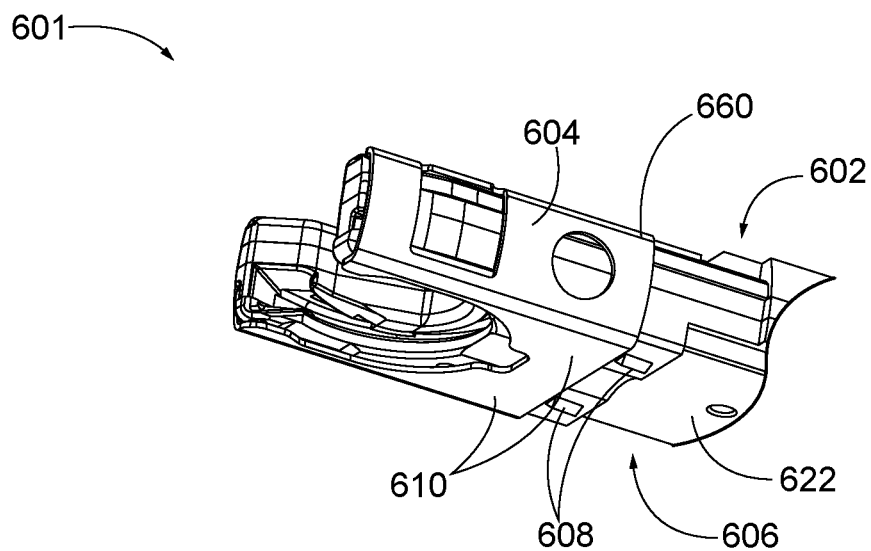
FIG. 16 depicts an enlarged bottom perspective view of another exemplary cartridge configured for receipt in the cartridge receiving assembly of FIG. 2A, second exemplary bump cage securement.
Figure 17:
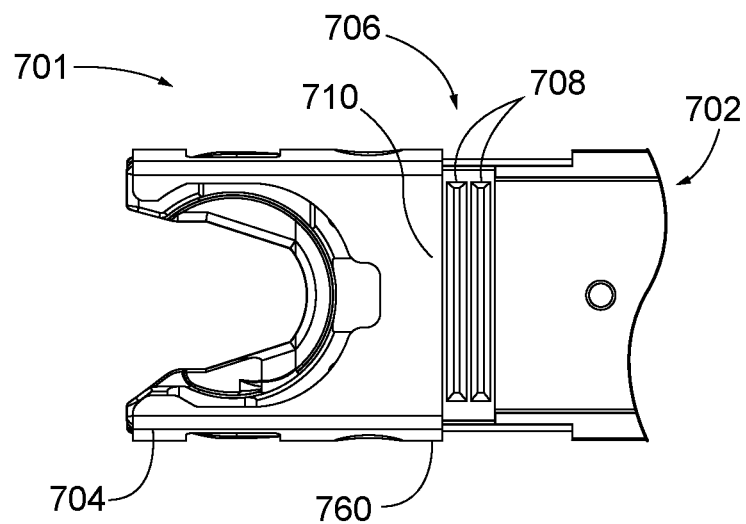
FIG. 17 depicts an enlarged bottom plan view of another exemplary cartridge configured for receipt in the cartridge receiving assembly of FIG. 2A, with a third exemplary bump cage securement.

As shown in FIG. 16, another cartridge (601) has a second exemplary bump cage securement (606) positioned on a lower surface (622) of a cartridge body (602) adjacent to a proximal end portion (660) of a cage (604). It should be understood that cartridge (601) of this example may be configured and operable just like cartridge (30) described above, except for the differences explicitly noted herein. As illustrated, bump abutments (608) extend outwardly from a cartridge body (602) to create resistance against proximal end portion (660) of cage (604) at deflectors (610). By way of further example, as depicted in FIG. 17, a cartridge (701) has a third exemplary bump cage securement (706) with a series of bump abutments (708) extending upwardly in a perpendicular direction to a longitudinal length of a cartridge body (702). It should be understood that cartridge (701) of this example may be configured and operable just like cartridge (30) described above, except for the differences explicitly noted herein.

Figure 18:
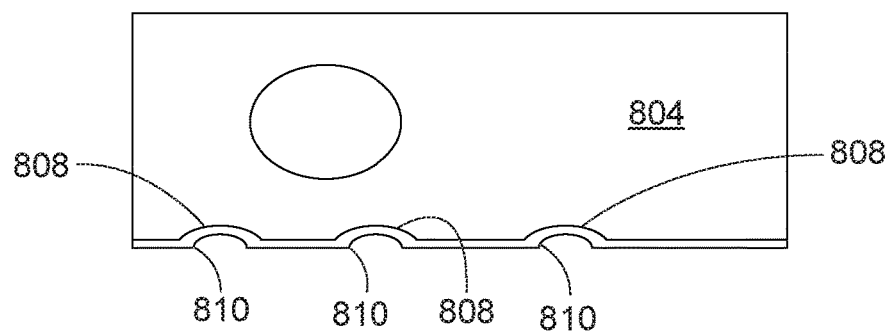
FIG. 18 depicts a side view of a fourth exemplary bump cage securement for a cartridge configured for receipt in the cartridge receiving assembly of FIG. 2A.

A fourth exemplary bump cage securement (806) shown FIG. 18 has a plurality of laterally extending bump abutments (808) along a cage (804). Each bump abutment (808) extends upwardly from respective deflectors (810) such that deflection of deflectors (810) similarly deflects bump abutments (808) as discussed above with respect to bump cage securement (506) (see FIG. 15). Bump abutments (808) and deflectors (810) are more particularly integrally and unitarily formed. In the present example, bump abutments (808) are configured to resiliently engage cartridge body (702) and thereby substantially retain cage (804) in the closed position. Upon exertion by the operator of the predetermined opening force to overcome the resilient bias, bump abutments (808) cause deflectors (810) to deflect outwardly and laterally. Bump abutments (808) thus allow cage (804) to slidably translate from the closed position toward the opened position. In some versions, bump abutments (808) engage cartridge body (702) to selectively inhibit movement toward the opened position. In some other versions, as shown in FIGS. 17 and 18, cage (804) with bump abutments (808) is used in place of cage (704) such that bump abutments (808) on cage (804) longitudinally engage bump abutments (708) on cartridge body (702). Accordingly, one or both of bump abutments (708, 808) may be configured to deflect to allow proximal movement of cage (804) toward the opened position.

Figure 19:
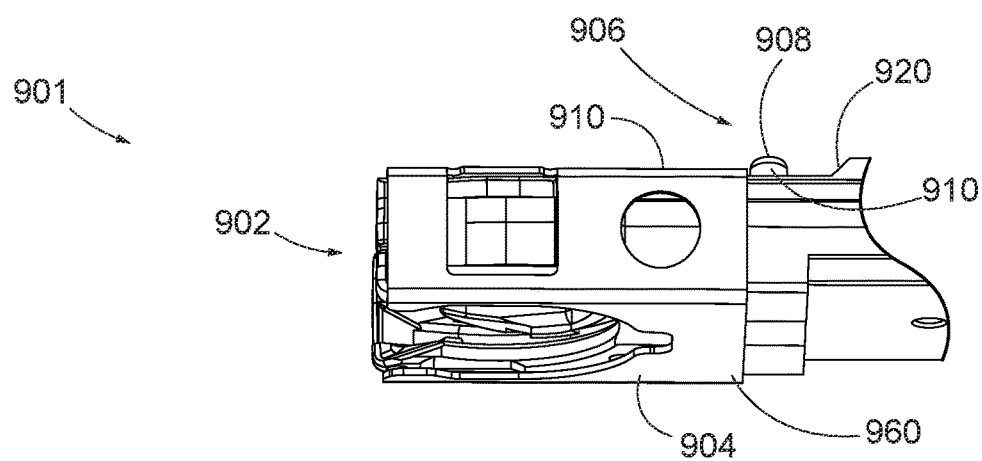
FIG. 19 depicts an enlarged bottom perspective view of another exemplary cartridge configured for receipt in the cartridge receiving assembly of FIG. 2A, with a fifth exemplary bump cage securement.

As shown in FIG. 19, another cartridge (901) has a fifth exemplary bump cage securement (906) formed by yet another bump abutment (908). It should be understood that cartridge (901) of this example may be configured and operable just like cartridge (30) described above, except for the differences explicitly noted herein. Bump abutment (908) projects upwardly from an upper surface (920) of a cartridge body (902) with a deflector (910) extending therebetween. Bump abutment (908) is configured to effectively block proximal movement of a cage (904) relative to cartridge body (902) up to the application of the predetermined opening force. Bump abutment (908) is configured to resiliently engage proximal end (860) and thereby substantially retain cage (804) in the closed position. Upon exertion by the operator of the predetermined opening force to overcome the resilient bias, deflector (910) deflects upwardly and laterally to thereby allow cage (904) to move from the closed position to the opened position. Bump abutment (908), deflector (910), and cartridge body (902) of the present example are integrally and unitarily formed. However, bump abutment (908), deflector (910), and cartridge body (902) may be alternatively constructed of various components and materials for resilient and/or plastic deformation that allows such inhibited movement of cage (904).

Figure 20:
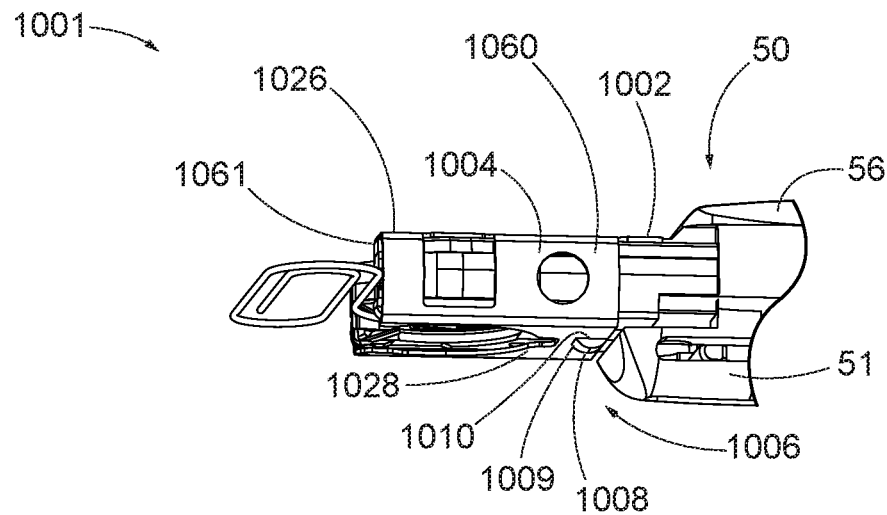
FIG. 20 depicts an enlarged bottom perspective view of another exemplary cartridge configured for receipt in the cartridge receiving assembly of FIG. 2A, with a sixth exemplary bump cage securement.

FIG. 20 illustrates a cartridge (1001) with a sixth exemplary bump cage securement (1006) that comprises a bump abutment (1008) extending from a lower surface (1028) of a cage (1004) adjacent a lower jaw (51) of a cartridge receiving assembly (50). It should be understood that cartridge (1001) of this example may be configured and operable just like cartridge (30) described above, except for the differences explicitly noted herein. Bump cage securement (1006) is sized and shaped to associate bump abutment (1008) with a deflector (1010) located at a proximal end portion (1060) of cage (1004) to provide resistance of cage (1004) against lower jaw (51) and inhibit movement of cage (1004) from the closed position to the opened position within elongate slot (104). Upon exertion by the operator of the predetermined opening force greater than that amount of resistance generated by bump cage securement (1006), bump abutment (1008) causes deflector (1010) and a lower surface (1028) of cage (1004) to deflect upwardly. Bump abutment (1008) thus allows cage (1004) to slidably translate from the closed position toward the opened position through elongate slot (104).

In the example shown in FIG. 20, bump abutment (1008) of bump cage securement (1006) is chamfered and extends from lower surface (1028) of cage (1004) with a chamfered end (1009) of bump abutment (1008) facing a distal end portion (1061) of cage (1004). Chamfered end (1009) of abutment (1008) is positioned along a proximal end portion (1060) of cage (1004) and centered laterally to align with a center of lower jaw (51). It should be understood that the chamfered end (1009) of abutment (1008) could be laterally aligned with lower jaw (51) of cartridge receiving assembly (50) at varying locations. Bump abutment (1008) is configured to resiliently engage lower jaw (51) and thereby substantially retain cage (1004) in the closed position. Upon exertion by the operator of the predetermined opening force to overcome the resilient bias, deflector (1010) positioned along proximal end portion (1060) deflects upwardly and laterally to allow cage (1004) to slidably translate from the closed position to the opened position. Bump abutment (1008) and deflector (1010) of bump cage securement (1006) are integrally and unitarily formed. Although not shown, it should be understood that bump cage securement (1006) may comprise multiple bump abutments (1008) on lower surface (1028) of cage (1004).

Figure 21:
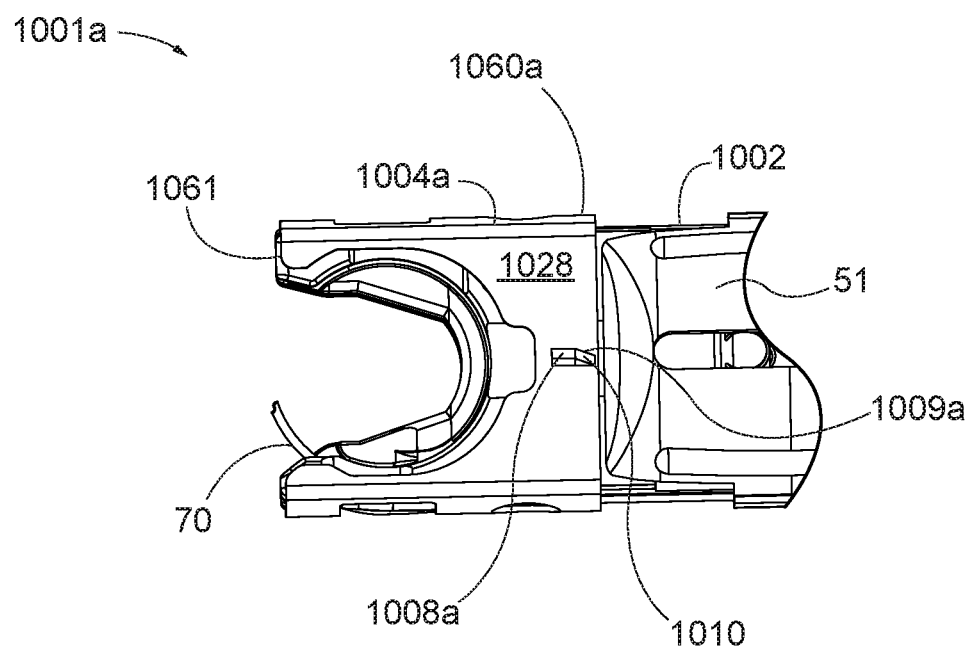
FIG. 21 depicts an enlarged bottom view of another exemplary cartridge configured for receipt in the cartridge receiving assembly of FIG. 2A, with a seventh exemplary bump cage securement.

FIG. 21 shows an exemplary alternative cartridge (1001a) having a seventh exemplary bump cage securement (1006a), where a chamfered end (1009a) of bump abutment (1008a) faces a proximal end portion (1060a) of a cage (1004a). It should be understood that cartridge (1001a) of this example may be configured and operable just like cartridge (30) described above, except for the differences explicitly noted herein. Bump abutment (1008a) is configured to resiliently engage lower jaw (51) and thereby substantially retain cage (1004a) in the closed position. Upon exertion by the operator of the predetermined opening force to overcome the resilient bias, deflector (1010) positioned along proximal end portion (1060a) deflects upwardly and laterally to allow cage (1004a) to slidably translate to the opened position. In some other versions, it may be desirable to position bump abutment (1008a) of chamfered bump cage securement (1006a) on an upper surface (not shown) of cage (1004a). Although bump abutment (1008a) and deflector (1010a) of the present example are shown as being integrally and unitarily formed, it should be understood that in other examples each may comprise separately formed features of varying sizes, shapes, and/or lengths.

Figure 22:
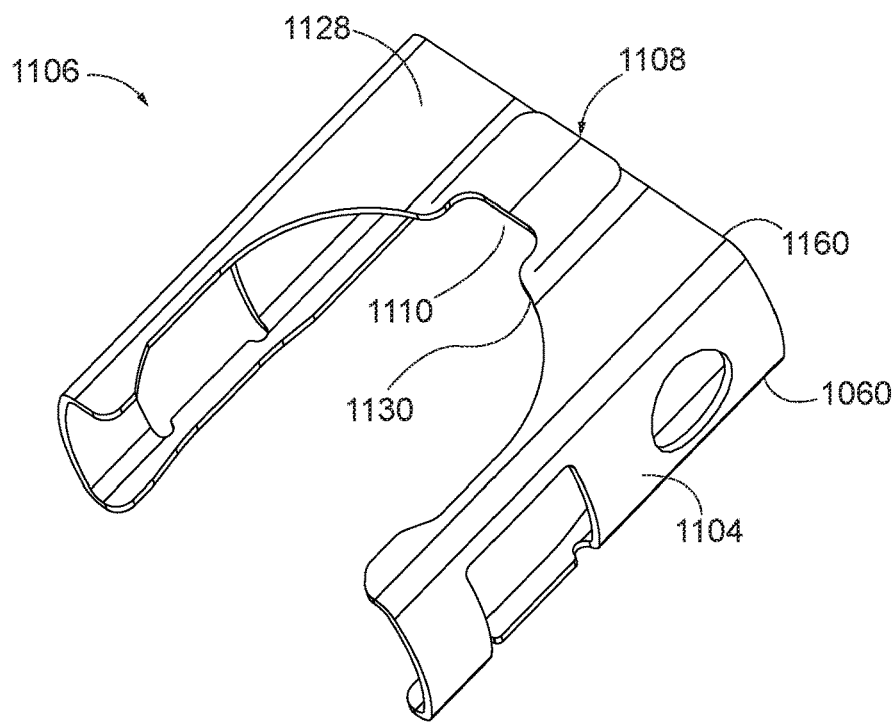
FIG. 22 depicts an enlarged bottom perspective view of another exemplary cartridge configured for receipt in the cartridge receiving assembly of FIG. 2A, with an eighth exemplary bump cage securement.

FIG. 22 illustrates an eighth exemplary bump cage securement (1106) with a bump abutment (1108) on a cage (1104) having a raised lower surface (1128) at a proximal end portion (1160) thereof. As shown in the present example, bump abutment (1108) extends along a lateral length less than the lateral length of proximal end portion (1160) of cage (1104). However, it should be understood that the lateral length of bump abutment (1108) may consist of a length greater than that shown in FIG. 22 and up to an extent equal to the lateral length of proximal end portion (1160) of cage (1104). It may also be desirable to include a shape or size of bump abutment (1108) that varies in comparison to that depicted in the exemplary version. A deflector (1110) of bump cage securement (1106) comprises a portion of cage (1104) similar to bump abutment (1108) in that deflector (1110) and bump abutment (1108) of bump cage securement (1106) are integrally and unitarily formed. However, it should be understood that in other examples each may comprise separately formed features of varying sizes, shapes, and/or lengths. Additionally, although not shown, bump abutment (1108) may be positioned along proximal end portion (1160) and/or an upper surface (1126) of cage (1104). In some examples, bump abutment (1108) may be positioned on an internal surface (1130) of cage (1104). As with other components described herein, bump cage securement (1106) may be relocated, varied, modified, substituted, or supplemented in a variety of ways. Bump cage securement (1106) of cage (1104) is made from a material similar to that of cage (1104), however it should be understood that bump cage securement (1106) may be made from various materials that resiliently and/or plastically deflect cage (1104). In the present example, bump abutment (1108) is configured to resiliently engage lower jaw (51) (not shown) and thereby substantially retain cage (1104) in the closed position. Upon exertion by the operator of the predetermined opening force to overcome the resilient bias, deflector (1110) deflects upwardly and laterally thereby allowing cage (1104) to slidably translate from the closed position to an opened position.

D. Flex Tab Cage Securement

Figure 23:
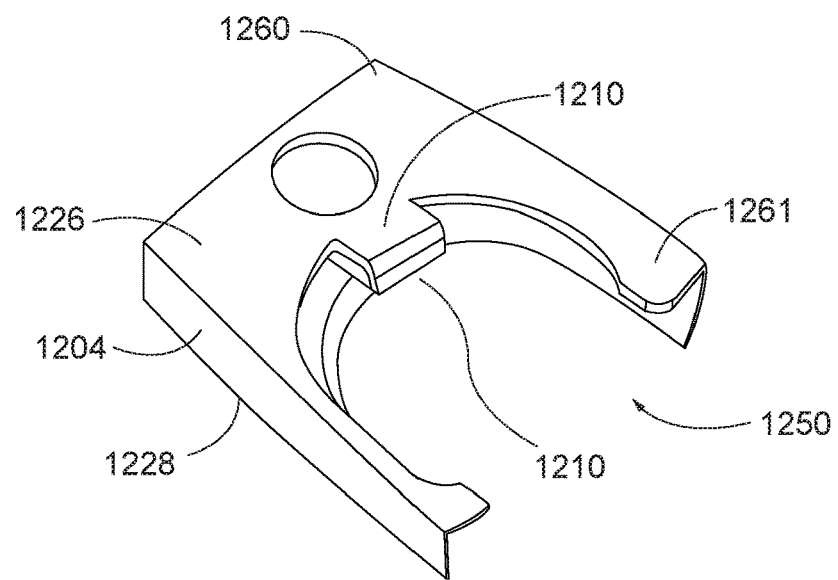
FIG. 23 depicts an enlarged bottom perspective view of an exemplary flex tab cage securement for a cartridge configured for receipt in the cartridge receiving assembly of FIG. 2A.

FIG. 23 illustrates an exemplary flex tab cage securement (1206) on a cage (1204). Cage (1204), similar to the configuration of cage (1104), includes a flex abutment (1208) adjacent a proximal end portion (1260). Flex tab cage securement (1206) is sized and shaped to associate flex abutment (1208) of cage (1204) with a deflector (1210) located adjacent flex abutment (1208) to provide resistance of cage (1204) against cartridge body (1002) (see FIG. 20) and inhibit movement of cage (1204) from the closed position to the opened position through elongate slot (104) (see FIG. 20). Upon exertion by the operator of the predetermined opening force greater than that amount of resistance generated by flex tab cage securement (1206), flex abutment (1208) is urged downwardly by cartridge body (1002) (see FIG. 20). Deflector (1210) thereby deflects downwardly to allow cage (1204) to slidably translate from the closed position toward the opened position through elongate slot (104) (see FIG. 20).

In the present example, flex abutment (1208) extends toward a distal end portion (1261) of cage (1204) and outwardly towards a cavity (1250). As shown, flex abutment (1208) of flex tab securement (1206) is shaped and sized to extend into cavity (1250) at a length to engage cartridge body (1002) (see FIG. 20). In some examples, it may be desirable to extend flex abutment (1208) into cavity (1250) at an alternative length less than or greater than that shown in FIG. 23. By way of further example, it may be desirable to include flex abutment (1208) of flex tab cage securement (1206) at varying locations on cage (1204) facing cavity (1250). In the present example, flex abutment (1208) and deflector (1210) of flex tab securement (1206) are integrally and unitarily formed such that flex abutment (1208) extends distally from deflector (1210). In the present example, flex abutment (1208) upwardly extends towards cavity (1250) to resiliently engage cartridge body (1002) (see FIG. 20) and thereby substantially retain cage (1204) in the closed position. Upon exertion by the operator of the predetermined opening force to overcome the resilient bias, flex abutment (1208) and deflector (1210) are biased downwardly and laterally to thereby allow cage (1204) to slidably translate from the opened position to the closed position. However, it should be understood that in other examples each may comprise separately formed features of varying sizes, shapes, and/or lengths. Additionally, although the present example includes one flex abutment (1208) and one respective deflector (1210) on cage (1204), it should be understood that multiple flex abutments (1208) and deflectors (1210) may be provided along either a lower surface (1228) or an upper surface (1226) of cage (1204).

E. Knock Cage Securement

Figure 24A:
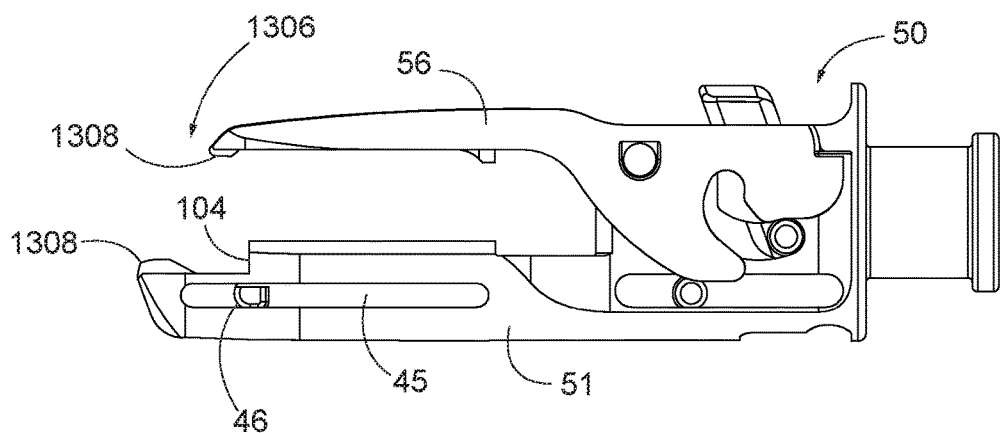
FIG. 24A depicts a side view of an exemplary cartridge receiving assembly that may be incorporated into the instrument of FIG. 1, with an exemplary knock cage securement.
Figure 24B:
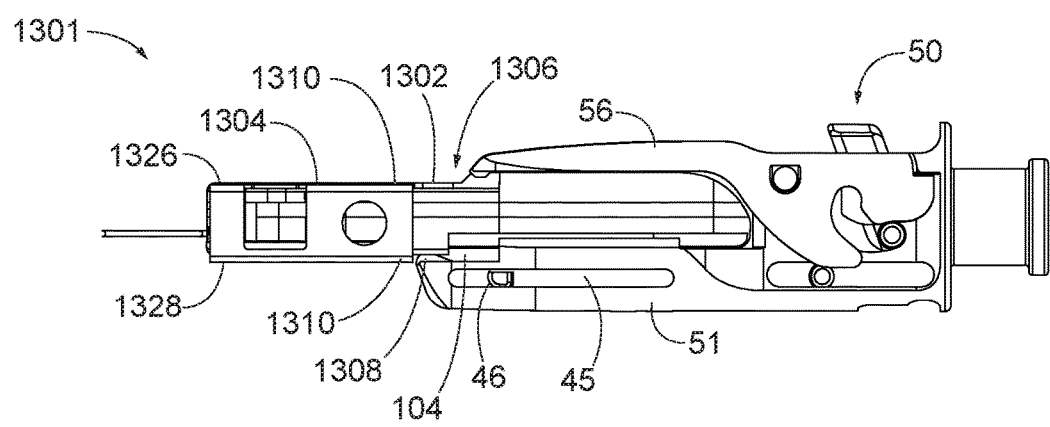
FIG. 24B depicts a side view of the cartridge receiving assembly and knock cage securement of FIG. 24A having received an exemplary cartridge in a closed position.

FIGS. 24A-24B illustrate a cartridge (1301) with an exemplary knock cage securement (1306) including a pair of knock abutments (1308) extending from cartridge receiving assembly (50). It should be understood that cartridge (1301) of this example may be configured and operable just like cartridge (30) described above, except for the differences explicitly noted herein. Knock cage securement (1306) is sized and shaped to associate knock abutments (1308) with a respective pair of deflectors (1310) on a cage (1304) to provide resistance of cage (1304) toward lower jaw (51) and upper jaw (56) and inhibit movement of cage (1304) from the closed position to the opened position through elongate slot (104). Upon exertion by the operator of the predetermined opening force greater than that amount of resistance generated by knock cage securement (1306), knock abutments (1308) cause deflectors (1310) with cage (1304) to deflect inward to allow cage (1304) to slidably translate toward the opened position.

In the present example, cartridge receiving assembly (50) has two flex abutments (1308) located on lower jaw (51) and upper jaw (56), respectively. In some examples, it may be desirable to include more or fewer flex abutments (1308) on lower jaw (51) and/or upper jaw (56) of cartridge receiving assembly (50). The corresponding heights of pin (46) and rack (45) may be adjusted accordingly to accommodate flex abutments (1308) while maintaining sufficient size of elongate slot (104) to allow cage (1304) to be proximally translated by the operator. Deflectors (1310) of knock cage securement (1306) are positioned respectively on an upper surface (1326) and a lower surface (1328) of cage (1304) to correspond respectively with flex abutments (1308) on upper jaw (56) and lower jaw (51). Deflectors (1310) are sized and shaped to associate with flex abutments (1308) and deflect cage (1304) inwardly towards cartridge body (1302) upon exertion of force by the operator.

F. Contact Cage Securement

Figure 25A:
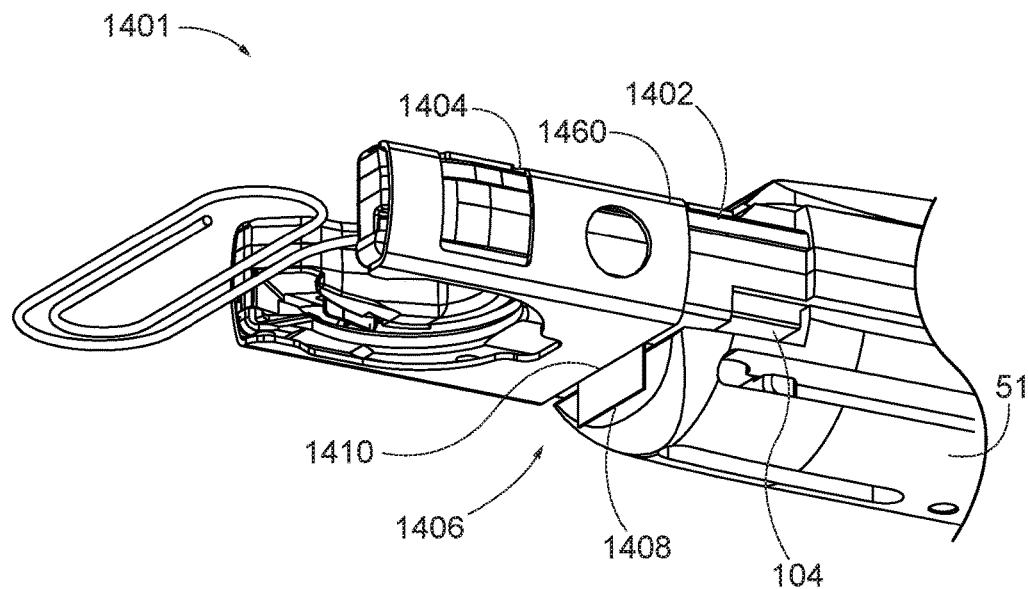
FIG. 25A depicts an enlarged bottom perspective view of an exemplary cartridge with a first exemplary contact cage securement in the cartridge receiving assembly of FIG. 2A, with a cage of the cartridge in a closed position.
Figure 25B:
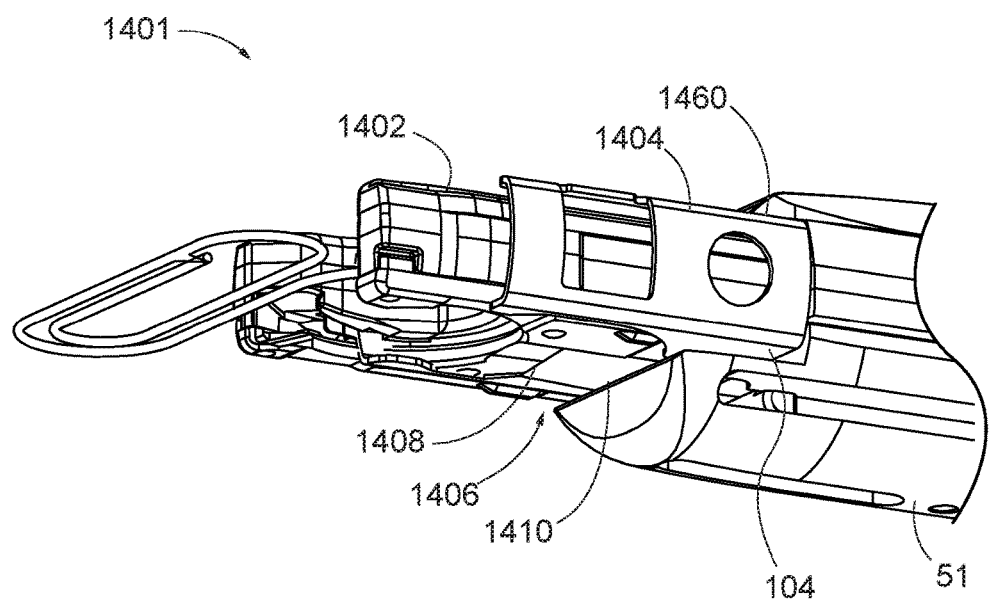
FIG. 25B depicts the enlarged bottom perspective view of the cartridge of FIG. 25A, with the cage in an opened position.

FIGS. 25A-2BB illustrate a cartridge (1401) with a first exemplary contact cage securement (1406) having a contact abutment (1408) projecting between a cartridge body (1402) and a cage (1404). It should be understood that cartridge (1401) of this example may be configured and operable just like cartridge (30) described above, except for the differences explicitly noted herein. Contact cage securement (1406) is sized and shaped to associate a deflector (1410) with a contact abutment (1408), which extends from deflector (1410) to provide resistance of cage (1404) along cartridge body (1402) and inhibit movement of cage (1404) from the closed position toward the opened position. More particularly, deflector (1410) with contact abutment (1408) are attached to cage (1404). In the present example, contact abutment (1408) is configured to resiliently engage proximal end portion (1460) and thereby substantially retain cage (1404) in the closed position. Upon exertion by the operator of the predetermined opening force to overcome the resilient bias, contact abutment (1408) causes deflector (1410) to deflect distally. Contact abutment (1408) then pivots to flatten against cage (1404) thereby allowing cage (1404) to slidably translate away from the closed position and toward the opened position through elongate slot (104). In the present example, contact abutment (1408) is tab-shaped and positioned between cartridge body (1402) and cage (1404). Contact abutment (1408) and deflector (1410) of contact cage securement (1406) are integrally and unitarily formed. However it should be understood that in other examples each may comprise separately formed features of varying sizes, shapes, and/or lengths.

Figure 26A:
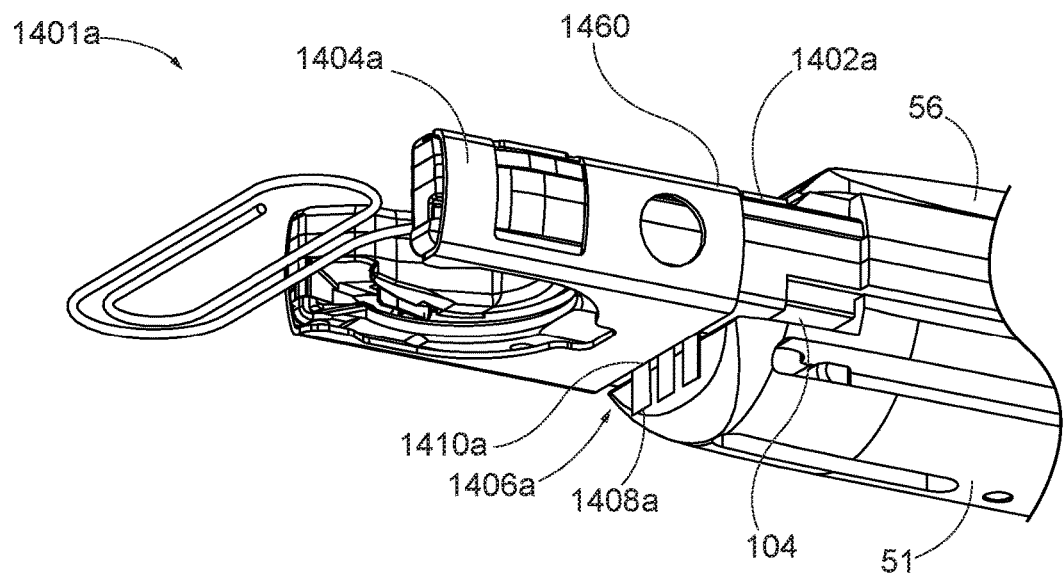
FIG. 26A depicts an enlarged bottom perspective view of an exemplary cartridge with a second exemplary contact cage securement in the cartridge receiving assembly of FIG. 2A, with a cage of the cartridge in a closed position.
Figure 26B:
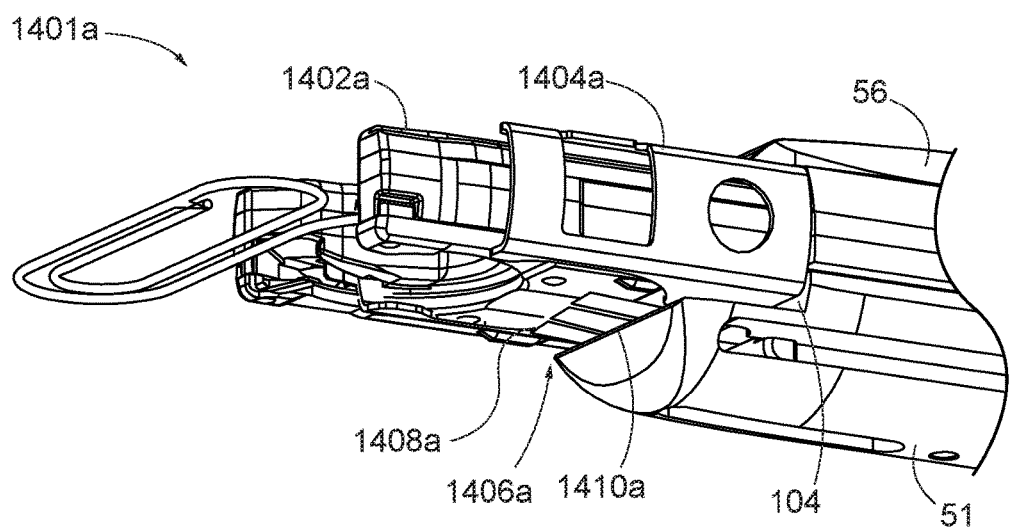
FIG. 26B depicts the enlarged bottom perspective view of the cartridge and the contact cage securement of FIG. 26A, with the contact cage securement in an opened position.

By way of another example, as seen in FIGS. 26A-26B, another cartridge (1401a) has a second exemplary contact cage securement (1406a) that includes a plurality of contact abutments (1408a) and a respective plurality of deflectors (1410a) between cartridge body (1402a) and cage (1404a). It should be understood that cartridge (1401a) of this example may be configured and operable just like cartridge (30) described above, except for the differences explicitly noted herein. Contact cage securements of FIGS. 25A-26B (1406, 1406a) are made from a plastic material and/or a metallic material. However it should be understood that contact cage securements (1406, 1406a) may be made from various materials that resiliently and/or plastically inhibit movement between cartridge body (1402, 1402a) and cage (1404, 1404a).

G. Tongue Cage Securement

Figure 27A:
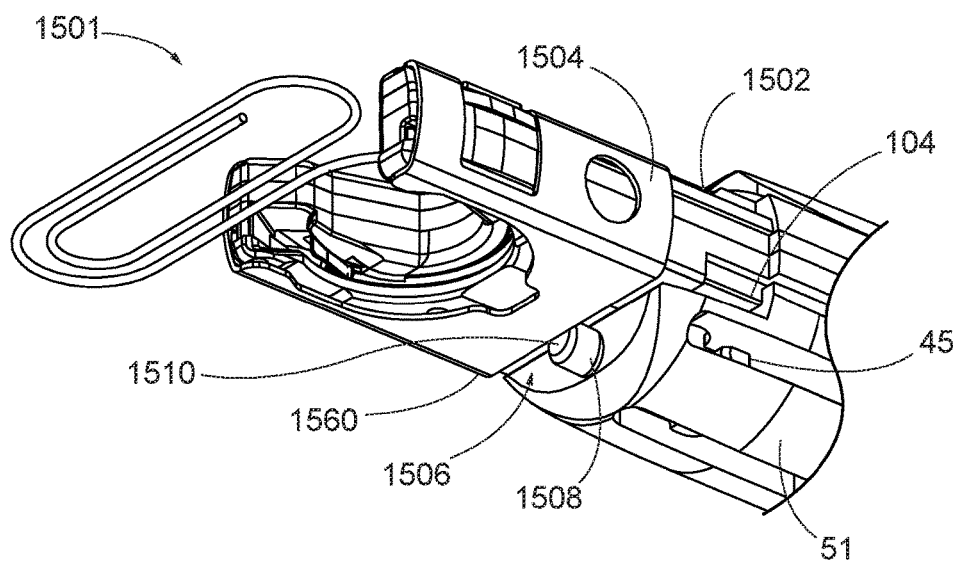
FIG. 27A depicts an enlarged bottom perspective view of an exemplary cartridge receiving assembly and an exemplary cartridge with a first exemplary tongue cage securement, with a cage in a closed position.
Figure 27B:
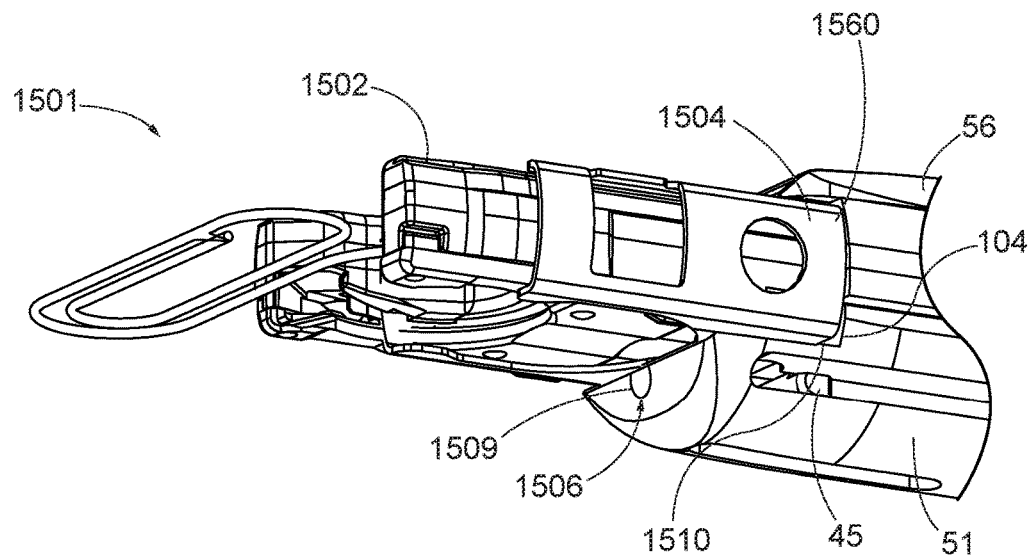
FIG. 27B depicts the enlarged bottom perspective view of the cartridge receiving assembly and the cartridge of FIG. 27A, with the tongue cage securement in an opened position.

FIGS. 27A-27B illustrate a cartridge (1501) and a first exemplary tongue cage securement (1506) formed by a tongue abutment (1508) projecting from a portion of a cartridge receiving assembly (50). It should be understood that cartridge (1501) of this example may be configured and operable just like cartridge (30) described above, except for the differences explicitly noted herein. Moreover, cartridge receiving assembly (50) in this example is configured and operable just like cartridge receiving assembly (50) described above, with the exception of cartridge receiving assembly (50) including tongue abutment (1508) in this example. Tongue cage securement (1506) is sized and shaped to associate tongue abutment (1508) of cartridge receiving assembly (50) with a cage (1504) of cartridge (1501) to provide resistance against cage (1504) and inhibit movement of cage (1504) from the closed position to the opened position within elongate slot (104). More particularly, upon retraction of rack (45) by the operator in the proximal direction, tongue abutment (1508) is simultaneously retracted in the proximal direction into lower jaw (51) of cartridge receiving assembly (50) and away from cage (1504) to effectively clear elongate slot (104). In turn, cage (1504) is free to slidably translate from the closed position toward the opened position through elongate slot (104).

In the present example, tongue abutment (1508) of tongue cage securement (1506) extends distally from rack (45) and is positioned along the centerline of lower jaw (51) to align with a proximal end portion (1560) of cage (1504). Tongue abutment (1508) more particularly extends distally beyond rack (45) and lower jaw (51) through an aperture (1509) positioned on a portion of lower jaw (51) in parallel extension with rack (45). Tongue abutment (1508) of tongue cage securement (1506) in a distal position exerts a resistant force against the proximal movement of cage (1504) to hold cage (1504) in the closed position. The retraction of rack (45) causes tongue abutment (1508) to retract proximally through aperture (1509) to a proximal position and allows cage (1504) to move proximally toward the opened position.

Figure 28:
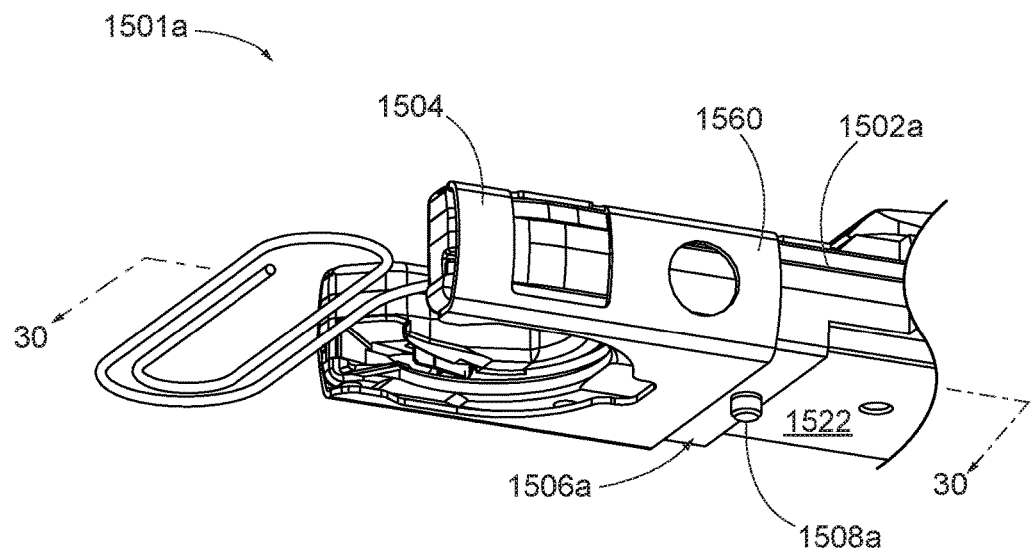
FIG. 28 depicts an enlarged bottom perspective view of an exemplary cartridge configured for receipt in the cartridge receiving assembly of FIG. 2A, with a second exemplary tongue cage securement.
Figure 29:
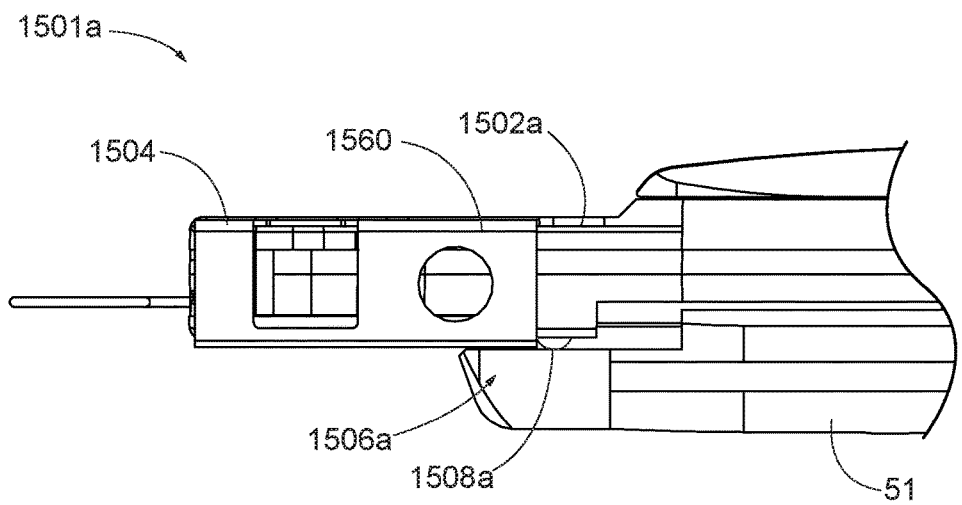
FIG. 29 depicts a side view of the cartridge of FIG. 28.
Figure 30:
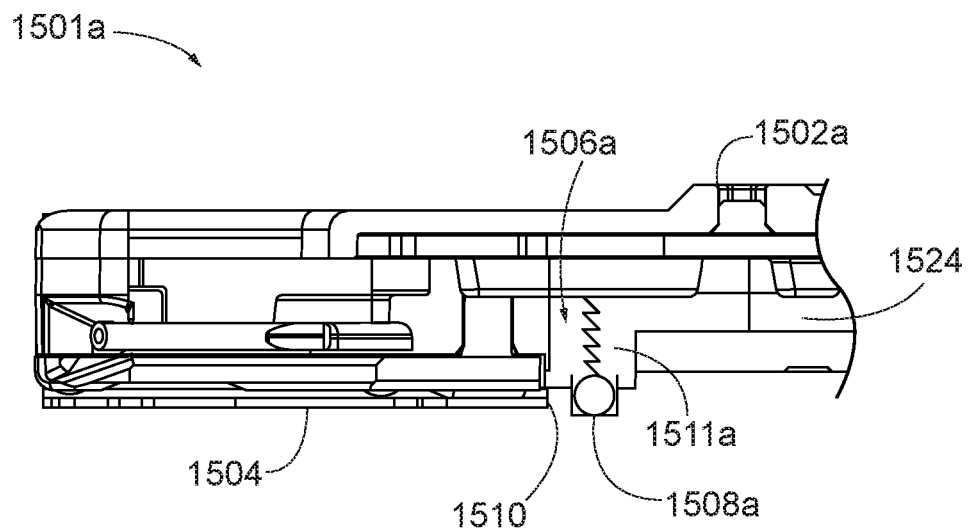
FIG. 30 depicts a cross-sectional view of the cartridge of FIG. 28 taken along line 30-30 of FIG. 28.
Figure 31:
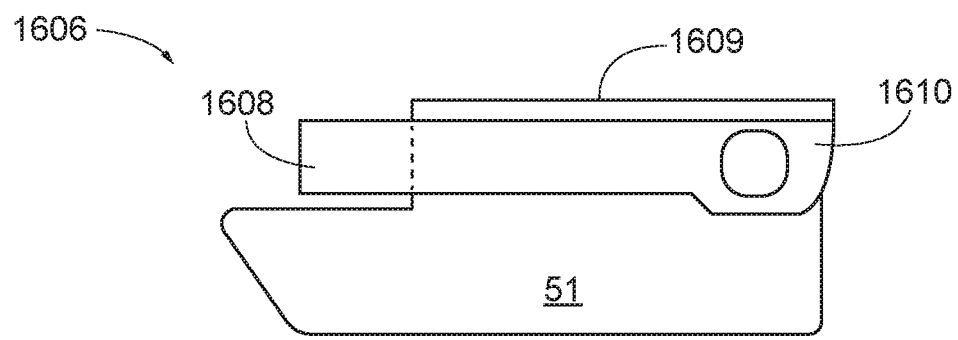
FIG. 31 depicts a side view of an exemplary cartridge receiving assembly that may be incorporated into the instrument of FIG. 1, with an exemplary slide cage securement.
Figure 32:
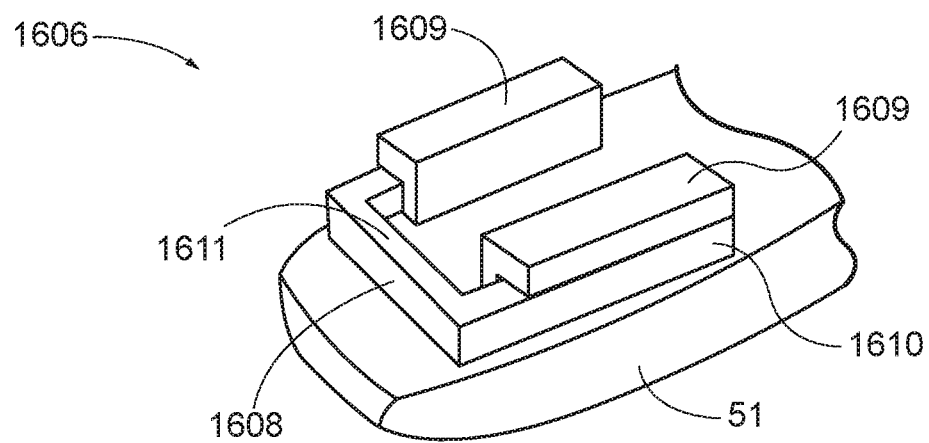
FIG. 32 depicts a top perspective view of the cartridge receiving assembly of FIG. 31.

As seen in FIGS. 28-29, another cartridge (1501a) has a second exemplary tongue cage securement (1506a) formed by a tongue abutment (1508a) extending resiliently from a cartridge body (1502a) adjacent to proximal end portion (1560) of cage (1504). It should be understood that cartridge (1501) of this example may be configured and operable just like cartridge (30) described above, except for the differences explicitly noted herein. Tongue abutment (1508a) extends transversely through a lower surface (1522a) of cartridge body (1502a) and exerts a linear resistant force against lower jaw (51) of cartridge receiving assembly (50) and a longitudinal resistant force against proximal end portion (1560) of cage (1504) to inhibit movement of cage (1504) from the closed position to the opened position through elongate slot (104). As further seen in FIG. 30, tongue abutment (1508a) is resiliently mounted in cartridge body (1502a) with a spring (1511a) extending therebetween and contained within cartridge body (1502a). However, it will be appreciated that alternative biasing members to spring (1511a) may be so used.

H. Slide Cage Securement

FIGS. 31-33B illustrate an exemplary slide cage securement (1606) on a cage (1504) (see FIG. 29). Slide cage securement (1606), like tongue cage securement (1506a) (see FIG. 29), is positioned adjacent to proximal end portion (1560) of cage (1504) (see FIG. 29). Slide cage securement (1606) includes a slide abutment (1608) positioned on an upper face of lower jaw (51). Slide cage securement (1606) is sized and shaped to associate slide abutment (1608) with a deflector (1610) located on a distal end portion of slide abutment (1608) to provide resistance against cage (1504) (see FIG. 29). Slide cage abutment (1608) is configured to resiliently engage proximal end portion (1560) (see FIG. 29) and thereby substantially retain cage (1504) in the closed position (see FIG. 29). Upon exertion by the operator of the predetermined opening force to overcome the resilient bias created by slide cage securement (1606), slide abutment (1608) and deflector (1610) deflect laterally to thereby allow cage (1504) (see FIG. 29) to slidably translate from the closed position toward the opened position through elongate slot (104) (see FIG. 29).

Figure 33A:
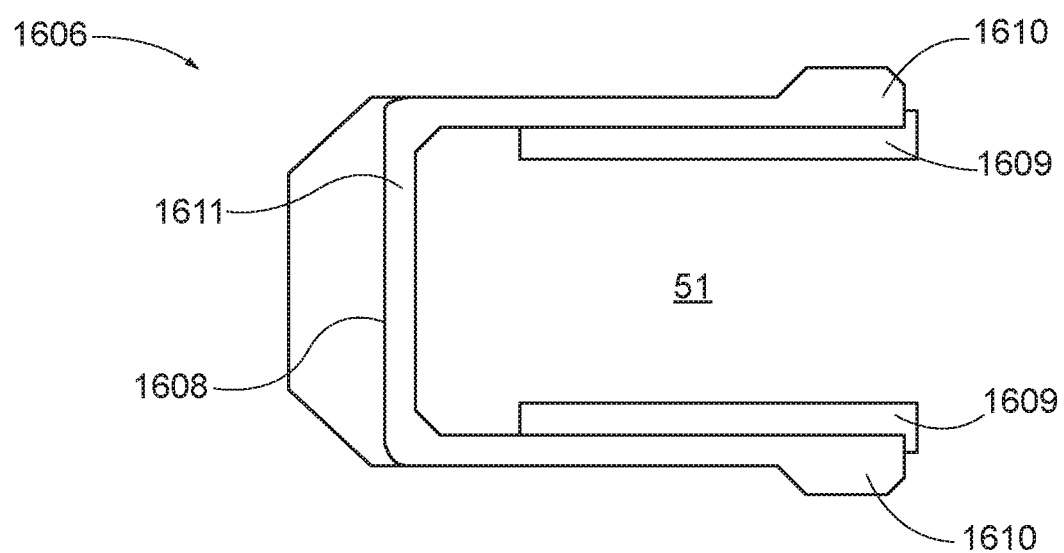
FIG. 33A depicts a top view of the cartridge receiving assembly of FIG. 31 with the slide cage securement in a cage closed position.
Figure 33B:
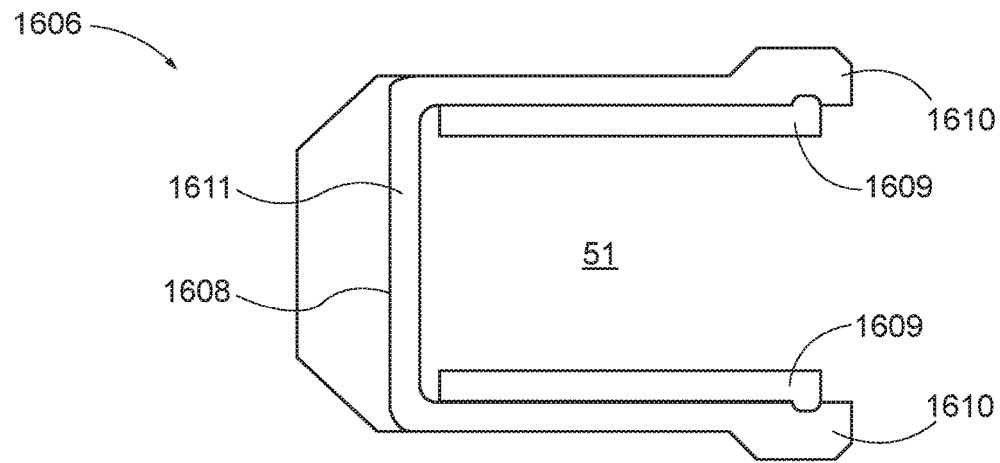
FIG. 33B depicts a top view of the cartridge receiving assembly of FIG. 31 with the slide cage securement in a cage opened position.

In the present example, slide abutment (1608) of slide cage securement (1606) is u-shaped comprising a front bar (1611). Slide abutment (1608) is movably attached to the upper face of lower jaw (51) by a pair of flanges (1609), which receive slide cage securement (1608) thereagainst. Slide abutment (1608) is in contact with cage (1504) (see FIG. 29) when fully extended in a distal position such that cage (1504) (see FIG. 29) is in the closed position. As best seen in FIGS. 33A-33B, slide abutment (1608) of slide cage securement (1606) translates toward the proximal position upon exertion by the operator of the predetermined opening force onto cage (1504) (see FIG. 29) until front bar (1611) of slide abutment (1608) contacts flanges (1609). Deflectors (1610) deflect laterally outwardly upon proximal exertion of force by the operator upon cage (1504) (see FIG. 29) to allow translation thereof until front bar (1611) stops against flanges (1609). Although slide abutment (1608) and deflectors (1610) of the present example are shown as being integrally and unitarily formed, it should be understood that in other examples each may comprise separately formed features of varying sizes, shapes, and/or lengths. In addition, the present example includes slide abutment (1608) of slide cage securement (1606) on lower jaw (51) of cartridge receiving assembly (50). However, cage securement (1606) may alternatively be provided along upper jaw (56) of cartridge receiving assembly (50).

I. Tab Cage Securement

Figure 34:
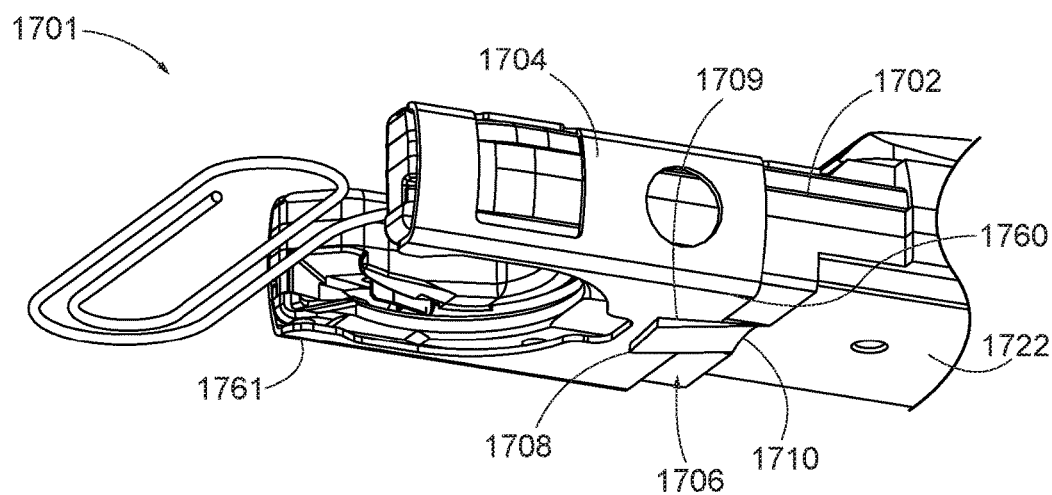
FIG. 34 depicts an enlarged bottom perspective view of an exemplary cartridge configured for receipt in the cartridge receiving assembly of FIG. 2A, with a first exemplary tab cage securement.
Figure 35:
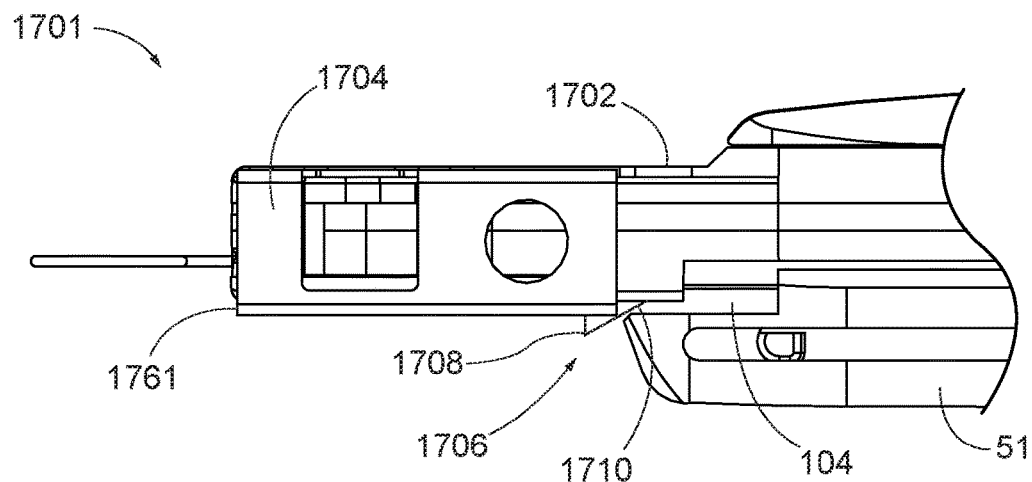
FIG. 35 depicts an enlarged side view of the cartridge of FIG. 34.

FIGS. 34-35 illustrate a cartridge (1701) with a first exemplary tab cage securement (1706) having a biasing abutment (1708) resiliently extending from a cartridge body (1702). It should be understood that cartridge (1701) of this example may be configured and operable just like cartridge (30) described above, except for the differences explicitly noted herein. Tab cage securement (1706) is sized and shaped to associate biasing abutment (1708) of cartridge body (1702) with a deflector (1710) positioned at a proximal end portion (1760) of a cage (1704) to provide resistance of cage (1704) along cartridge body (1702) and inhibit movement of cage (1704) toward the opened position. Upon transverse manipulation by the operator, biasing abutment (1708) recedes into cartridge body (1702) with deflector (1710) deflecting inwardly. Cage (1704) is thus configured to slidably translate from the closed position toward the opened position through elongate slot (104).

In the present example, biasing abutment (1708) is tapered and extends transversely and outwardly from a lower surface (1722) of cartridge body (1702) to be received in a tab receiver (1709) of cage (1704) along proximal end portion (1760) of cage (1704). Deflector (1710) of tab cage securement (1706) extends along the base of biasing abutment (1708) of tab cage securement (1706) and, in the present example, biasing abutment (1708) and deflector (1710) are integrally and unitarily formed. However, it should be understood that in other examples, biasing abutment (1708) and deflector (1710) may comprise separately formed features of varying sizes, shapes, and/or lengths. In some examples, it may be desirable to include biasing abutment (1708) of tab cage securement (1706) on upper surface (1720) of cartridge body (1702). As best seen in FIG. 35, biasing abutment (1708) of tab securement (1706) remains fully extended from cage (1704) until an inward, transverse force is applied by the operator to deflect deflector (1710) and biasing abutment (1708) inwardly toward cartridge body (1702).

Figure 36:
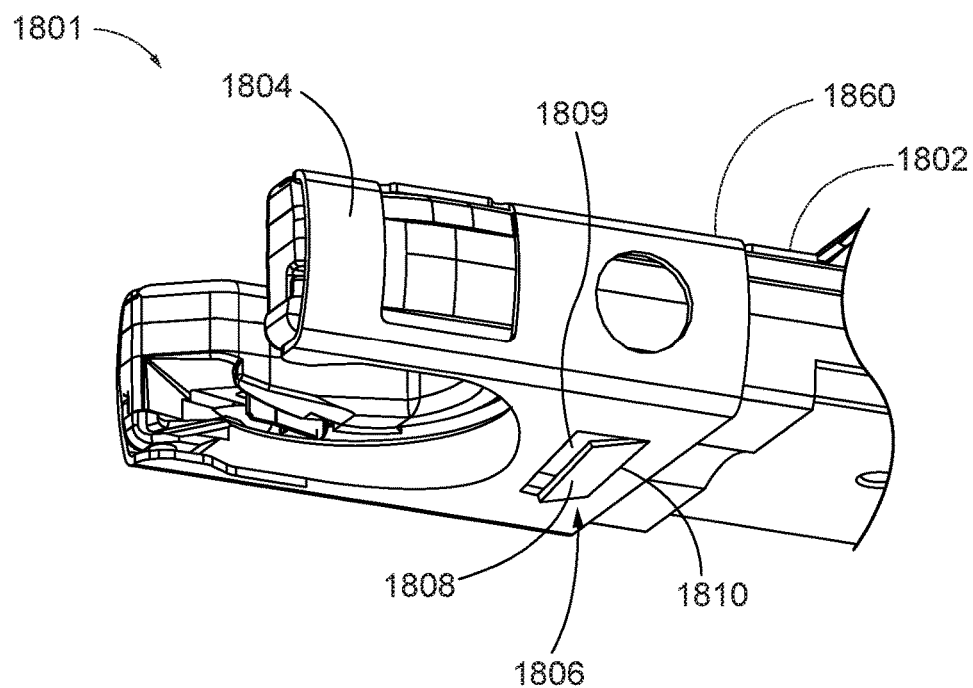
FIG. 36 depicts an enlarged bottom perspective view of an exemplary cartridge configured for receipt in the cartridge receiving assembly of FIG. 2A, with a second exemplary tab cage securement.

FIG. 36 illustrates a cartridge (1801) with a second exemplary tab cage securement (1806). It should be understood that cartridge (1801) of this example may be configured and operable just like cartridge (30) described above, except for the differences explicitly noted herein. Tab cage securement (1806) has a biasing abutment (1808) projecting from a cage (1804) by a deflector (1810) extending therebetween. Biasing abutment (1808) and deflector (1810) extend distally and transversely below cage (1804) for engagement with lower jaw (51) (see FIG. 35) to releasably hold cage (1804) in the closed position up to the predetermined opening force. Manipulating cage (1804) proximally toward the open position with at least the predetermined opening force causes lower jaw (51) (see FIG. 35) to urge biasing abutment (1808) resiliently within a tab receiving opening (1809) of cage (1804) to longitudinally clear lower jaw (51). Accordingly, cage (1804) is configured to be urged from the closed position toward the open position with at least the predetermined opening force. Biasing abutment (1808), deflector (1810), and cage (1804) are integrally and unitarily formed. However, it will be appreciated that biasing abutment (1808), deflector (1810), and cage (1804) may be alternatively formed of one or more structures and/or materials for resilient and/or plastic deflection upon movement toward the opened position.

Figure 37:
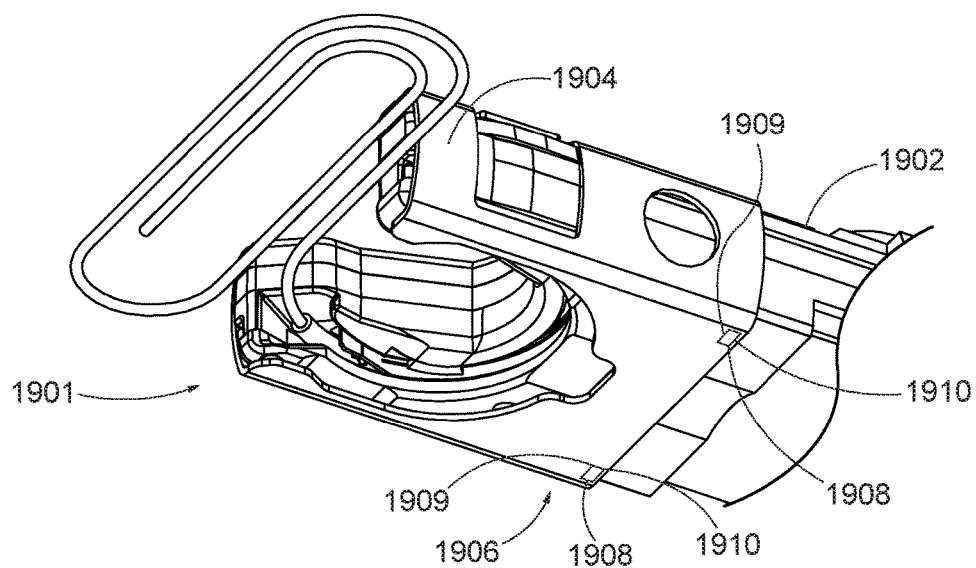
FIG. 37 depicts an enlarged bottom perspective view of an exemplary cartridge configured for receipt in the cartridge receiving assembly of FIG. 2A, with a third exemplary tab cage securement
Figure 38:
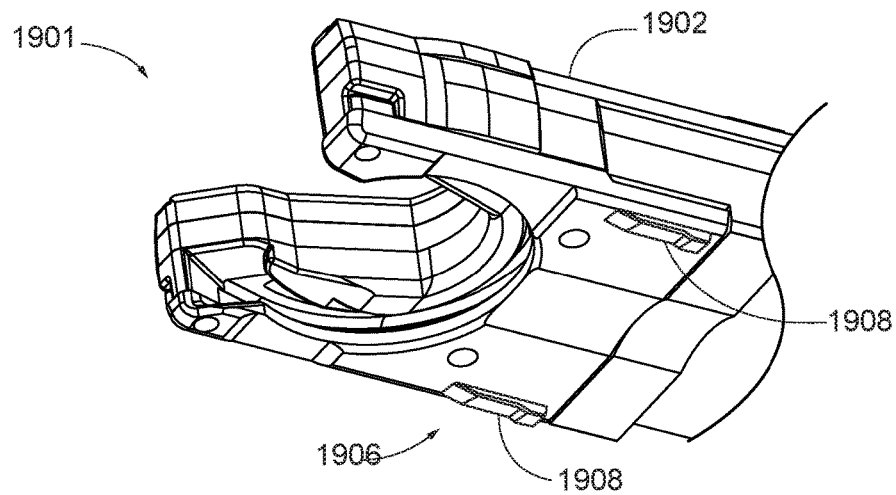
FIG. 38 depicts the enlarged bottom perspective view of the exemplary cartridge of FIG. 37, with various features removed for improved clarity.

As seen in FIGS. 37-38, a cartridge (1901) has a third exemplary tab cage securement (1906) that includes a pair of biasing abutments (1908) extending from a lower surface (1922) of a cartridge body (1902). It should be understood that cartridge (1901) of this example may be configured and operable just like cartridge (30) described above, except for the differences explicitly noted herein. Tab cage securement (1906) further includes a pair of tab receiver bores (1908) extending through a deflector portion (1910) of a cage (1904). Tab receiver bores (1908) are configured to releasably receive biasing abutments (1908) respectively to releasably secure cage (1904) in the closed position to cartridge body (1902). However, upon the application of the predetermined opening force on cage (1904), biasing abutments (1908) urge deflector surfaces (1910) to resiliently deflect such that biasing abutments (1908) longitudinally clear tab receiver bores (1908). Cage (1904) is thus configured to move from the closed position toward the opened position. While deflector portions (1910) of cage (1904) are configured to resiliently deflect in the present example such that biasing abutments (1908) snap into tab receiver bores (1908), biasing abutments (1908) may also be configured to resiliently deflect in alternative examples.

Figure 39:
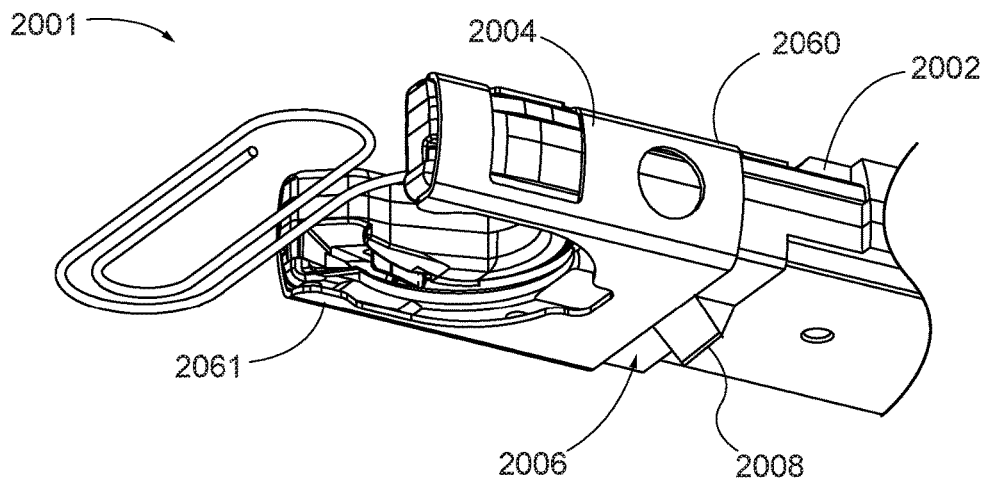
FIG. 39 depicts an enlarged bottom perspective view of an exemplary cartridge configured for receipt in the cartridge receiving assembly of FIG. 2A, with a fourth exemplary tab cage securement.
Figure 40:
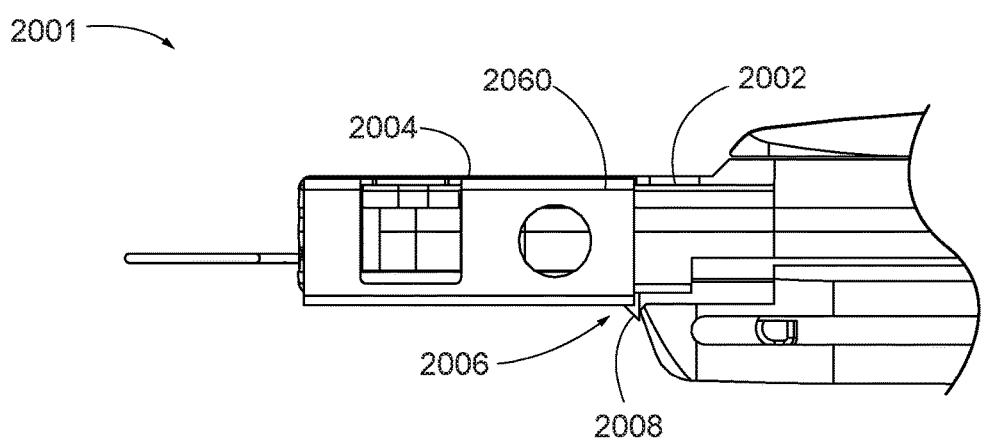
FIG. 40 depicts an enlarged side view of the cartridge of FIG. 39.

FIGS. 39-40 illustrate a cartridge (2001) with a fourth exemplary tab cage securement (2006) having a tapered biasing abutment (2008) positioned adjacent to a proximal end portion (2060) of a cage (2004). It should be understood that cartridge (2001) of this example may be configured and operable just like cartridge (30) described above, except for the differences explicitly noted herein. Tapered biasing abutment (2008) is resiliently mounted within a cartridge body (2002) to a deflector biasing element (not shown) to resiliently deflect in a transverse direction. Accordingly, tapered biasing abutment (2008) is configured to inhibit movement of cage (2004) from the closed position toward the open position up to the predetermined opening force. Upon the application of at least the predetermined opening force, cage (2004) slides against tapered biasing abutment (2008) and urges tapered biasing abutment (2008) into cartridge body (2002) until clear of the proximal movement of cage (2004).

Figure 41:
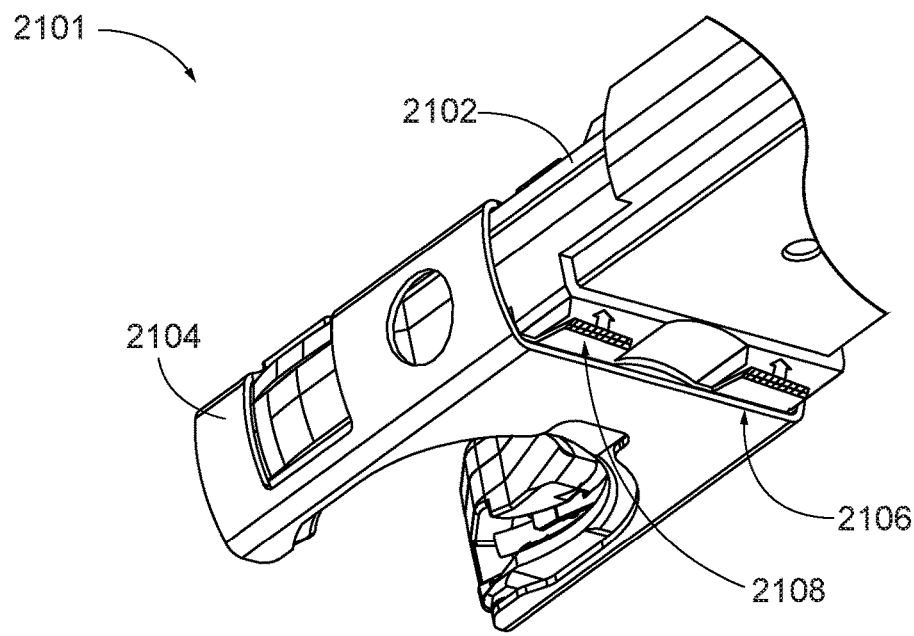
FIG. 41 depicts an enlarged bottom view of an exemplary cartridge configured for receipt in the cartridge receiving assembly of FIG. 2A, with a fifth exemplary tab cage securement.

As further seen in FIG. 41, a fifth exemplary tab cage securement (2106) has a plurality of tapered biasing abutments (2108) resiliently mounted within a cartridge (2101). It should be understood that cartridge (2101) of this example may be configured and operable just like cartridge (30) described above, except for the differences explicitly noted herein. Each tapered biasing abutment (2108) operates substantially similar to tapered biasing abutment (2008) (see FIG. 40) discussed above, but with respective tapers in opposite proximal and distal directions. To this end, any number of such biasing elements (2108) may be so used.

J. Tapered Cage Securement

Figure 42:
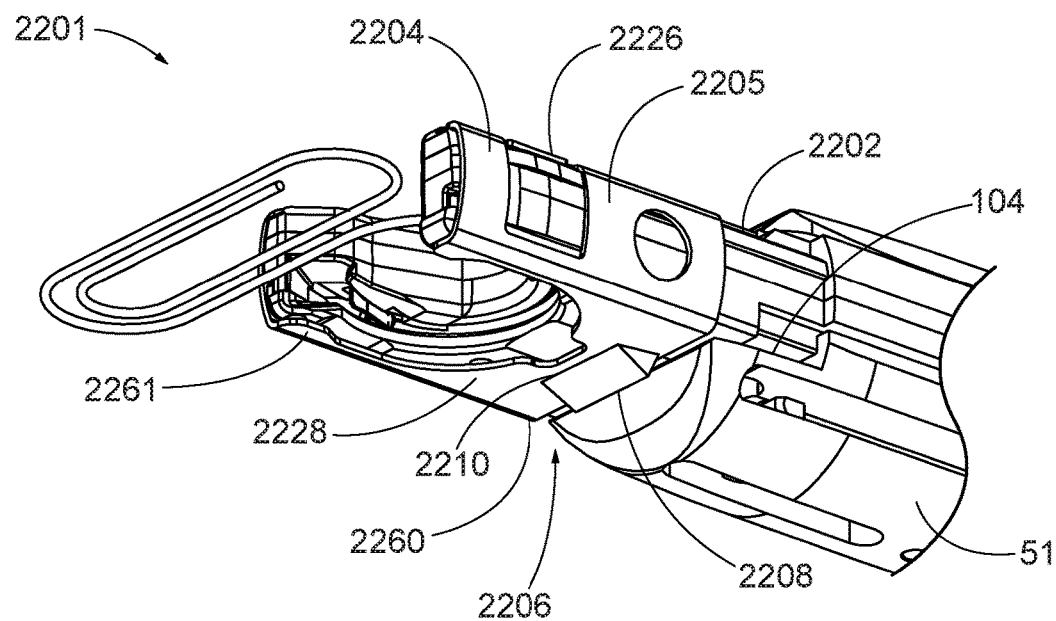
FIG. 42 depicts an enlarged bottom view of an exemplary cartridge configured for receipt in the cartridge receiving assembly of FIG. 2A, with an exemplary tapered cage securement.

FIG. 42 illustrates a cartridge (2201) with an exemplary tapered cage securement (2206) including a flap abutment (2208) projecting from a cage (2204). It should be understood that cartridge (2201) of this example may be configured and operable just like cartridge (30) described above, except for the differences explicitly noted herein. Tapered cage securement (2206) is sized and shaped to associate flap abutment (2208) of cage (2204) with a deflector (2210) located on a proximal end portion (2260) of cage (2204) to provide resistance of cage (2204) against lower jaw (51) and inhibit movement of cage (2204) from the closed position to the opened position. Upon manipulation of flap abutment (2208) by the operator toward cartridge (2201), flap abutment (2208) recedes to transversely clear lower jaw (51) with deflector (2210) deflecting inwardly. Now parallel with proximal end portion (2260), flap abutment (2208) is configured to slidably translate with cage (2204) from the closed position toward the opened position through elongate slot (104).

In the present example, flap abutment (2208) of tapered cage securement (2206) is tapered and positioned along a lower surface (2228) of cage (2204) along proximal end portion (2260). Flap abutment (2208) extends laterally along the substantial length of proximal end portion (2260) of cage (2204), and deflector (2210) extends similarly along proximal end portion (2260) of lower surface (2228) to contact lower jaw (51). In the present example, flap abutment (2208) and deflector (2210) of tapered cage securement (2206) are integrally and unitarily formed. However, it should be understood that in other examples each may comprise separately formed features of varying sizes, shapes, and/or lengths. In another example, tapered cage securement (2206) may be positioned along an upper surface (2226) of cage (2204) or along a sidewall (2205) of cage (2204). Tapered cage securement (2206) of cage (2204) is made from a material that is similar to the material from which cage (2204) is made. However, it should be understood that tapered cage securement (2206) may be made from various materials that resiliently and/or plastically deflect flap abutment (2208). Flap abutment (2208) is configured to resiliently engage lower jaw (51) and substantially retain cage (2204) in the closed position. Upon inwardly exertion by an operator onto tapered cage securement (2206) to overcome the resilient bias, flap abutment (2208) and deflector (2210) deflect inwardly to thereby allow cage (2204) to slidably translate from the closed position to the opened position.

K. Resilient Stub Cage Securement

Figure 43:
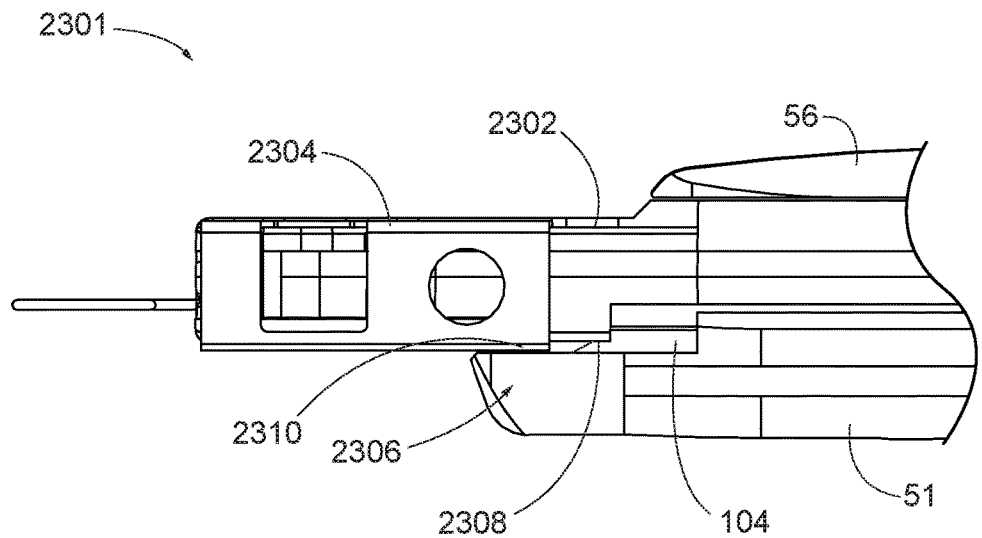
FIG. 43 depicts an enlarged side view of an exemplary cartridge receiving assembly that may be incorporated into the instrument of FIG. 1, with an exemplary cartridge and a first exemplary resilient stub cage securement.
Figure 44:
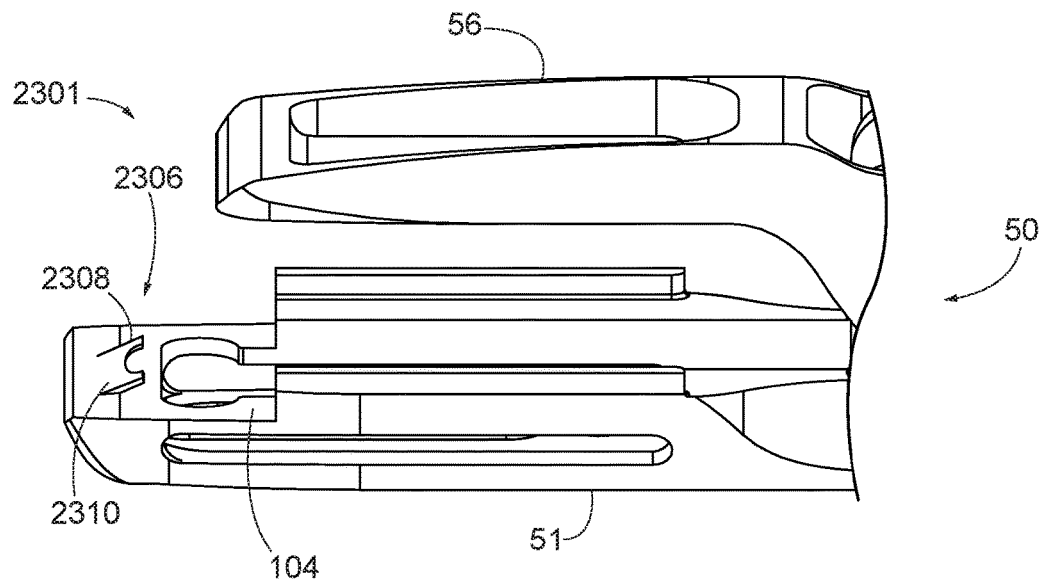
FIG. 44 depicts an enlarged top perspective view of the cartridge receiving assembly of FIG. 43.

FIGS. 43-44 illustrate a cartridge (2301) with a first exemplary resilient stub cage securement (2306) formed by a stub abutment (2308) projecting from lower jaw. It should be understood that cartridge (2301) of this example may be configured and operable just like cartridge (30) described above, except for the differences explicitly noted herein. Resilient stub cage securement (2306) is sized and shaped to associate stub abutment (2308) of cartridge receiving assembly (50) with a deflector (2310). More particularly, deflector (2310) extends between lower jaw (51) and stub abutment (2308) such that deflector (2310) and stub abutment (2308) are integrally and unitarily connected. Thereby stub abutment (2308) engages a cage (2304) to provide resistance of cage (2304) against cartridge receiving assembly (50) and inhibit movement of cage (2304) from the closed position. Upon exertion by the operator of the predetermined opening force greater than that amount of resistance generated by resilient stub cage securement (2306), cage (2304) urges stub abutment (2308) toward lower jaw (51), which causes deflector (2310) to deflect and allows cage (2304) to slidably translate away from the closed position and toward the opened position into through elongate slot (104). In the present example, stub abutment (2308) of resilient stub cage securement (2306) extends proximally and upwardly from lower jaw (51) to engage a cartridge body (2302) adjacent to a proximal end portion (2360) of cage (2304).

Figure 45:
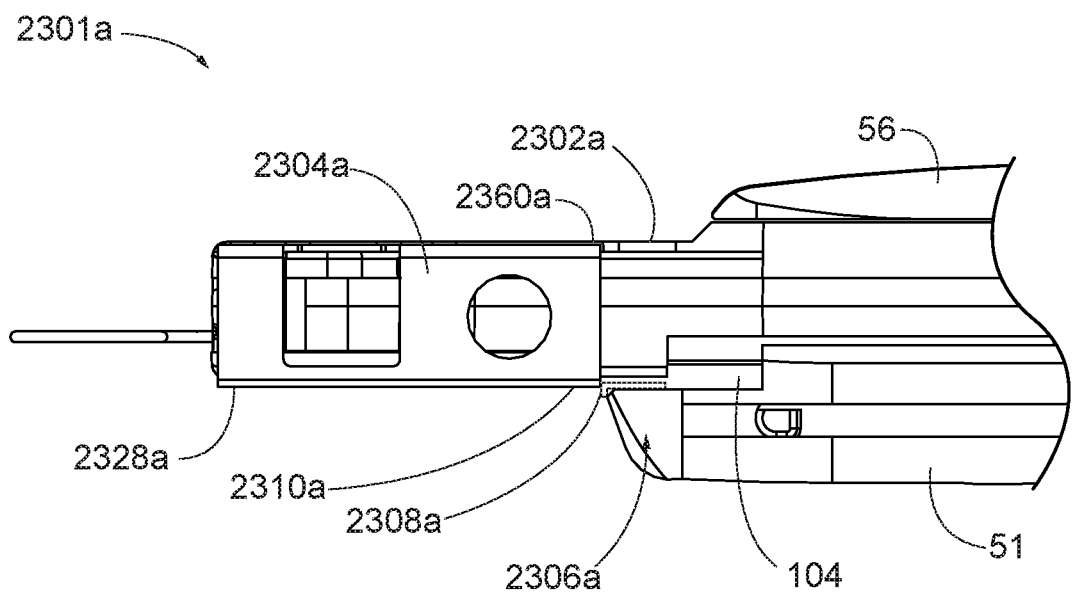
FIG. 45 depicts an enlarged side view of an exemplary cartridge receiving assembly that may be incorporated into the instrument of FIG. 1, with an exemplary cartridge and a second exemplary resilient stub cage securement.

FIG. 45 shows a cartridge (2301a) with a second exemplary resilient stub cage securement (2306a) formed by a stub abutment (2308a) that extends at an angle parallel to lower jaw (51) of cartridge receiving assembly (50). It should be understood that cartridge (2301a) of this example may be configured and operable just like cartridge (30) described above, except for the differences explicitly noted herein. In the present example, stub abutment (2308a) is configured to resiliently engage a proximal end portion (2360a) of a lower surface (2328a) and substantially retain cage (2304a) in the closed position. Upon exertion by an operator of the predetermined opening force to overcome the resilient bias, a deflector (2310a) extending along proximal end portion (2360a) deflects inwardly toward a cartridge body (2302a) to thereby allow cage (2304a) to slidably translate from the closed position toward the opened position.

Figure 46:
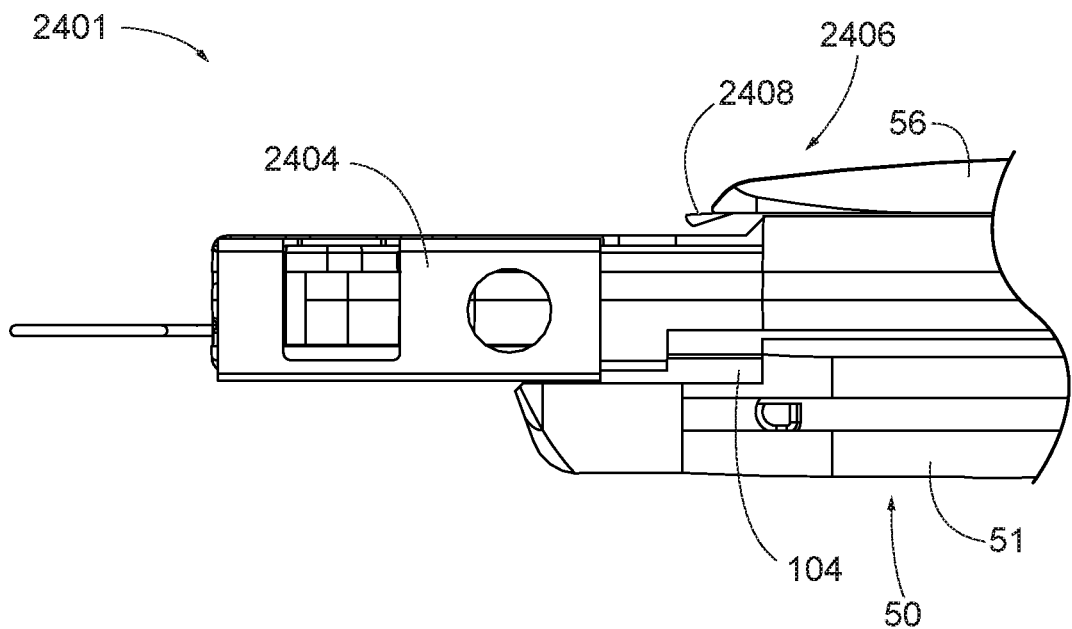
FIG. 46 depicts an enlarged side view of an exemplary cartridge receiving assembly that may be incorporated into the instrument of FIG. 1, with an exemplary cartridge and a third exemplary resilient stub cage securement.
Figure 47:
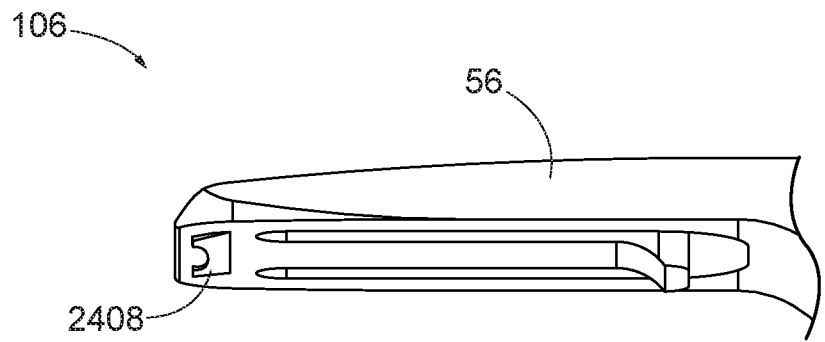
FIG. 47 depicts an enlarged top perspective view of the cartridge receiving assembly of FIG. 46.

FIGS. 46-47 show a cartridge (2401) and a third exemplary resilient stub cage securement (2406) formed by a stub abutment (2408) extending from upper jaw (56) of cartridge receiving assembly (50). Similar to stub abutment (2306)

(see FIG. 43) discussed above, stub abutment (2406) is configured to engage a cage (2404) and inhibit movement thereof up to the predetermined opening force. Resilient stub cage securement (2406) of cartridge receiving assembly (50) is made from a material that is similar to the material from which cartridge receiving assembly (50) is made. However, it should be understood that resilient stub cage securement (2406) may be made from various materials that resiliently and/or plastically deflect against cage (2404). Other various materials for resilient stub cage securement (2406) may be provided as will be apparent to those of ordinary skill in the art in view of the teachings herein.

L. Detent Cage Securement

Figure 48:
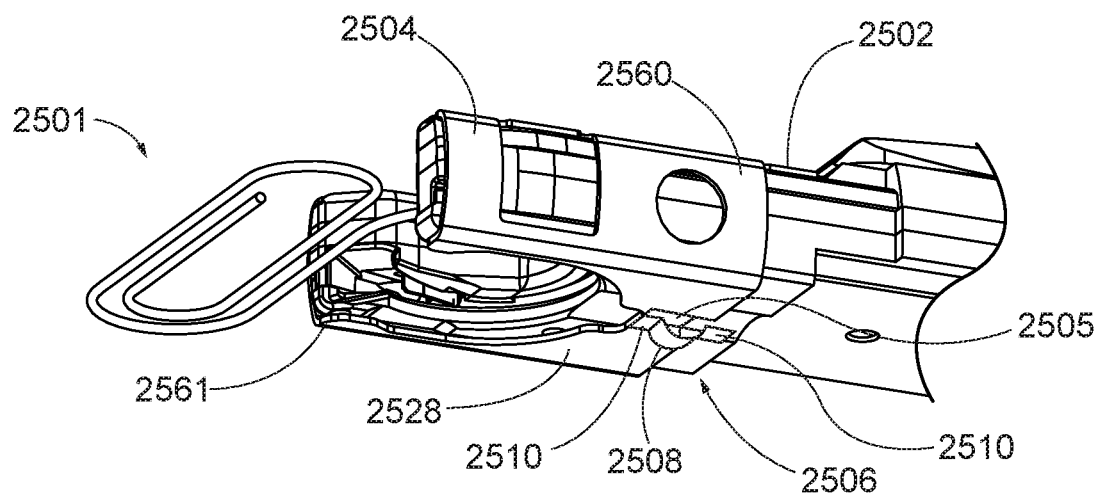
FIG. 48 depicts an enlarged bottom perspective view of an exemplary cartridge configured for receipt in the cartridge receiving assembly of FIG. 2A, with an exemplary detent cage securement.
Figure 49:
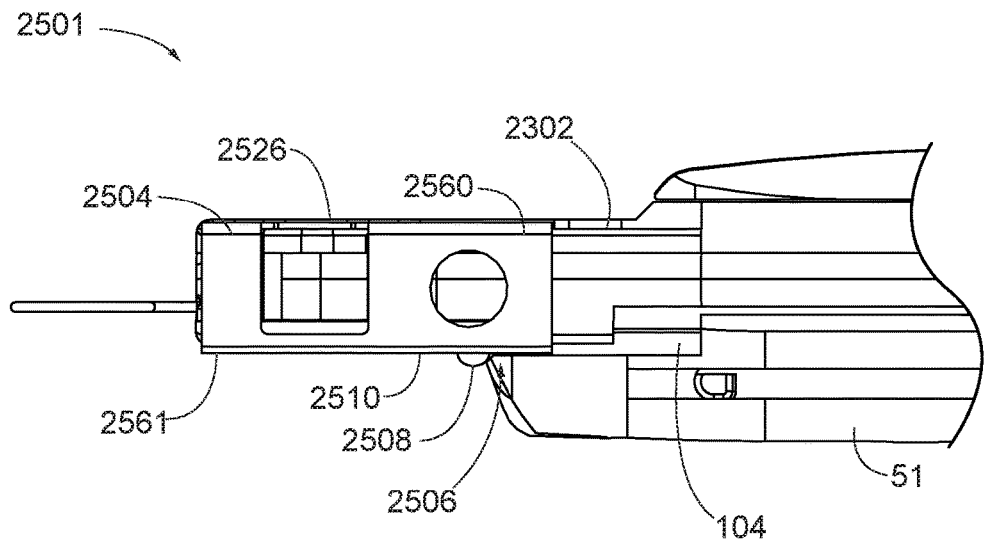
FIG. 49 depicts an enlarged side view of the cartridge of FIG. 48.

FIGS. 48-49 illustrate a cartridge (2501) with an exemplary detent cage securement (2506) having a detent abutment (2508) projecting from a proximal end portion (2560) of a cage (2504). It should be understood that cartridge (2501) of this example may be configured and operable just like cartridge (30) described above, except for the differences explicitly noted herein. Detent cage securement (2506) is sized and shaped to associate detent abutment (2508) of cage (2504) with a deflector (2510) extending from cage (2504) to provide resistance of cage (2504) against cartridge receiving assembly (50) and inhibit movement of cage (2504) from the closed position to the opened position. Upon exertion by the operator of the predetermined opening force greater than that amount of resistance generated by detent cage securement (2506), detent abutment (2508) causes deflector (2510) to deflect inward toward a cartridge body (2502) until clearing lower jaw (51). Cage (2504) is thus allowed to slidably translate away from the closed position and toward the opened position through elongate slot (104).

As best seen in FIG. 48, the present example includes detent abutment (2508) of detent cage securement (2506) on a lower surface (2528) of cage (2504). Detent abutment (2508) is resiliently attached to cage (2504) by deflector (2510) in the form of extending ledges. More particularly, cage (2504), detent abutment (2508), and deflector (2510) are integrally and unitarily formed. Cage (2504) includes a recessed portion (2505) along proximal end portion (2560) to allow space for deflector (2510) to deflect inwardly toward cartridge body (2502) when cage (2504) is urged in the proximal direction. Detent abutment (2508) is configured to resiliently engage lower jaw (51) of cartridge receiving assembly (50) and substantially retain cage (2504) in the closed position. Upon exertion by the operator of the predetermined opening force to overcome the resilient bias, detent abutment (2508) and deflector (2510) deflect upwardly into recessed portion (2505) and laterally to thereby allow cage (2504) to slidably translate from the closed position to the opened position. In another example not shown, detent cage securement (2506) may be positioned along an upper surface (2526) of cage (2504). By way of further example, an alternative detent cage securement may have a plurality of detent abutments (2508) and respective deflectors (2510) on cage (2504). Detent cage securement (2506) of cage (2504) is made from a material that is similar to the material from which cage (2504) is made. However, it should be understood that detent cage securement (2506) may be made from various materials that resiliently and/or plastically deflect detent abutment (2508).

M. Bumper Cage Securement

Figure 50A:
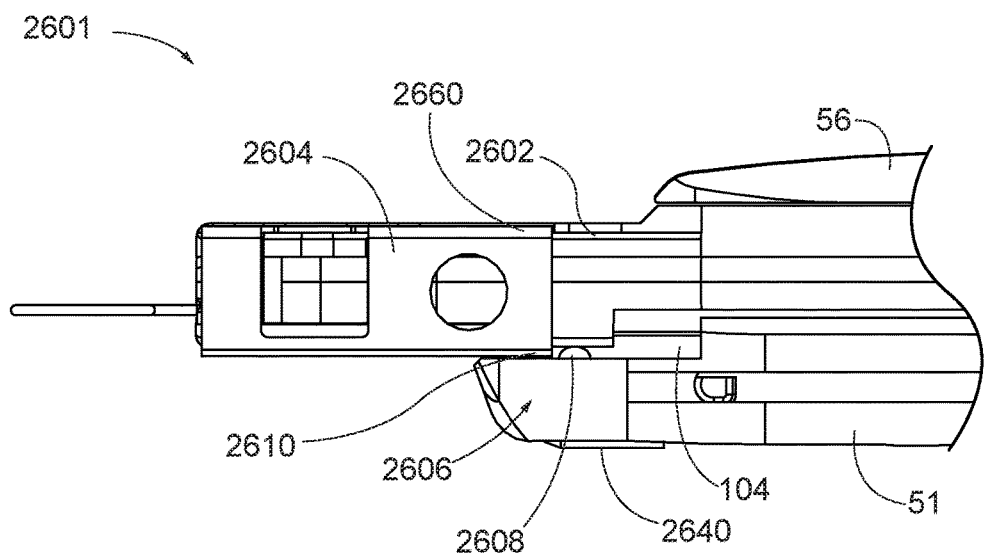
FIG. 50A depicts an enlarged side view of an exemplary cartridge configured for receipt in the cartridge receiving assembly of FIG. 2A, with an exemplary bumper cage securement.
Figure 50B:
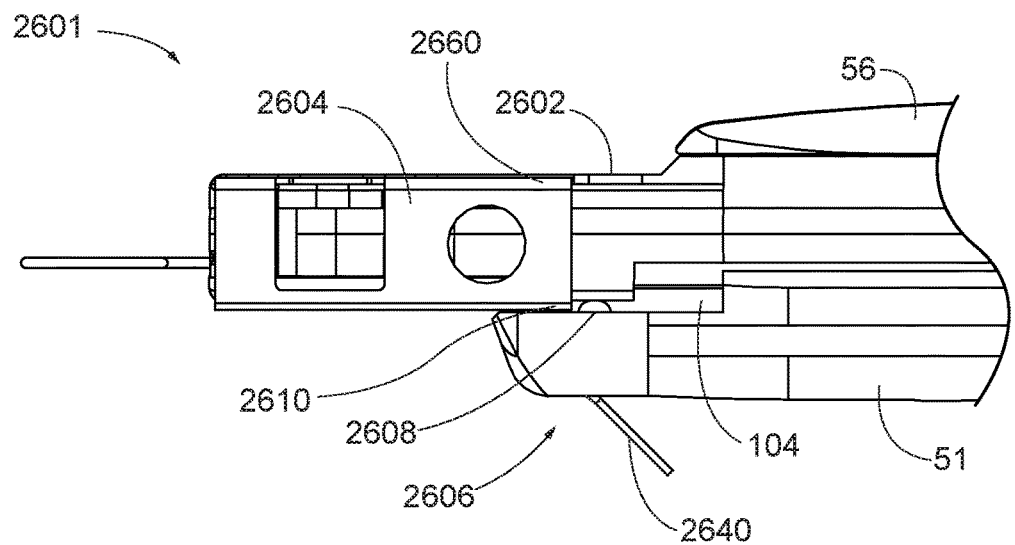
FIG. 50B depicts an enlarged side view of the exemplary cartridge of FIG. 50A, with a blocking member in a blocking position.
Figure 50C:
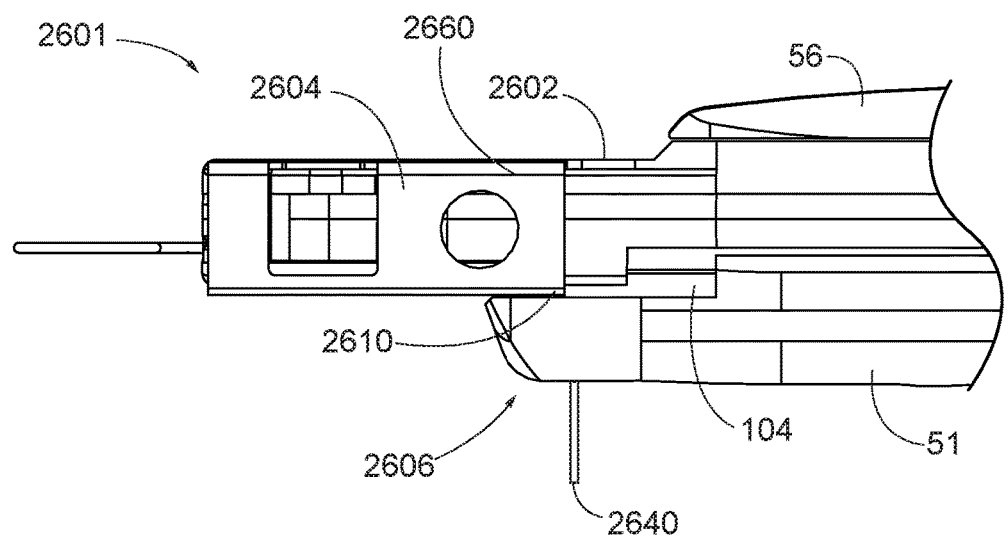
FIG. 50C depicts an enlarged side view of the exemplary cartridge of FIG. 50A, with a blocking member in an unblocking position.
Figure 51:
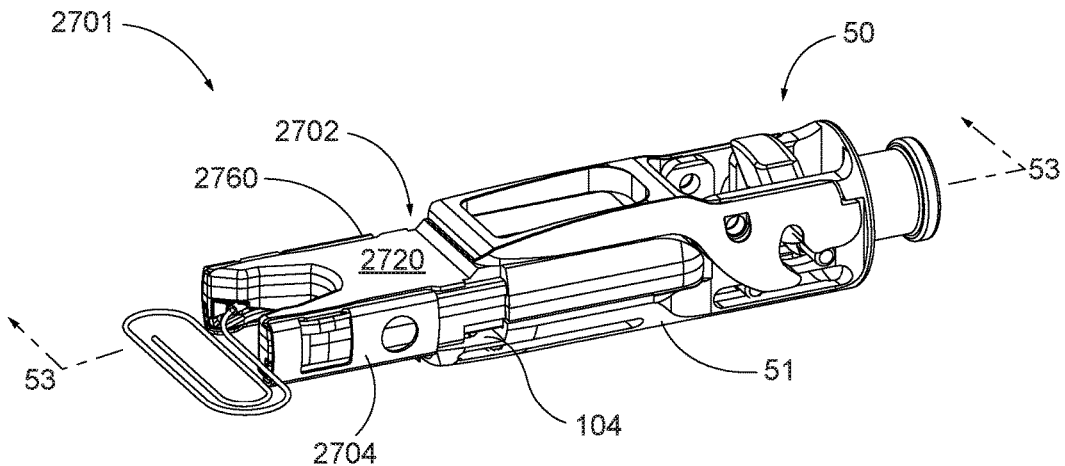
FIG. 51 depicts a top perspective view of an exemplary cartridge receiving assembly that may be incorporated into the instrument of FIG. 1, with an exemplary cartridge and an exemplary ball-detented cage securement.
Figure 52:
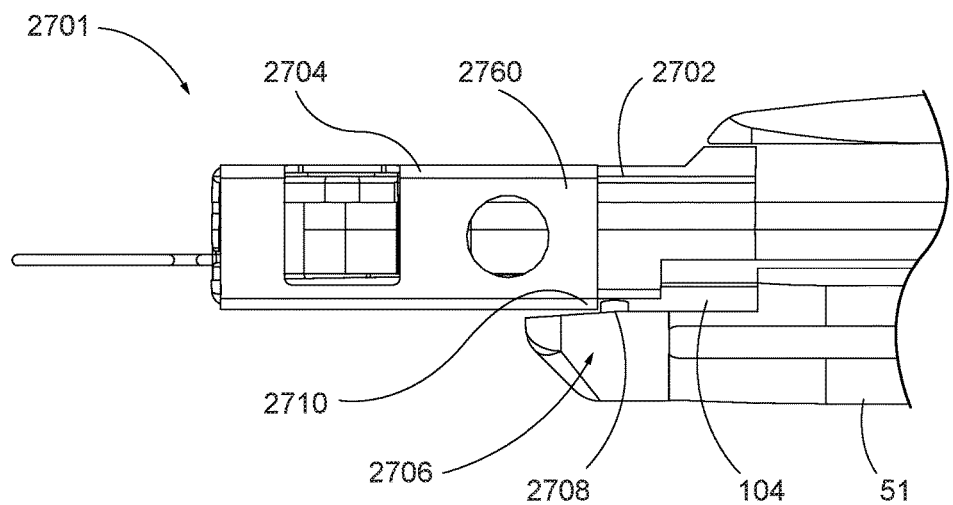
FIG. 52 depicts an enlarged side view of the cartridge receiving assembly and cartridge of FIG. 51.

FIGS. 50A-50C illustrate a cartridge (2601) with an exemplary bumper cage securement (2606) having a bumper blocker (2608) removably secured against a cage (2604) of cartridge (2601). It should be understood that cartridge (2601) of this example may be configured and operable just like cartridge (30) described above, except for the differences explicitly noted herein. Bumper blocker (2608) of bumper cage securement (2606) is sized and shaped to associate cage (2604) to provide resistance against cage (2604) and inhibit movement of cage (2604) from the closed position toward the opened position through elongate slot (104). Bumper blocker (2608) is configured to be selectively moved from an upper position to a lower position within lower jaw (51) by manipulation of a switch (2640). With bumper blocker (2608) in the lower position, cage (2604) may be freely manipulated by the operator from the closed position toward the opened position.

Switch (2640) extends from a lower portion of lower jaw (51) and is operatively connected to bumper blocker (2608) for selective movement of bumper blocker (2608). With switch (2640) in a position against lower jaw (51) as shown in FIG. 50A, bumper blocker (2608) remains in the upper position to effectively block proximal movement of cage (2604). However, manipulating switch (2640) as shown in FIGS. 50B-50C lowers bumper blocker (2608) to recede into lower jaw (51) and clear elongate slot (104). Cage (2604) may than be urged toward the opened position by the operator.

Tab blocker (3008) extends transversely and outwardly from cavity (3003) between cartridge body (3002) and cage (3004) along lower jaw (51) for ease of access by the operator. More particularly, the operator may grasp the extending bottom portion (3011) of tab blocker (3008) and remove it from between cartridge (3001) and cage (3004). Extraction of tab blocker (3008) essentially unblocks proximal movement of cage (3004) and allows cage (3004) to translate proximally to the opened position through elongate slot (104). By way of example, it may be desirable to include a plurality of tab blockers (3008) at varying locations along cage (3004). In some versions, tab blocker (3008) of tab removal cage securement (3006) is made from a plastic material. However, it should be understood that tab removal cage securement (3006) may be made from various materials that block proximal movement of cage (3004). Although not shown, it should be understood that bumper cage securement (2606) may comprise bumper abutment (2608) extending from upper jaw (56) of cartridge receiving assembly (50). Alternatively, it may be desirable to position switch (2640) on upper jaw (56) and/or include a shape or size of lever (2640) that varies in comparison to that depicted in the exemplary version to allow the operator to access its functionality.

N. Ball-Detened Cage Securement

FIGS. 51-53B illustrates a cartridge (2701) having an exemplary ball-detented cage securement (2706) that comprises a movable abutment (2708) projecting from a lower jaw (51) of a cartridge receiving assembly (50). Ball-detented cage securement (2706) is sized and shaped to associate movable abutment (2708) of cartridge receiving assembly (50) with a cage (2704) to provide resistance against cage (2704) and inhibit movement of cage (2704) from the closed position toward the opened position. Upon exertion by the operator of the predetermined opening force greater than that amount of resistance generated by ball-detented cage securement (2706), movable abutment (2708) is configured to pivot and retract into lower jaw (51) and clear of cage (2704). Cage (2704) is thus allowed to slidably translate from the closed position toward the opened position through elongate slot (104).

Figure 53A:
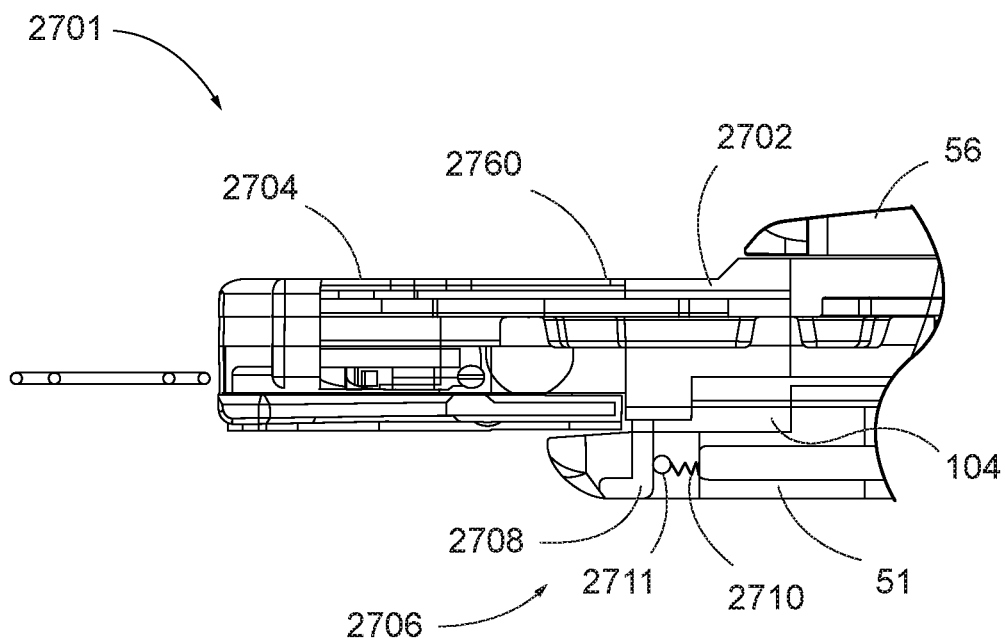
FIG. 53A depicts a cross-sectional view of the cartridge receiving assembly and the cartridge of FIG. 51, taken along section line 53-53 of FIG. 51, with the ball-detented cage securement in a closed position.
Figure 53B:
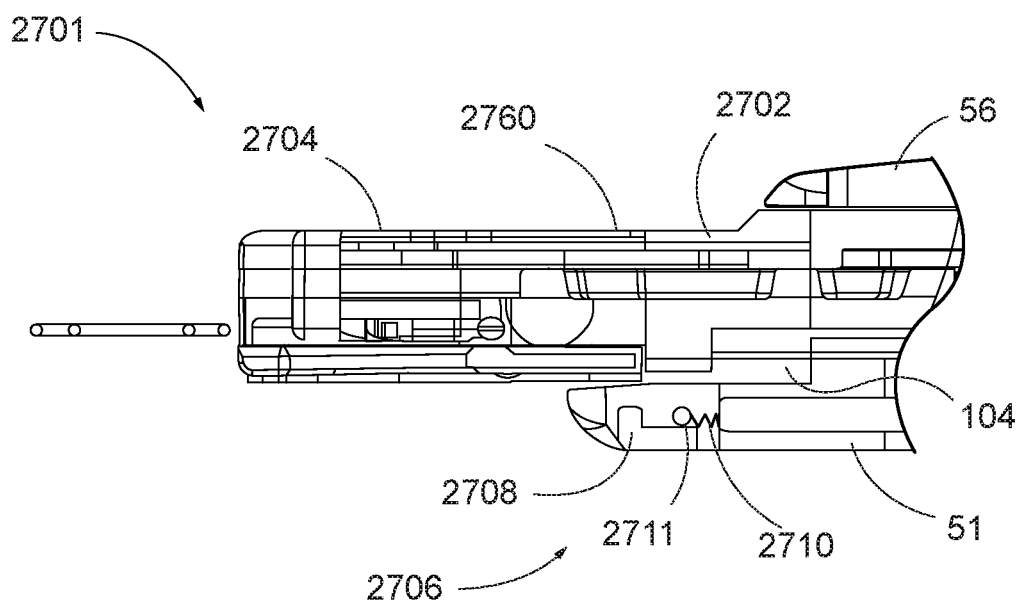
FIG. 53B depicts a cross-sectional view of the cartridge receiving assembly and the cartridge of FIG. 51, taken along section line 53-53 of FIG. 51, with the ball-detented cage securement in an opened position.

As best seen in FIG. 53A-53B, movable abutment (2708) is pivotally mounted to move between an upward position for engagement with cage (2704) and a retracted position for clearance from cage (2704). Ball-detented cage securement (2706) further includes a resiliently mounted detent ball (2711), which is more particularly mounted with a resilient deflector (2710) in the form of a spring to lower jaw (51). Resilient deflector (2710) urges detent ball (2711) against movable abutment (2708) in the upward position. Moveable abutment (2708) is configured to resiliently engage detent ball (2711) and substantially retain cage (2704) in the closed position. Upon the exertion by an operator of the predetermined opening force to overcome the resilient bias, through either the use of a tool or the proximal movement of cage (2704), moveable abutment (2708) is retracted into lower jaw (51) to thereby allow cage (2704) to slidably translate from the closed position to the opened position. Although not shown, it should be understood that ball-detented cage securement (2706) may comprise movable abutment (2708) extending from upper jaw (56) of cartridge receiving assembly (50). Upon retraction of movable abutment (2708) from deflector (2710), cage (2704) may be positioned proximally through elongate slot (104) to the opened position.

O. Pivot Pin Cage Securement

Figure 54A:
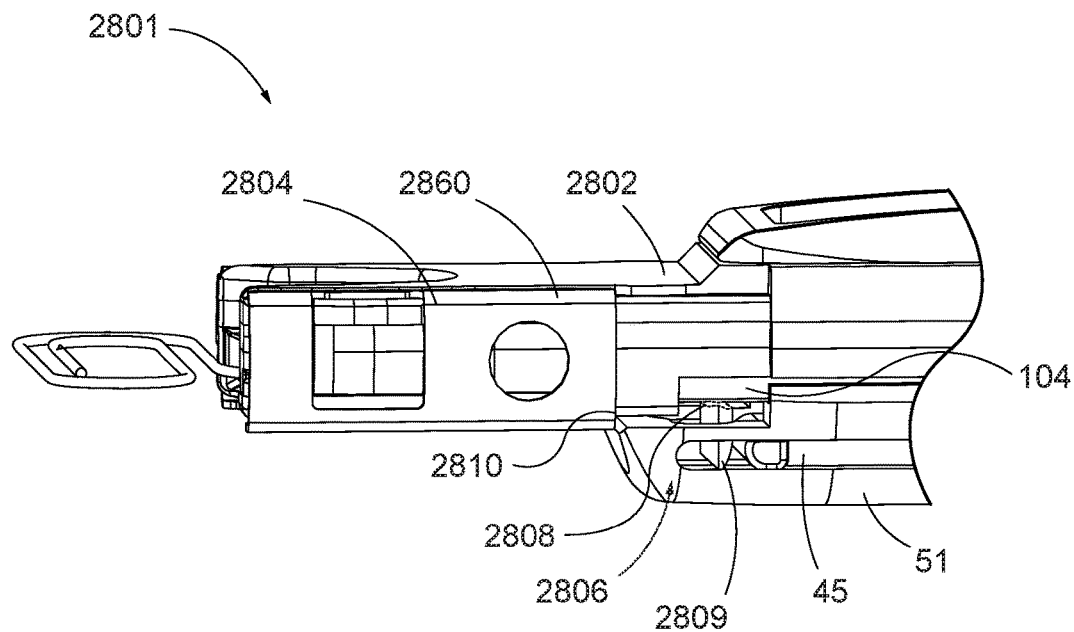
FIG. 54A depicts a top perspective view of an exemplary cartridge receiving assembly that may be incorporated into the instrument of FIG. 1, with an exemplary cartridge and an exemplary pivot pin cage securement in a blocking position.
Figure 54B:
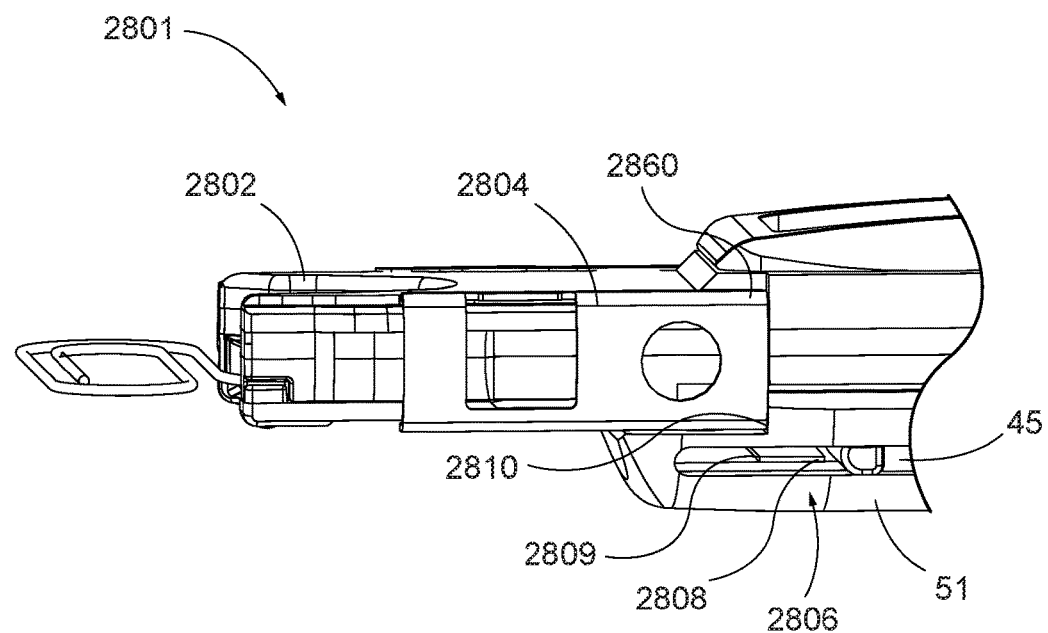
FIG. 54B depicts a top perspective view of the cartridge receiving assembly and the cartridge of FIG. 54A, with the pivot pin cage securement in an unblocking position.

FIGS. 54A-54B illustrate a cartridge (2801) and exemplary pivot pin cage securement (2806) that has a pin abutment (2808) projecting from lower jaw (51) of cartridge receiving assembly (50). Pin abutment (2808) is pivotally mounted in lower jaw (51) and associated with a cage (2804) to provide resistance against cage (2804) and inhibit movement of cage (2804) from the closed position toward the opened position. When rack (45) is in a distal position, a distal end portion of rack (45) engages pin abutment (2808) to hold pin abutment (2808) against cage (2804) in the closed position. Upon retraction of rack (45) by the operator in the proximal direction, rack disengages from pin abutment (2808) such that proximal movement of cage (2804) urges pivot abutment (2808) to pivot downwardly about a pivot point (2809). Pin abutment (2809) thereby retracts inward into lower jaw (51) to allow cage (2804) to slidably translate away from the closed position toward the opened position through elongate slot (104).

In the present example, pin abutment (2808) of pivot pin cage securement (2806) extends from lower jaw (51) of cartridge receiving assembly (50) into elongate slot (104) and is rotatable around a pivot point (2809) positioned within lower jaw (51) of cartridge receiving assembly (50). Upon retraction of pin abutment (2808) from contact with cage (2804), cage (2804) may be positioned proximally toward elongate slot (104) to allow the operator to access needle cover (83) (see FIG. 5) in order to remove needle (70) (see FIG. 5) from a cartridge body (2802). Although the present example includes one pin abutment (2808) on lower jaw (51) of cartridge receiving assembly (50), it should be understood that multiple pivot abutments (2808) may be provided along lower jaw (51).

P. Rib Cage Securement

Figure 55:
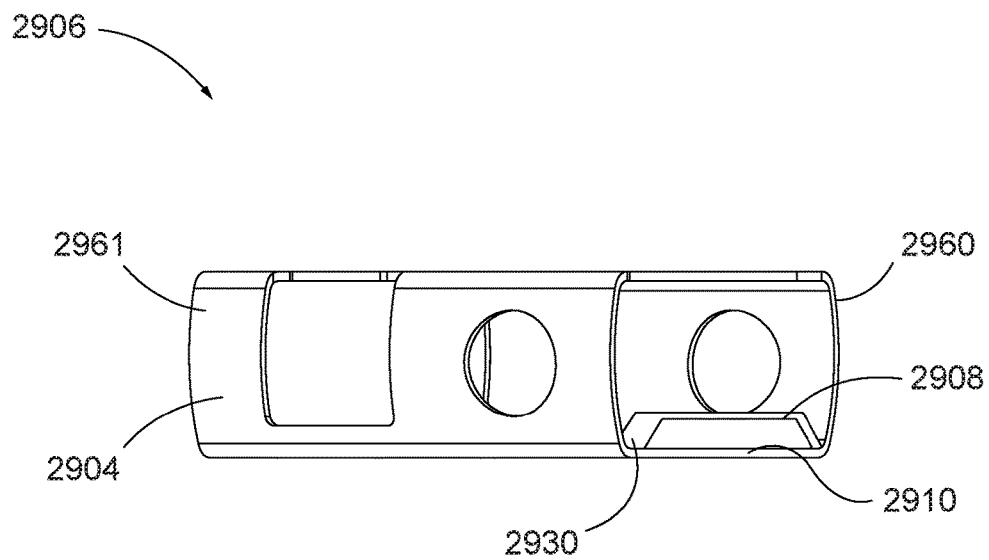
FIG. 55 depicts a side perspective view of an exemplary cage that may be incorporated into the cartridge of FIG. 3, with an exemplary rib cage securement.
Figure 56:
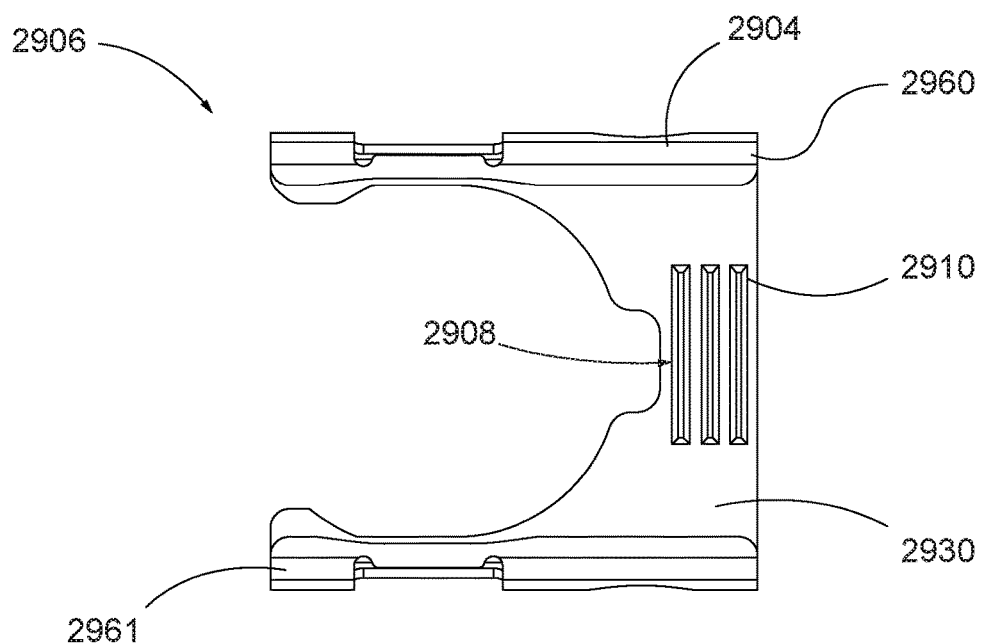
FIG. 56 depicts a bottom view of the portion of the cage of FIG. 55.
Figure 57:
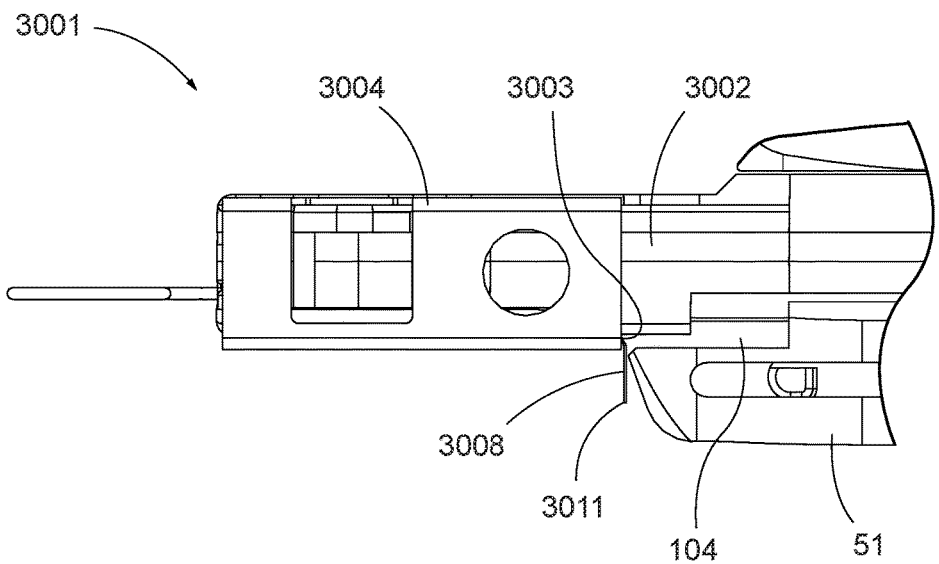
FIG. 57 depicts an enlarged side view of an exemplary cartridge receiving assembly that may be incorporated into the instrument of FIG. 1, with an exemplary cartridge and an exemplary removable tab cage securement.
Figure 58A:
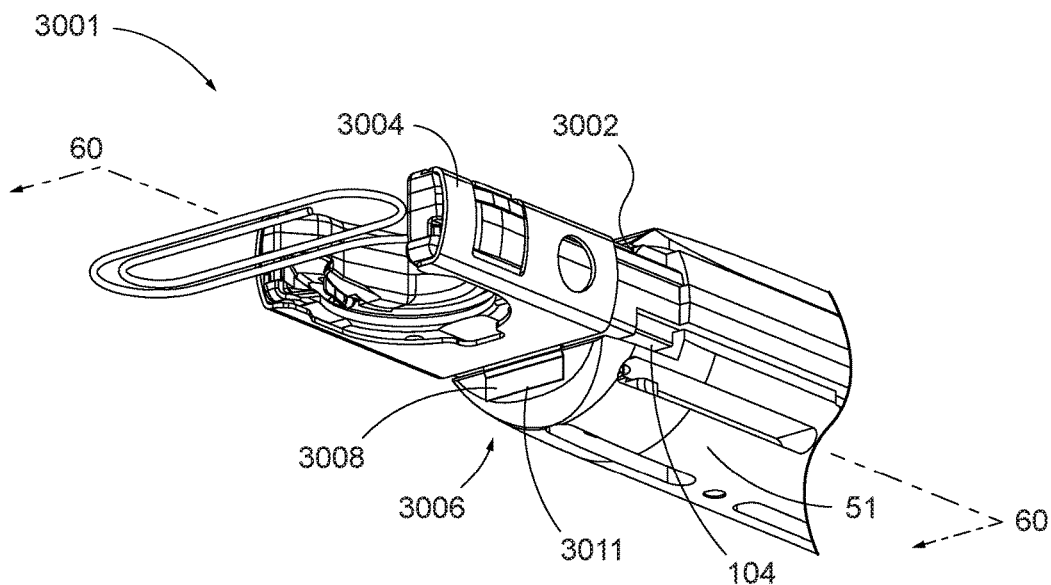
FIG. 58A depicts an enlarged bottom perspective view of the cartridge receiving assembly, the cartridge, and the removable tab of FIG. 57, with the removable tab secured to the cartridge receiving assembly, and with a cage of the cartridge in a closed position.
Figure 58B:
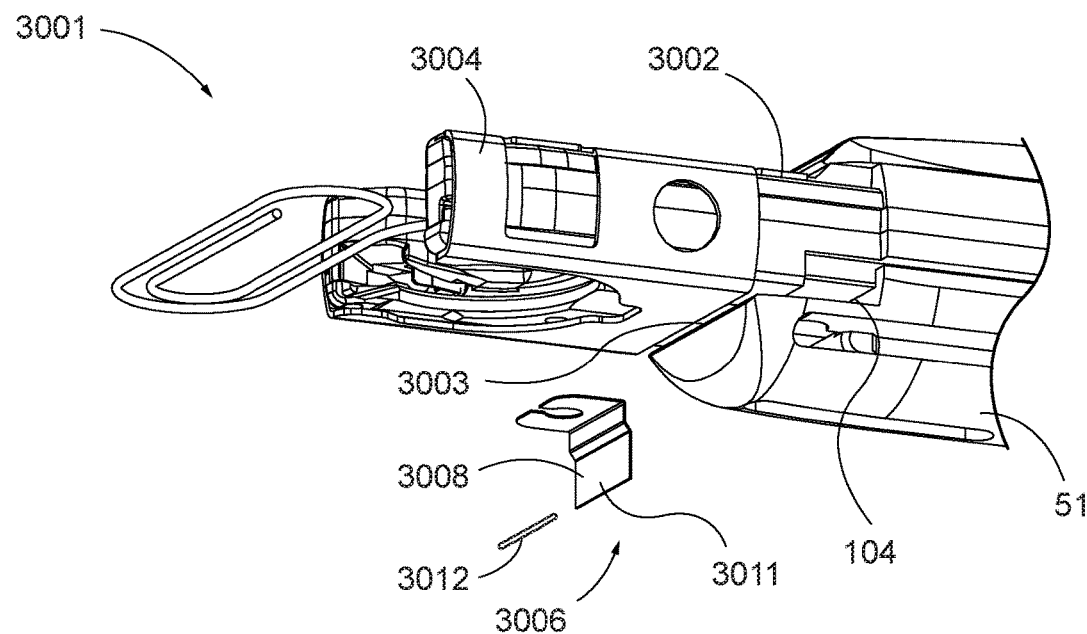
FIG. 58B depicts an enlarged bottom perspective view of the cartridge receiving assembly, the cartridge, and the removable tab of FIG. 57, with the removable tab removed from the cartridge receiving assembly, and with the cage in the closed position.
Figure 58C:
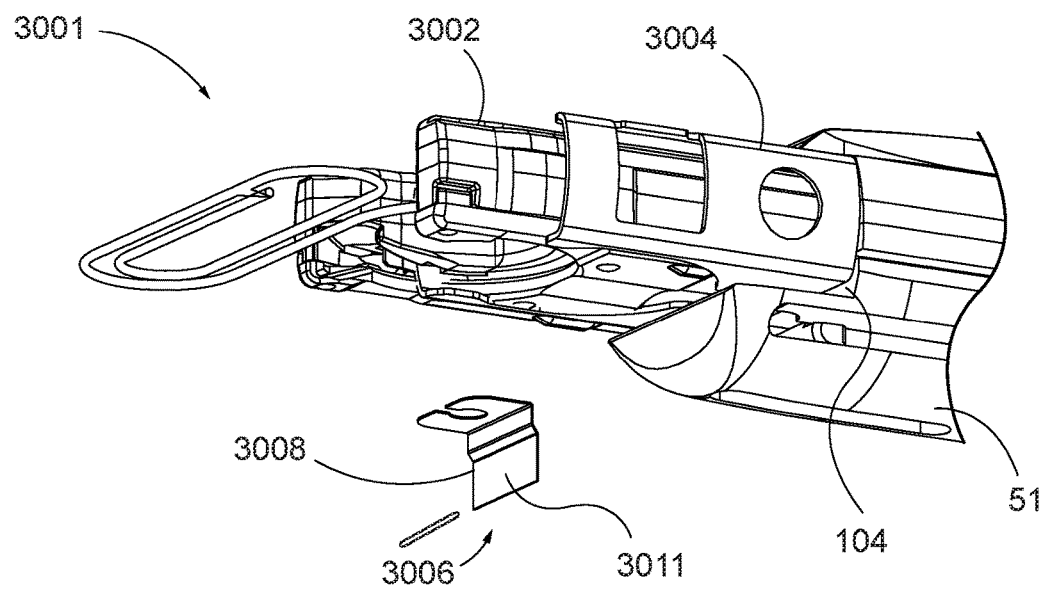
FIG. 58C depicts an enlarged bottom perspective view of the cartridge receiving assembly, the cartridge, and the removable tab of FIG. 57, with the removable tab removed from the cartridge receiving assembly, and with the cage in an open position.

FIGS. 55-56 illustrate an exemplary rib cage securement (2906) on a cage (2904). Similar to cage (2504) that includes abutment (2508) positioned along proximal end portion (2560) (see FIG. 49), cage (2904) includes a plurality of rib abutments (2908) adjacent a proximal end portion (2960) extending from an internal side (2930) of cage (2904) toward cartridge body (2502) (see FIG. 49). Rib cage securement (2906) is sized and shaped to associate each rib abutment (2908) of cage (2904) with a deflector (2910) positioned on internal side (2930) of cage (2904), from which each rib abutment (2908) extends. Each rib abutment (2908) is configured to engage cartridge body (2502) (see FIG. 49) and provide resistance of cage (2904) against cartridge body (2502) (see FIG. 49) to inhibit movement of cage (2904) from the closed position to the opened position. Upon exertion by the operator of the predetermined opening force on cage (2904) greater than that amount of resistance generated by rib cage securement (2906), rib abutments (2908) deflect respectively with deflectors (2910). Cage (2904) is thus allowed to translate proximally from the closed position toward the opened position through elongate slot (104) (see FIG. 49).

As depicted in FIG. 55, the present example includes rib abutment (2908) that protrudes from internal surface (2940) of cage (2904) along a proximal end portion (2960) to contact a lower surface cartridge body (2502) (see FIG. 49). Although rib abutment (2908) and deflector (2910) of the present example are shown as being integrally and unitarily formed, other examples of such abutments and deflector may comprise separately formed features of varying sizes, shapes, and/or lengths. Rib cage securement (2906) is also integrally and unitarily formed with cage (2904). However, rib cage securement (2906) may alternatively be made from various materials that resiliently and/or plastically deflect. Rib abutment (2908) is configured to resiliently engage cartridge body (2502) and substantially retain cage (2904) in the closed position. Upon exertion by an operator of the predetermined opening force to overcome the resilient bias, deflector (2910) and rib abutment (2908) are deflected downwardly and laterally to thereby allow cage (2904) to slidably translate from the closed position to the opened position.

Q. Tab Removal Cage Securement

FIGS. 57-61 illustrate a cartridge (3001) with an exemplary tab removal cage securement (3006) with a tab blocker (3008) removably secured against a cage (3004) of cartridge (3001). It should be understood that cartridge (3001) of this example may be configured and operable just like cartridge (30) described above, except for the differences explicitly noted herein. Tab blocker (3008) of tab removal cage securement (3006) is sized and shaped to associate with a cavity (3003) in between a cartridge body (3002) and cage (3004) to provide resistance of cage (3004) against cartridge body (3002) and inhibit movement of cage (3004) from the closed position toward the opened position through elongate slot (104). Tab blocker (3008) is configured to be removed by the operator from cavity (3003) upon application of a transverse force. With tab blocker (3008) removed from cartridge (3001), cage (3004) may be freely manipulated by the operator for translation from the closed position toward the opened position.

Figure 59:
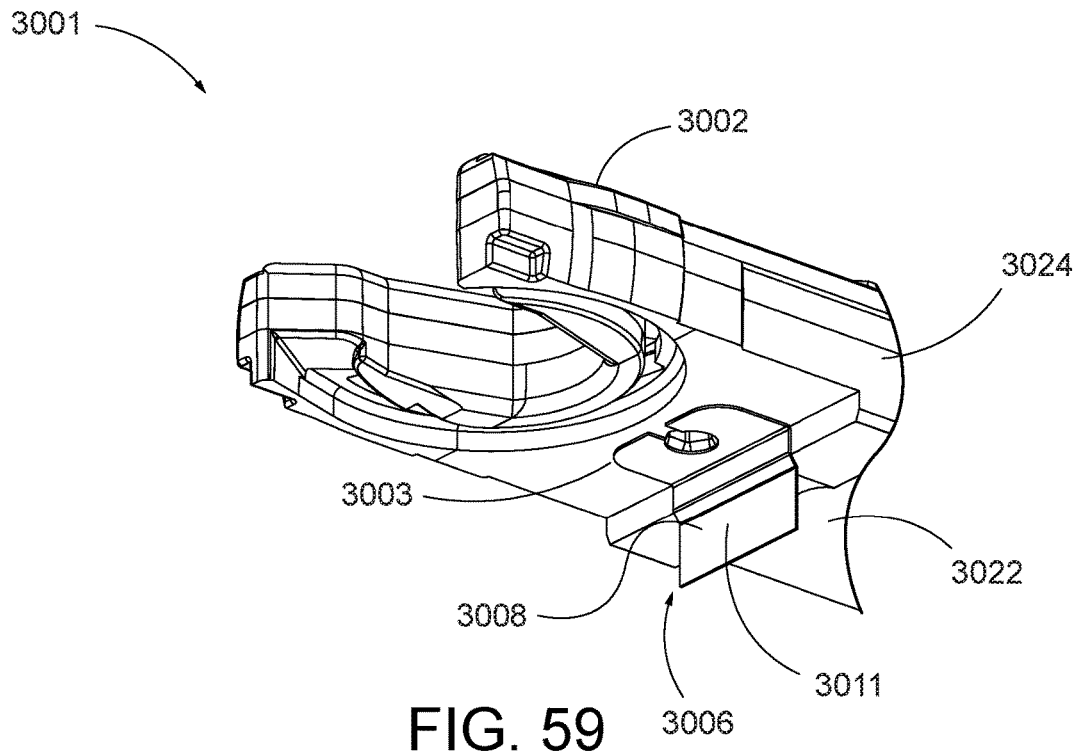
FIG. 59 depicts an enlarged bottom perspective view of the cartridge receiving assembly, the cartridge, and the removable tab of FIG. 57 having various features removed for improved clarity.
Figure 60:
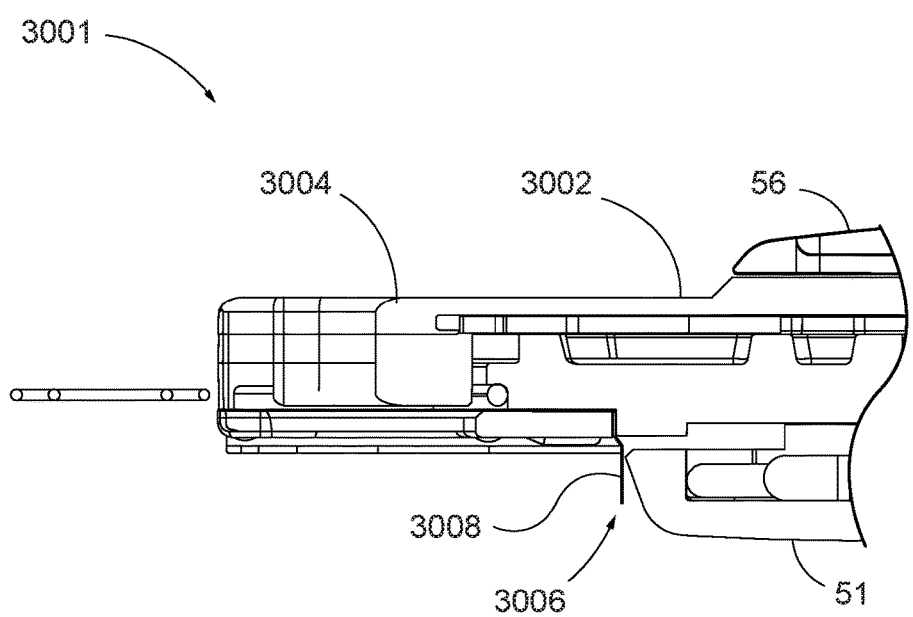
FIG. 60 depicts a cross-sectional view of the cartridge receiving assembly, the cartridge, and the removable tab of FIG. 57, taken along section line 60-60 of FIG. 58A.
Figure 61:
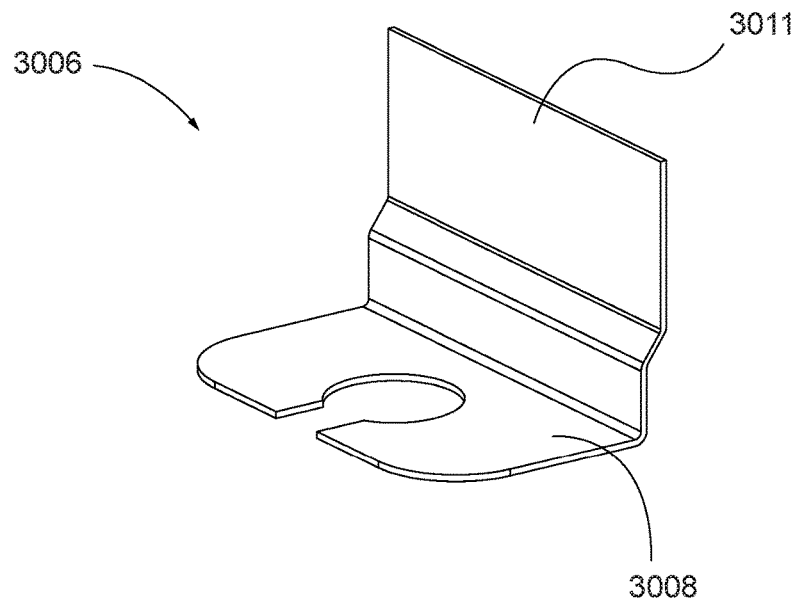
FIG. 61 depicts a perspective view of the removable tab of FIG. 57.

As shown in FIGS. 59-60, a bottom portion (3011) of tab blocker (3008) extends transversely and outwardly from cavity (3003) between cartridge body (3002) and cage (3004) along lower jaw (51) for ease of access by the operator. More particularly, the operator may grasp the extending bottom portion (3011) of tab blocker (3008) and remove it from between cartridge (3001) and cage (3004). Extraction of tab blocker (3008) essentially unblocks proximal movement of cage (3004) and allows cage (3004) to translate proximally to the opened position through elongate slot (104). By way of example, it may be desirable to include a plurality of tab blockers (3008) at varying locations along cage (3004). Tab blocker (3008) of tab removal cage securement (3006) is made from a plastic material. However, it should be understood that tab removal cage securement (3006) may be made from various materials that block proximal movement of cage (3004).

R. Tab Release Cage Securement

FIGS. 62A-65 illustrate a cartridge (3101) with an exemplary tab release cage securement (3106) with a shim tab blocker (3108) releasably secured against cartridge (3101). It should be understood that cartridge (3101) of this example may be configured and operable just like cartridge (30) described above, except for the differences explicitly noted herein. Shim tab blocker (3108) is sized and shaped to associate with a lower cavity (3103) in between a cartridge body (3102) and a cage (3104) to provide resistance of cage (3104) against cartridge body (3102) and inhibit movement of cage (3104) from the closed position toward the opened position. Shim tab blocker (3108) is configured to be pulled from a folded configuration between cartridge body (3102) and cage (3104), upon application of the transverse force, to release shim tab blocker (3108) from its frictionally secured position to an unfolded configuration. With shim tab blocker (3108) released from cartridge (3101), cage (3104) may be freely manipulated by the operator for slidable translation from the closed position toward the opened position.

Figure 62A:
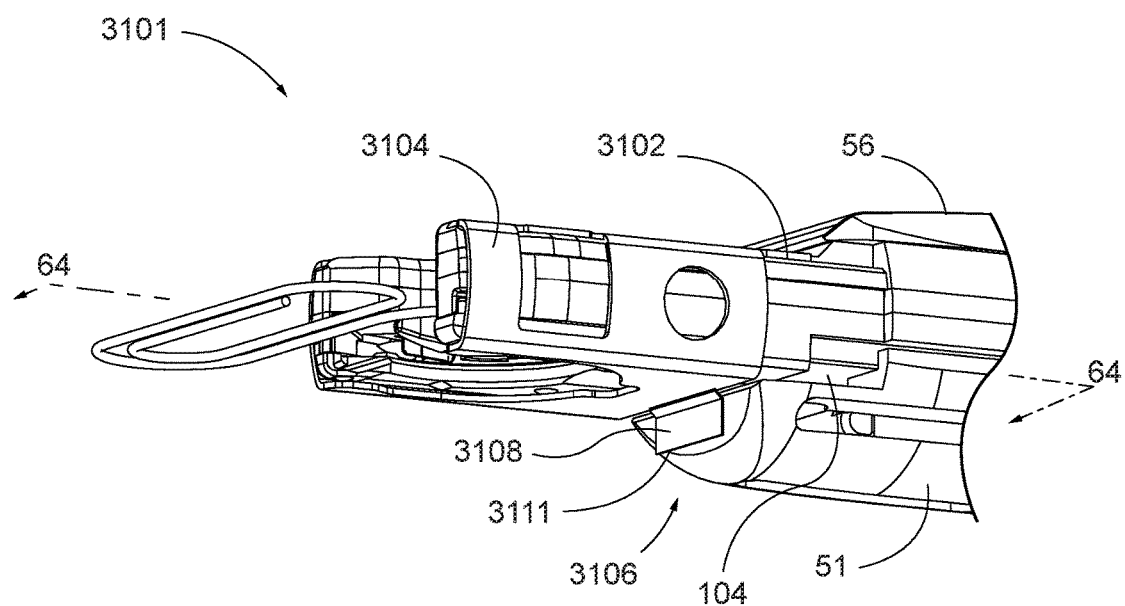
FIG. 62A depicts an enlarged bottom perspective view of an exemplary cartridge receiving assembly that may be incorporated into the instrument of FIG. 1, with an exemplary cartridge and an exemplary integral tab release cage securement, with a cage of the cartridge in a closed position and with the tab in a folded configuration.
Figure 62B:
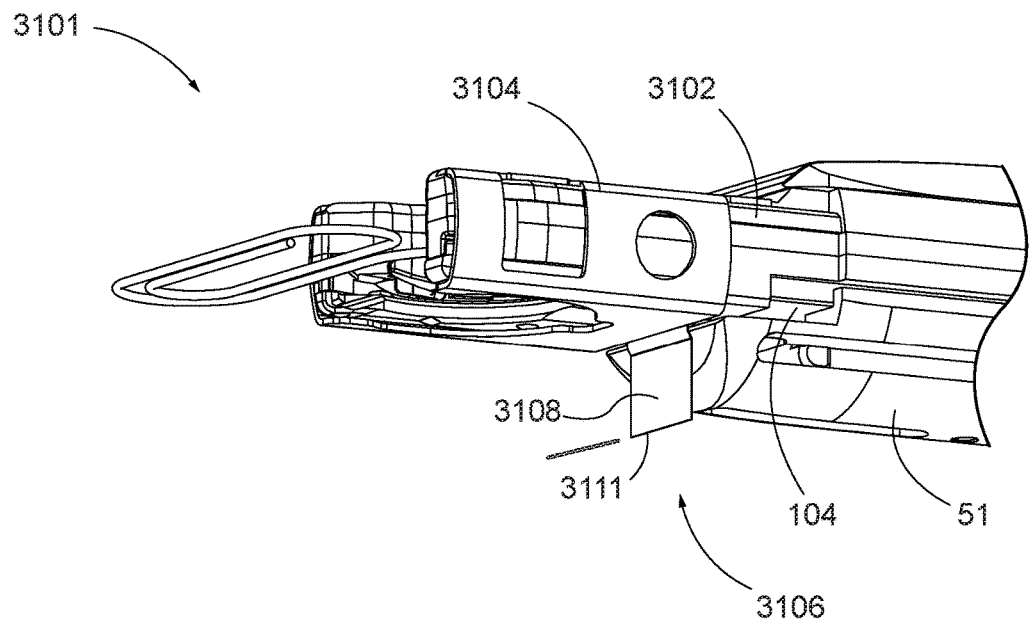
FIG. 62B depicts an enlarged bottom perspective view of the cartridge receiving assembly and the cartridge of FIG. 62A, with the cage of the cartridge in the closed position and with the tab pulled to an unfolded configuration.
Figure 62C:
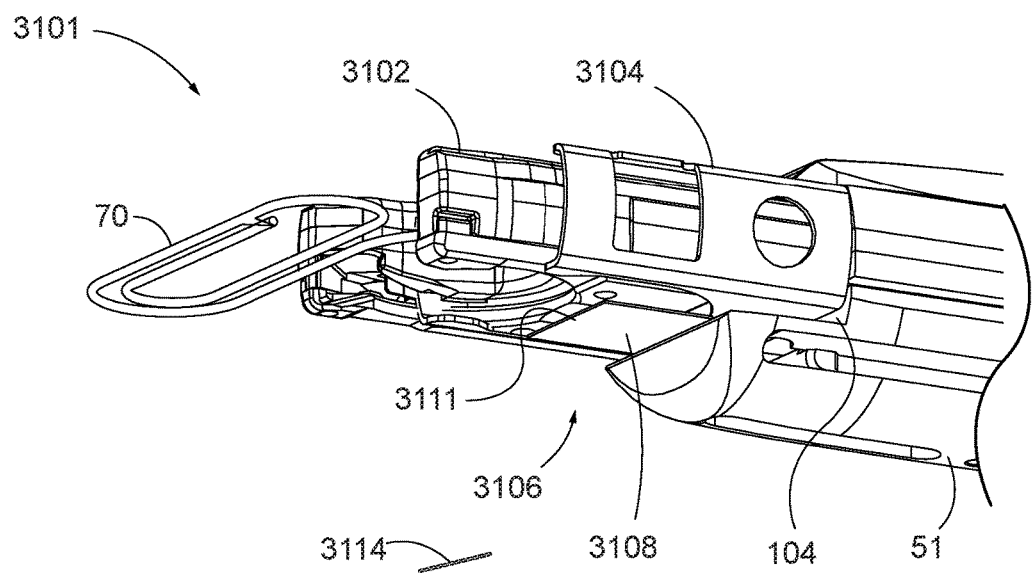
FIG. 62C depicts an enlarged bottom perspective view of the cartridge receiving assembly and the cartridge of FIG. 62A, with the cage of the cartridge in an opened position.
Figure 63:
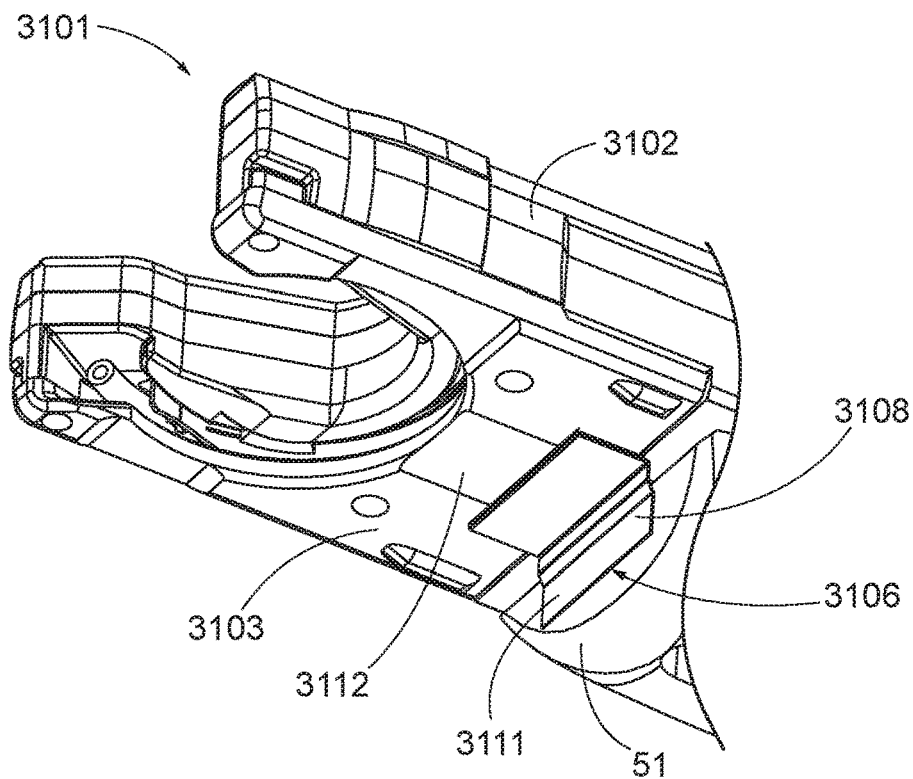
FIG. 63 depicts the enlarged bottom perspective view of the cartridge receiving assembly and the cartridge of FIG. 62A, with the tab in the folded configuration and with various features removed for improved clarity.
Figure 64:
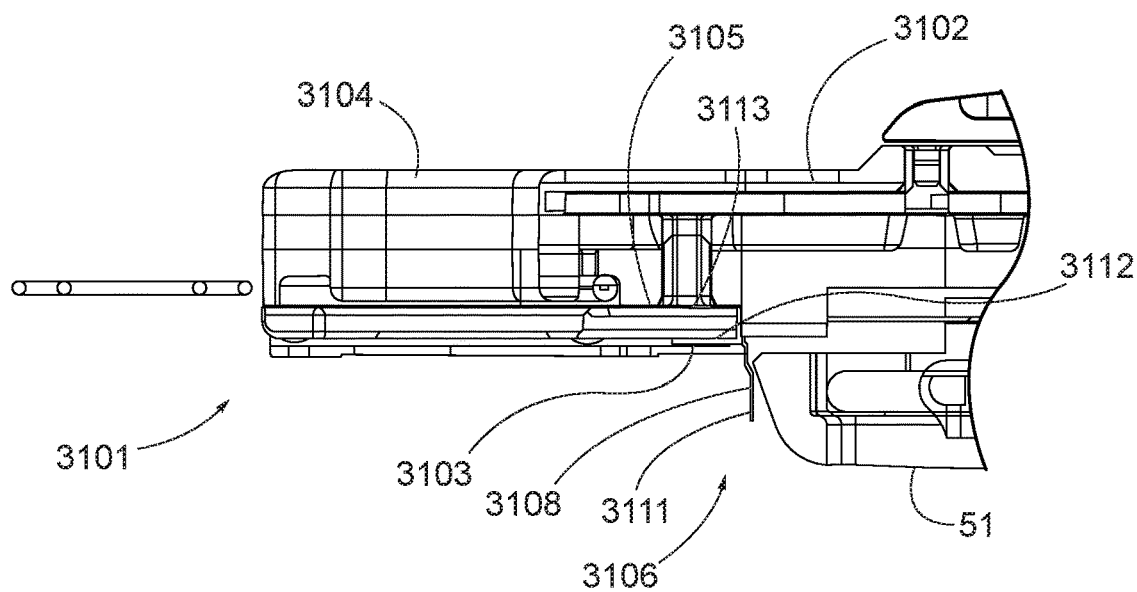
FIG. 64 depicts a cross-sectional view of the cartridge receiving assembly and cartridge of FIG. 62A, with the cage in the closed position and with the tab in the folded configuration, taken along section line 64-64 of FIG. 62A.
Figure 65:
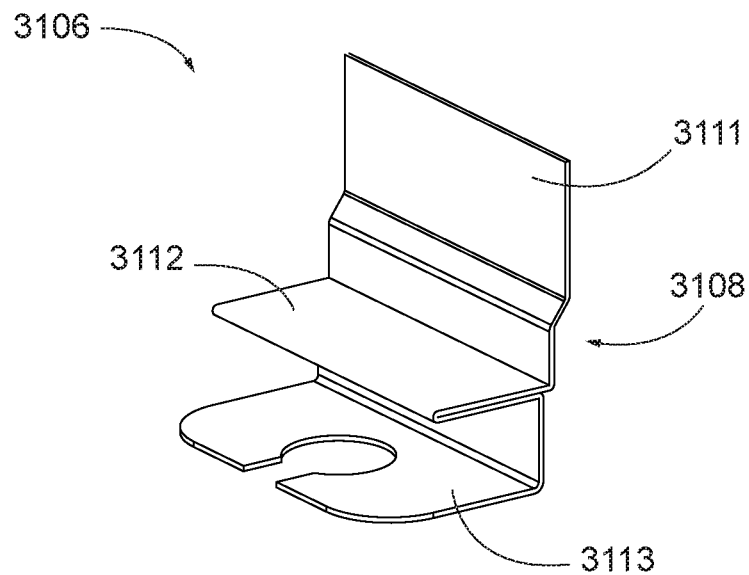
FIG. 65 depicts a perspective view of the tab of FIG. 62A in the folded configuration.

As depicted in the present example of FIG. 63, a shim tab blocker (3108) has a series of folds (3112) releasably positioned in lower cavity (3103) between cartridge body (3102) and cage (3104) and securely positioned in an upper cavity (3105) within cartridge (3101). Folds (3112) frictionally engage cartridge body (3102) and cage (3104) to inhibit movement therebetween. A bottom portion (3111) of shim tab blocker (3108) extends outwardly from lower cavity (3103) between cartridge body (3102) and cage (3104) along lower jaw (51) for ease of access by the operator. As best seen in FIGS. 62A-62C, the operator may grasp the extending bottom portion (3111) of shim tab blocker (3108) and pull folds (3112) from between cartridge body (3102) and cage (3104) to release the frictional resistance. Shim tab blocker (3108) of the present example is fixedly attached to cartridge (3101) at an upper portion thereof, which securely connects shim tab blocker (3108) to cartridge (3101) in upper cavity (3105).

In some other versions, shim tab blocker (3108) of tab removal cage securement (3106) may extend outwardly from between cartridge body (3102) and cage (3104) along upper jaw (56) of cartridge receiving assembly (50). By way of further example, it may be desirable to include a plurality of shim tab blockers (3108) for frictionally securing cage (3104) as discussed above. Although not shown, release cage securement (3106) may alternatively have shim tab blocker (3108) extending outwardly from cartridge body (3102) and cage (3104) at varying locations along cage (3104). Shim tab blocker (3108) of tab release cage securement (3106) is made from a plastic material in the present example. However, it should be understood that tab release cage securement (3106) may be made from various materials that provide frictional engagement between cartridge body (3102) and cage (3104).

S. Ring Cage Securement

Figure 66:
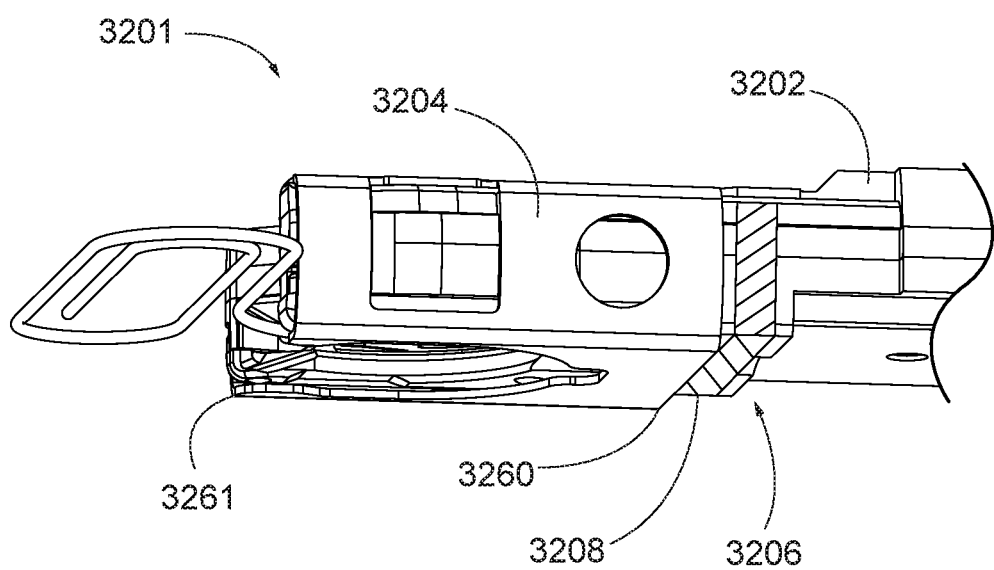
FIG. 66 depicts a bottom perspective view of an exemplary cartridge configured for receipt in the cartridge receiving assembly of FIG. 2A, with an exemplary blocking ring cage securement.
Figure 67A:
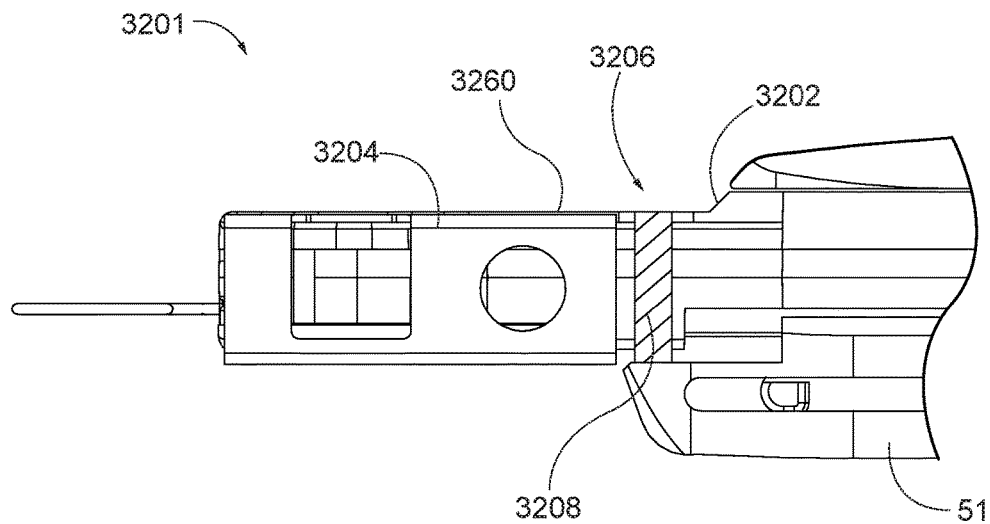
FIG. 67A depicts an enlarged side view of the cartridge and the blocking ring of FIG. 66, with the blocking ring secured to the cartridge, and with a cage of the cartridge in a closed position.
Figure 67B:
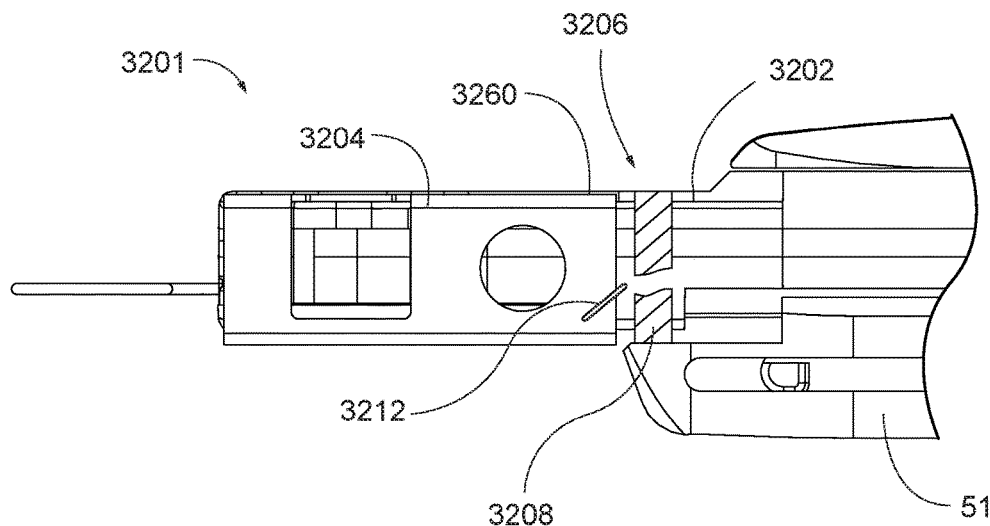
FIG. 67B depicts an enlarged side view of the cartridge and the blocking ring of FIG. 66, with the blocking ring in a fractured state, and with the cage in the closed position.
Figure 67C:
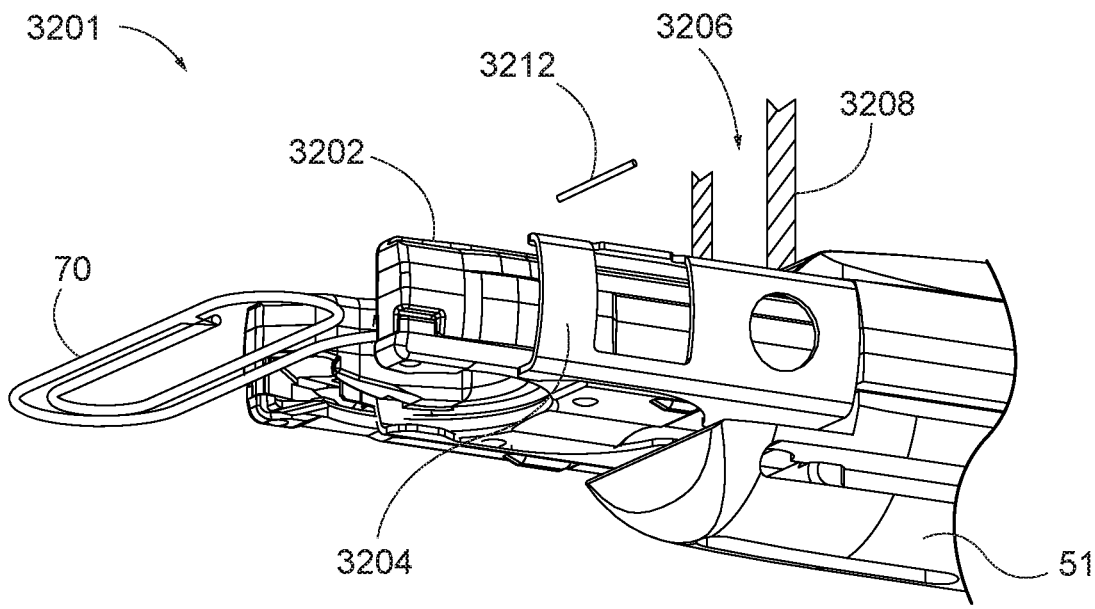
FIG. 67C depicts an enlarged perspective view of the cartridge and the blocking ring of FIG. 66, with the blocking ring disengaged from the cartridge, and with the cage in an open position.

FIGS. 66-67C illustrate a cartridge (3201) with a first exemplary ring cage securement (3206) formed by a ring blocker (3208) removably secured around a cartridge body (3202) adjacent to a proximal end portion (3260) of a cage (3204). It should be understood that cartridge (3201) of this example may be configured and operable just like cartridge (30) described above, except for the differences explicitly noted herein. Ring blocker (3208) of ring cage securement (3206) is sized and shaped to be positioned in between cartridge body (3102) and lower jaw (51) to block proximal movement of cage (3204) from the closed position toward the opened position. Ring blocker (3208) is configured to be removed from between cartridge body (3202) and cartridge receiving assembly (50) upon application of a severing force to effectively break ring blocker (3206) from its secured position. Cage (3204) is thus allowed to slidably translate from the closed position toward the opened position through elongate slot (104) after ring blocker (3206) is severed and removed.

In the present example, ring blocker (3208) is an o-ring, but other band-like structures, such as a cellophane ring or suture loop tied around a portion of a cartridge body (3202), may be so used. Through use of a tool (3212), the operator cuts ring blocker (3208) for removal from its secured position between cartridge body (3202) and one or both of lower and upper jaws (51, 56) to release the resistance generated by its original secured position. It should be understood that the size, thickness and shape of ring blocker (3208) of ring cage securement (3206) may vary in comparison to that described herein.

Figure 68:
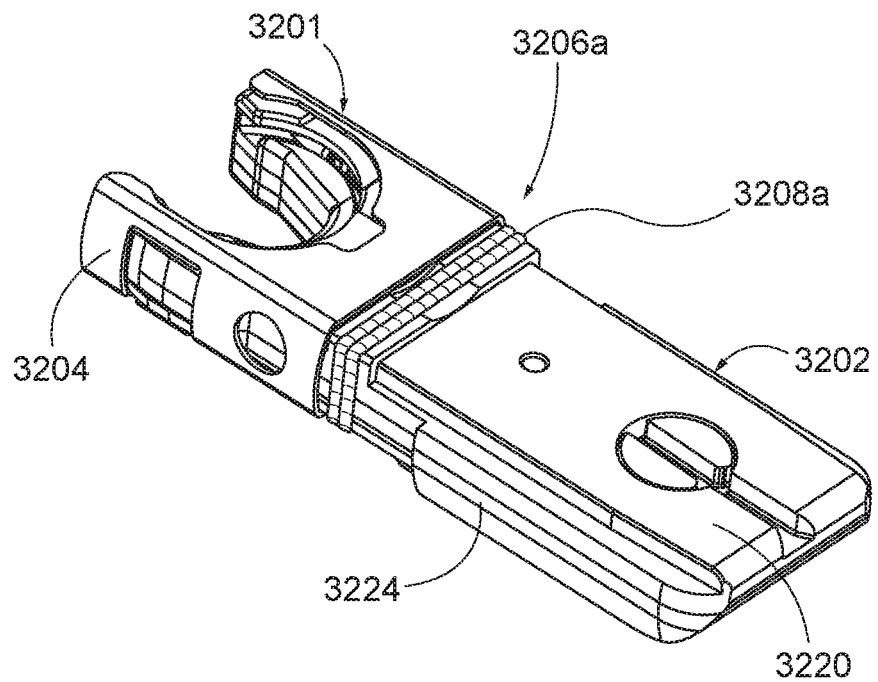
FIG. 68 depicts a bottom perspective view of an exemplary cartridge configured for receipt in the cartridge receiving assembly of FIG. 2A, with a second exemplary blocking ring cage securement.

A second exemplary ring cage securement (3206a) with a ring blocker (3208a) is shown in FIG. 68 with cartridge (3201). Ring blocker (3208a) of this example, like ring blocker (3208) (see FIG. 67A) discussed above, is removably secured around cartridge body (3202) for inhibiting proximal movement of cage (3204) (see FIG. 67C) from the closed position toward the opened position. However, in the present example, ring blocker (3208a) is a suture thread wrapped around a portion of cartridge body (3202) and tied to its secured position. Suture thread ring blocker (3208a) may thus be untied by the operator or severed, such as with a scissors or other tool.

Figure 69:
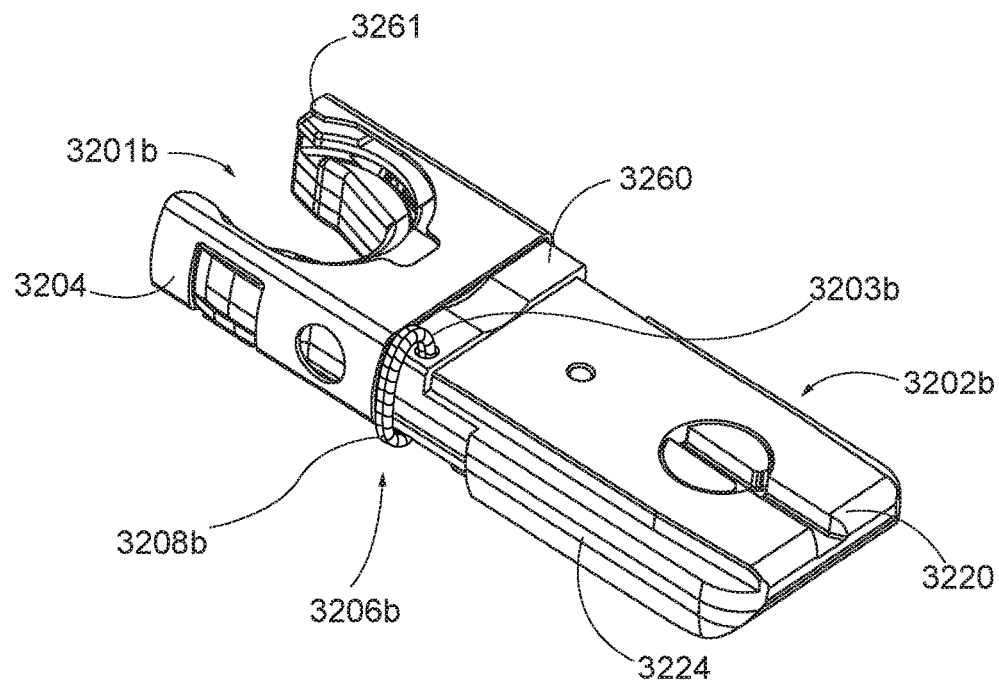
FIG. 69 depicts a bottom perspective view of an exemplary cartridge configured for receipt in the cartridge receiving assembly of FIG. 2A, with a third exemplary blocking ring cage securement.

FIG. 69 illustrates a cartridge (3201b) with a third exemplary ring cage securement (3206b) formed by a relatively small annular ring blocker (3208b) received within a hole (3203b) extending transversely through a cartridge body (3202b). It should be understood that cartridge (3201b) of this example may be configured and operable just like cartridge (30) described above, except for the differences explicitly noted herein. Hole (3203b) with ring blocker (3208b) received therein are positioned adjacent to cage (3204) to inhibit proximal movement from the closed positon toward the opened position. Similar to ring blocker (3208) (see FIG. 67A) discussed above, the operator simply cuts ring blocker (3208b) for removal from its secured position to release the resistance generated by its original secured position. Cage (3204) is thus free to translate proximally to the open position after ring blocker (3208b) is severed and removed.

Figure 70A:
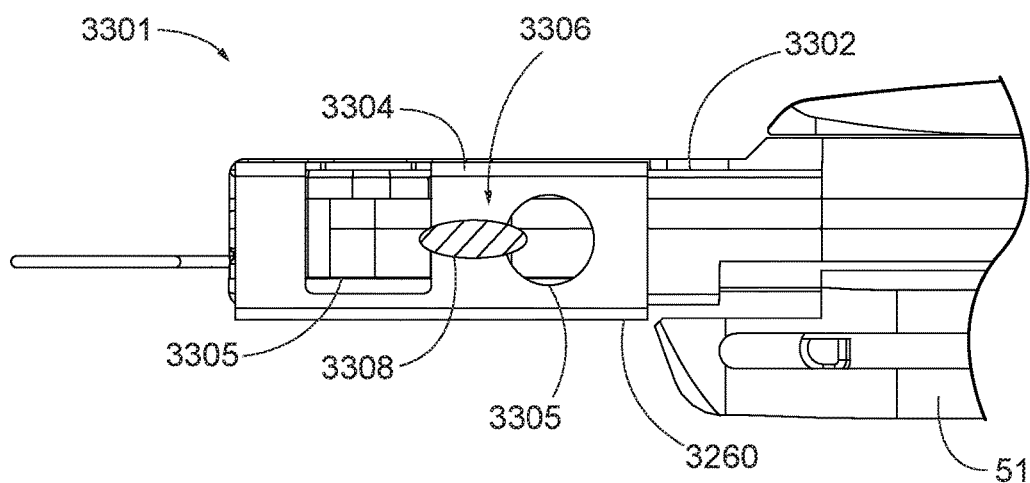
FIG. 70A depicts a side view of an exemplary cartridge configured for receipt in the cartridge receiving assembly of FIG. 2A, with a fourth exemplary blocking ring cage securement, with the blocking ring in an intact state.
Figure 70B:
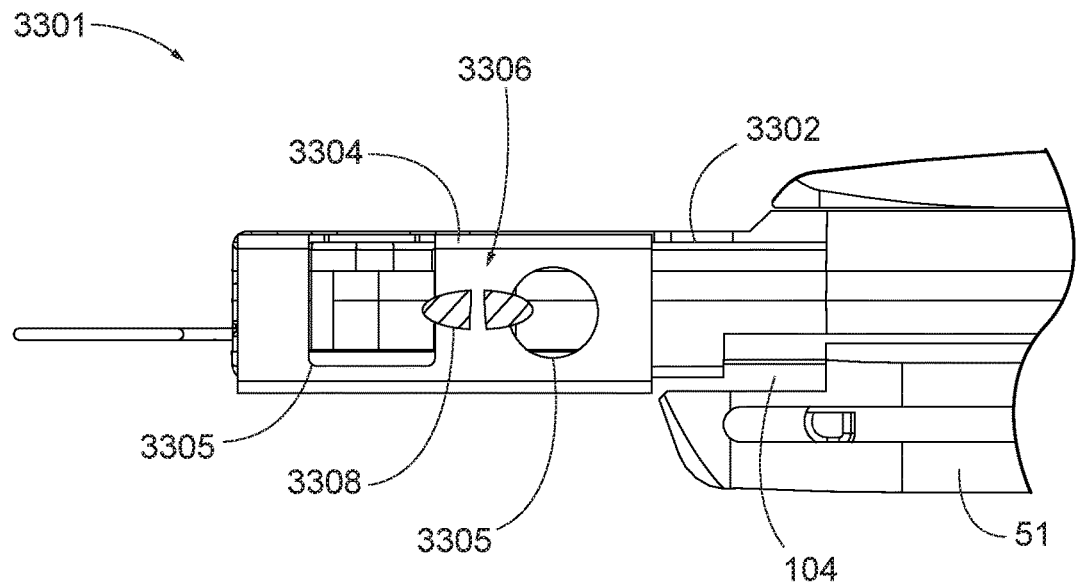
FIG. 70B depicts an enlarged side view of the cartridge and the blocking ring cage securement of FIG. 70A, with the blocking ring in a fractured state.
Figure 70C:
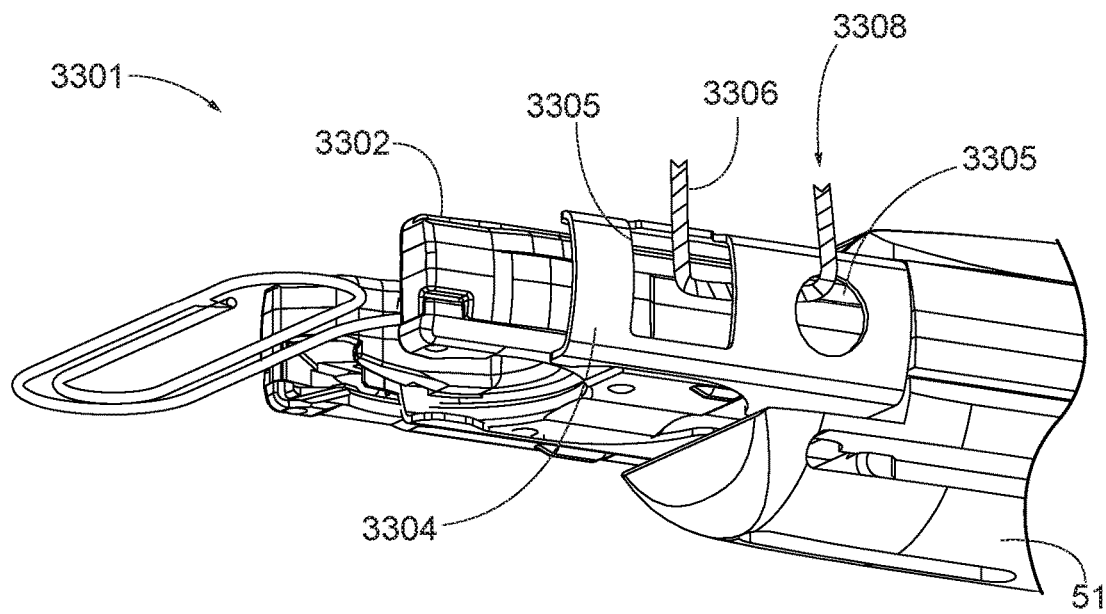
FIG. 70C depicts an enlarged perspective view of the cartridge and the blocking ring cage securement of FIG. 70A, with the blocking ring being removed from the cartridge.

FIGS. 70A-70C illustrate a cartridge (3301) with a fourth exemplary ring cage securement (3306) having another relatively small annular ring blocker (3308). It should be understood that cartridge (3301) of this example may be configured and operable just like cartridge (30) described above, except for the differences explicitly noted herein. Ring blocker (3308) is received through a hole (not shown) in a lateral side of a cartridge body (3302) and further threaded through a pair of orifices (3305) of a cage (3304). Ring blocker (3308) thereby inhibits movement of cage (3304) until ring blocker (3308) of ring cage securement (3306) is severed from its secured position. Cage (3304) is thus free to translate proximally to the open position after ring blocker (3208) is severed and removed.

T. Sleeve Cage Securement

Figure 71A:
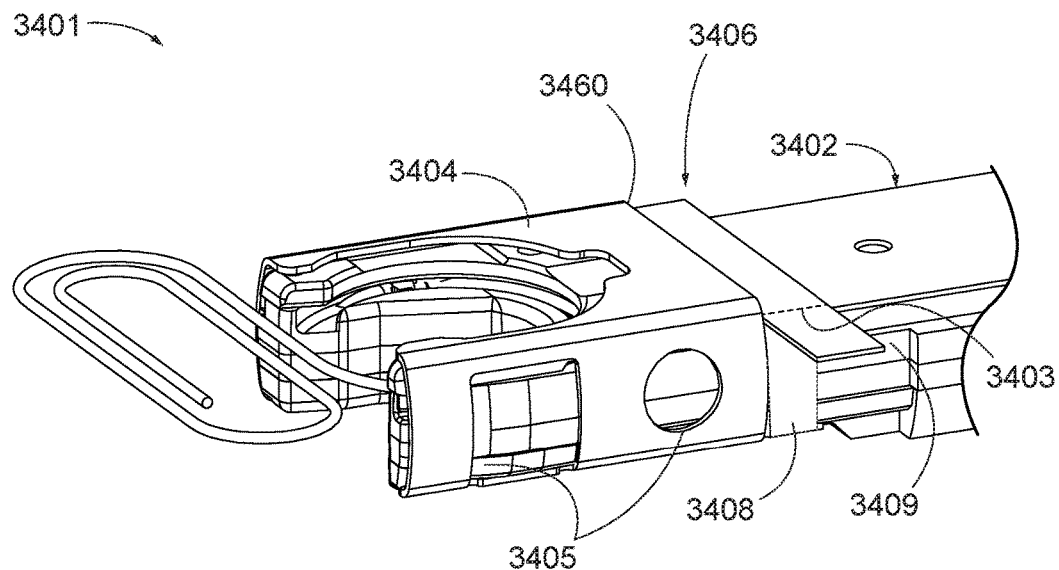
FIG. 71A depicts an enlarged perspective view of an exemplary cartridge configured for receipt in the cartridge receiving assembly of FIG. 2A, with an exemplary sleeve cage securement, with the sleeve secured to the cartridge.
Figure 71B:
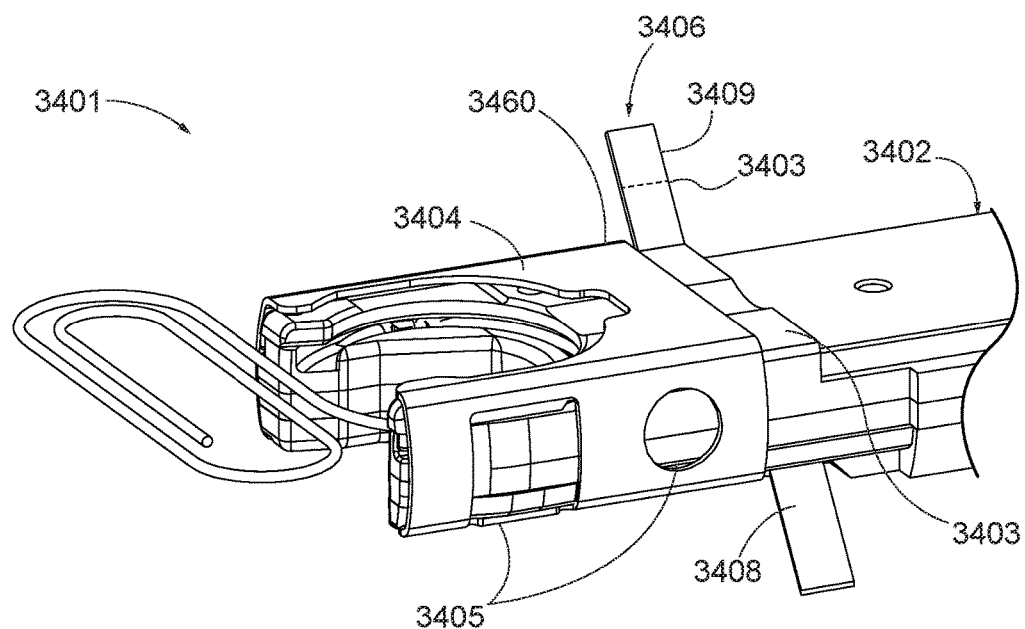
FIG. 71B depicts an enlarged perspective view of the cartridge and the sleeve cage securement of FIG. 71A, with the sleeve being removed from the cartridge.

FIGS. 71A-71B illustrate a cartridge (3401) with exemplary sleeve cage securement (3406) in the form of a sleeve blocker (3408) removably secured against a cartridge body (3402) adjacent to a proximal end portion (3460) of a cage (3404). It should be understood that cartridge (3401) of this example may be configured and operable just like cartridge (30) described above, except for the differences explicitly noted herein. Sleeve blocker (3408) is sized and shaped to fit within a cavity (3403) in between cartridge body (3402) and lower jaw (51) (see FIG. 70C) to block movement of cage (3404) from the closed position toward the opened position. Sleeve blocker (3408) is configured to be removed from between cartridge body (3402) and cartridge receiving assembly (50) by tearing sleeve blocker (3406) away from cartridge body (3402). After sleeve blocker (3406) is torn away from cartridge body (3402), sleeve blocker (3402) no longer blocks proximal movement of cage (3404). Cage (3404) is thus allowed to slidably translate from the closed position toward the opened position through elongate slot (104) (see FIG. 70C).

In the present example, sleeve blocker (3408) has a frangible connection (3403) and surrounds a portion of a cartridge body (3402) along proximal end portion (3460) of cage (3404). The operator breaks frangible connection (3403) to remove sleeve blocker by manipulating a flexible tab (3409) which extends therefrom. In some versions, it may be desirable to include a plurality of sleeve blockers (3408) for securing cage (3404) in the closed position. Further, it may be desirable to thread sleeve blocker (3408) through one or more orifices (3405) of cage (3404) to inhibit movement of cage (3404) until sleeve blocker (3408) is separated from its secured position. As with other components described herein, sleeve cage securement (3406) may be relocated, varied, modified, substituted, or supplemented in a variety of ways. In some versions, sleeve cage securement (3406) of cage (3404) is made from a mylar material. However, it should be understood that sleeve cage securement (3406) may be made from various materials that restrict movement of cage (3404) (including plastic).

III. Method of Cage Movement During a Surgical Procedure

A. Abutment Release of Cage toward Opened Position

In use, and referring back to FIGS. 8-10B, the operator introduces cartridge receiving assembly (102) into the patient and actuates cartridge (201) for suturing tissue as discussed above in greater detail. During such use, cage (204) may receive less than the predetermined opening force in the proximal direction, such as from inadvertently contacting tissue, yet remain in the closed position via tab abutment (208) of chamfered tab cage securement (206). In the event that the operator desires to remove needle (70) from cartridge body (202), the operator grips cage (204), such as by hand or with the aid of a tool (e.g., a conventional tissue grasping instrument), and selectively forces cage (204) proximally through elongate slot (104) with at least the predetermined opening force. Upon the application of at least the predetermined opening force in the proximal direction, deflector (210) deflects such that tab abutment (208) slips and releases movement of cage (204) to the opened position. The operator releases cage (204), removes needle cover (83) from cartridge body (202) to access needle (70), and removes needle (70) from cartridge body (202). The operator may then dispose of the used needle (70) and cartridge (201) to replace with a new cartridge (201) to perform the surgical procedure as desired. While such use refers specifically to cartridge (201) and chamfered tab cage securement (206), it will be appreciated that similar use may be performed with alternative cage securements having abutments, various examples of which are described herein. The use may thus vary to accommodate alternative structures described above and is not limited to the particular movements and structures described with respect to chamfered tab cage securement (206).

B. Rack Release of Cage toward Opened Position

With respect to FIGS. 27A-27B, the operator introduces cartridge receiving assembly (102) into the patient and actuates cartridge (1501) for suturing tissue as discussed above in greater detail. During such use, cage (1504) may receive force in the proximal direction, such as from inadvertently contacting tissue, yet remain in the closed position so long as rack (45) remains unretracted and abutment (1508) of tongue cage securement (1506) is engaged with cage (1504). More particularly, abutment (1508) extends distally from rack (45) for engagement with cage (1504). Manipulating first user input member (12) reciprocates rack (45) to actuate cartridge (1501) while also disengaging abutment (1508) from cartridge body (1502). In the event that the needle (70) becomes difficult to move, such as by becoming jammed in use, abutment (1508) is already disengaged from cage (1504) for free translation of cage (1504) should the operator desire to remove needle (70) from cartridge body (1502). To this end, the operator grips cage (1504), such as by hand or with the aid of a tool (e.g., conventional tissue graspers), and selectively forces cage (1504) proximally through elongate slot (104) to the opened position. The operator releases cage (1504), removes needle cover (83) from cartridge body (1502) to access needle (70), and removes needle (70) from cartridge body (1502). The operator may then dispose of the used needle (70) and used cartridge (201) to replace with a new cartridge (201) to perform the surgical procedure as desired. While such use refers specifically to cartridge (1501) and tongue cage securement (1506), it will be appreciated that similar use may be performed with alternative cage securements having abutments and operative actuation, various examples of which are described herein. The use may thus vary to accommodate alternative structures described above and is not limited to the particular movements and structures described with respect to tongue cage securement (1506).

C. Blocker Release of Cage toward Opened Position

With respect to FIGS. 57-61, the operator introduces cartridge receiving assembly (102) into the patient and actuates cartridge (3001) for suturing tissue as discussed above in greater detail. During such use, cage (3004) may receive force in the proximal direction, such as from inadvertently contacting tissue, yet remain in the closed position. In the event that the operator desires to remove needle (70) from cartridge body (3002), the operator selectively manipulates blocker (3008) of tab removal cage securement (3006) to remove at least a portion of blocker (3008) from the proximal movement path of cage (3004) toward the opened position. With the blocker (3008) removed, the user grips cage (3004), such as by hand or with the aid of a tool (e.g., conventional tissue graspers), and selectively forces cage (3004) proximally through elongate slot (104) to the opened position. The operator releases cage (3004), removes needle cover (83) from cartridge body (3002) to access needle (70), and removes needle (70) from cartridge body (3002). The operator may then dispose of the used needle (70) and used cartridge (201) to replace with a new cartridge (201) to perform the surgical procedure as desired. While such use refers specifically to cartridge (3001) and tab removal cage securement (3006), it will be appreciated that similar use may be performed with alternative cage securements having blockers, various examples of which are described herein. By way of example, removal of alternative blockers may include cutting, fracturing a frangible connection, or manipulating at least a portion of the alternative blocker. The use may thus vary to accommodate alternative structures described above and is not limited to the particular movements and structures described with respect to tab removal cage securement (1506).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body having an actuator configured to be selectively manipulated by an operator; (b) a shaft extending distally from the body; (c) a cartridge receiving assembly projecting from a distal end portion of the shaft, wherein the cartridge receiving assembly has a transmission mechanism operatively connected to the actuator and configured to be selectively driven via selective manipulation of the actuator; (d) a suture cartridge configured to be received within the cartridge receiving assembly, wherein the suture cartridge comprises: (i) a cartridge body, (ii) a needle removably positioned within the cartridge body, (iii) a drive assembly releasably coupled to the needle and configured to engage the transmission mechanism to thereby drive the needle along a predetermined path, and (iv) a cage movably secured to the cartridge body and configured to selectively move relative to the cartridge body from a closed position to an opened position, wherein the cage in the closed position is configured to contain the needle within the cartridge body, and wherein the cage in the opened position is configured allow removal of the needle from the cartridge body; and (e) a cage securement configured selectively move from a first position to a second position, wherein the cage securement in the first position is configured to inhibit movement of the cage from the closed position toward the opened position, and wherein the cage securement in the second position is configured to release movement of the cage for selectively moving the cage to the opened position and removing the needle from the cartridge body during a surgical procedure.

Example 2

The surgical instrument of Example 1, wherein the cage securement includes: (i) an abutment projecting from at least one of the cartridge receiving assembly or the cartridge body, wherein the abutment projects toward the cage and is configured to inhibit movement of the cage from the closed position toward the opened position up to a predetermined opening force, and (ii) a deflector associated with at least one of the cartridge receiving assembly, the cartridge body, or the cage, wherein the deflector is configured to deflect upon the application of at least the predetermined opening force via the abutment such that the abutment releases the movement of the cage toward the opened position.

Example 3

The surgical instrument of Example 2, wherein the abutment extends from the deflector such that the abutment is configured to deflect with the deflector.

Example 4

The surgical instrument of Example 3, wherein the deflector is associated with the cartridge receiving assembly and the abutment projects from the cartridge receiving assembly.

Example 5

The surgical instrument of Example 3, wherein the deflector is associated with the cartridge body and the abutment projects from the cartridge body.

Example 6

The surgical instrument of Example 1, wherein the cage securement includes: (i) an abutment projecting from the cage, wherein the abutment projects toward at least one of the cartridge receiving assembly or the cartridge body and is configured to inhibit movement of the cage from the closed position toward the opened position up to a predetermined opening force, and (ii) a deflector associated with at least one of the cartridge receiving assembly, the cartridge body, or the cage, wherein the deflector is configured to deflect upon the application of at least the predetermined opening force via the abutment such that the abutment releases the movement of the cage toward the opened position.

Example 7

The surgical instrument of Example 6, wherein the abutment extends from the deflector such that the abutment is configured to deflect with the deflector.

Example 8

The surgical instrument of Example 7, wherein the deflector is associated with the cage and the abutment projects from the cage toward the cartridge receiving assembly.

Example 9

The surgical instrument of Example 7, wherein the deflector is associated with the cage and the abutment projects from the cage toward the cartridge body.

Example 10

The surgical instrument of Example 1, wherein the cage securement includes a blocker removably secured against the cage, and wherein the blocker is configured to inhibit movement of the cage from the closed position toward the opened position, and wherein the blocker is configured to be removed from the suture cartridge to free movement of the cage to the opened position.

Example 11

The surgical instrument of Example 10, wherein the blocker comprises a blocker film positioned between the suture cartridge and the cartridge receiving assembly, wherein the blocker film is configured to block movement of the cage from the closed position toward the opened position.

Example 12

The surgical instrument of Example 11, wherein the blocker film is frictionally engaged with each of the cartridge receiving assembly and the suture cartridge to block movement of the cage from the closed position toward the opened position.

Example 13

The surgical instrument of Example 10, wherein the blocker comprises a blocker collar removably connected to the cartridge body, wherein the blocker collar is configured to block movement of the cage from the closed position toward the opened position.

Example 14

The surgical instrument of Example 13, wherein the blocker collar is further connected to the cage to removably couple the cage to the cartridge body in the closed position.

Example 15

The surgical instrument of Example 1, wherein the cage securement includes an abutment projecting from the cartridge receiving assembly toward the cage, wherein the abutment is operatively connected to the actuator, wherein the abutment is configured to be selectively moved via selective manipulation of the actuator from an engaged position to a disengaged position, wherein the abutment in the engaged position is engaged with the cage and configured to inhibit movement of the cage from the closed position toward an opened position, and wherein the abutment in the disengaged position is disengaged from the cage to release movement of the cage to the opened position.

Example 16

A surgical instrument, comprising: (a) a body having an actuator configured to be selectively manipulated by an operator; (b) a shaft extending distally from the body; (c) a cartridge receiving assembly projecting from a distal end portion of the shaft, wherein the cartridge receiving assembly has a transmission mechanism operatively connected to the actuator and configured to be selectively driven via selective manipulation of the actuator, and (d) a cage securement extending from the cartridge receiving assembly and configured to selectively move from a first position to a second position, wherein the cage securement in the first position is configured inhibit movement of a cage of a suture cartridge from a closed position toward an opened position, and wherein the cage securement in the second position is configured to release movement of the cage for selectively moving the cage to the opened position and removing the needle from the cartridge body during a surgical procedure.

Example 17

A suture cartridge for a surgical instrument, comprising: (a) a cartridge body configured to be received within a cartridge receiving assembly of the surgical instrument; (b) a needle removably positioned within the cartridge body; (c) a drive assembly releasably coupled to the needle and configured to engage a transmission mechanism of the surgical instrument to thereby drive the needle along a predetermined path; (d) a cage movably secured to the cartridge body and configured to selectively move relative to the cartridge body from a closed position to an opened position, wherein the cage in the closed position is configured to contain the needle within the cartridge body, and wherein the cage in the opened position is configured such that the needle is removable from the cartridge body; and (e) a cage securement configured to selectively move from a first position to a second position, wherein the cage securement in the first position is configured to inhibit movement of the cage from the closed position toward the opened position, and wherein the cage securement in the second position is configured to release movement of the cage for selectively moving the cage to the opened position and removing the needle from the cartridge body during a surgical procedure.

Example 18

The suture cartridge of Example 17, wherein the cage securement includes: (i) an abutment projecting from the cartridge body toward the cage, wherein the abutment is configured to inhibit movement of the cage from the closed position toward the opened position up to the predetermined opening force, and (ii) a deflector associated with at least one of the cartridge body or the cage, wherein the deflector is configured to deflect upon the application of at least the predetermined opening force via the abutment such that the abutment releases the movement of the cage toward the opened position.

Example 19

The suture cartridge of Example 17, wherein the cage securement includes: (i) an abutment projecting from the cage, wherein the abutment projects toward the cartridge body or is configured to project toward the cartridge receiving assembly, wherein the abutment is configured to inhibit movement of the cage from the closed position toward the opened position up to the predetermined opening force, and (ii) a deflector associated with at least one of the cartridge body or the cage, wherein the deflector is configured to deflect upon the application of at least the predetermined opening force via the abutment such that the abutment releases the movement of the cage toward the opened position.

Example 20

The suture cartridge of Example 17, wherein the cage securement includes a blocker removably secured against the cage, and wherein the blocker is configured to inhibit movement of the cage from the closed position toward the opened position up to the predetermined opening force, and wherein the blocker is configured to be removed from the suture cartridge upon the application of at least the predetermined opening force to free movement of the cage to the opened position.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein, is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   a) a body having an actuator configured to be selectively manipulated by an operator;
   b) a shaft extending distally from the body;
   c) a cartridge receiving assembly projecting from a distal end portion of the shaft and having a first jaw and a second jaw, wherein the second jaw has defining an elongate slot therein, wherein the cartridge receiving assembly has a transmission mechanism operatively connected to the actuator and configured to be selectively driven via selective manipulation of the actuator;
   d) a suture cartridge configured to be received within the cartridge receiving assembly, wherein the suture cartridge comprises:
      i. a cartridge body configured to be received and retained between the first and second jaws such that the cartridge body is outside of the elongate slot,
      ii. a needle removably positioned within the cartridge body,
      iii. a drive assembly releasably coupled to the needle and configured to engage the transmission mechanism to thereby drive the needle along a predetermined path, and
      iv. a cage movably secured to the cartridge body and configured to selectively move relative to the cartridge body proximally through the elongate slot of cartridge receiving assembly from a closed position to an opened position while the cartridge body remains retained between the first and second jaws, wherein the cage in the closed position is configured to contain the needle within the cartridge body, and wherein the cage in the opened position is received within the elongate slot and configured to allow removal of the needle from the cartridge body; and
   e) a cage securement configured to selectively move from a first position to a second position, wherein the cage securement in the first position is configured to inhibit movement of the cage from the closed position toward the opened position, and wherein the cage securement in the second position is configured to release movement of the cage for selectively moving the cage to the opened position and removing the needle from the cartridge body during a surgical procedure.

2. The surgical instrument of claim 1, wherein the cage securement includes:
   (i) an abutment projecting from at least one of the cartridge receiving assembly or the cartridge body, wherein the abutment projects toward the cage and is configured to inhibit movement of the cage from the closed position toward the opened position up to a predetermined opening force, and
   (ii) a deflector associated with at least one of the cartridge receiving assembly, the cartridge body, or the cage, wherein the deflector is configured to deflect upon the application of at least the predetermined opening force via the abutment such that the abutment releases the movement of the cage toward the opened position.

3. The surgical instrument of claim 2, wherein the abutment extends from the deflector such that the abutment is configured to deflect with the deflector.

4. The surgical instrument of claim 3, wherein the deflector is associated with the cartridge receiving assembly and the abutment projects from the cartridge receiving assembly.

5. The surgical instrument of claim 3, wherein the deflector is associated with the cartridge body and the abutment projects from the cartridge body.

6. The surgical instrument of claim 1, wherein the cage securement includes:
   (i) an abutment projecting from the cage, wherein the abutment projects toward at least one of the cartridge receiving assembly or the cartridge body and is configured to inhibit movement of the cage from the closed position toward the opened position up to a predetermined opening force, and
   (ii) a deflector associated with at least one of the cartridge receiving assembly, the cartridge body, or the cage, wherein the deflector is configured to deflect upon the application of at least the predetermined opening force via the abutment such that the abutment releases the movement of the cage toward the opened position.

7. The surgical instrument of claim 6, wherein the abutment extends from the deflector such that the abutment is configured to deflect with the deflector.

8. The surgical instrument of claim 7, wherein the deflector is associated with the cage and the abutment projects from the cage toward the cartridge receiving assembly.

9. The surgical instrument of claim 7, wherein the deflector is associated with the cage and the abutment projects from the cage toward the cartridge body.

10. The surgical instrument of claim 1, wherein the cage securement includes a blocker removably secured against the cage, and wherein the blocker is configured to inhibit movement of the cage from the closed position toward the opened position, and wherein the blocker is configured to be removed from the suture cartridge to free movement of the cage to the opened position.

11. The surgical instrument of claim 10, wherein the blocker comprises a blocker film positioned between the suture cartridge and the cartridge receiving assembly, wherein the blocker film extends across the elongate channel to block proximal movement of the cage through the elongate channel from the closed position toward the opened position.

12. The surgical instrument of claim 11, wherein the blocker film is frictionally engaged with each of the cartridge receiving assembly and the suture cartridge to block movement of the cage from the closed position toward the opened position.

13. The surgical instrument of claim 10, wherein the blocker comprises a blocker collar removably connected to the cartridge body, wherein the blocker collar is configured to block movement of the cage from the closed position toward the opened position.

14. The surgical instrument of claim 1, wherein the cage securement includes:
   (i) an abutment projecting from the cartridge receiving assembly, wherein the abutment projects toward the cage and is configured to inhibit movement of the cage from the closed position toward the opened position up to a predetermined opening force, and
   (ii) a deflector associated with at least one of the cartridge receiving assembly or the cage, wherein the deflector is configured to deflect upon the application of at least the predetermined opening force via the abutment such that the abutment releases the movement of the cage toward the opened position.

15. The surgical instrument of claim 14, wherein the deflector is associated with the cage.

16. The surgical instrument of claim 14, wherein the abutment extends across the elongate channel to block proximal movement of the cage through the elongate channel from the closed position toward the opened position.

17. A surgical instrument, comprising:
   a) a body having an actuator configured to be selectively manipulated by an operator;
   b) a shaft extending distally from the body;
   c) a cartridge receiving assembly projecting from a distal end portion of the shaft, wherein the cartridge receiving assembly has a transmission mechanism operatively connected to the actuator and configured to be selectively driven via selective manipulation of the actuator;
   d) a suture cartridge configured to be received within the cartridge receiving assembly, wherein the suture cartridge comprises:
      i. a cartridge body,
      ii. a needle removably positioned within the cartridge body,
      iii. a drive assembly releasably coupled to the needle and configured to engage the transmission mechanism to thereby drive the needle along a predetermined path, and
      iv. a cage movably secured to the cartridge body and configured to selectively move relative to the cartridge body from a closed position to an opened position, wherein the cage in the closed position is configured to contain the needle within the cartridge body, and wherein the cage in the opened position is configured to allow removal of the needle from the cartridge body; and
   e) a cage securement configured to selectively move from a first position to a second position, wherein the cage securement in the first position is configured to inhibit movement of the cage from the closed position toward the opened position, and wherein the cage securement in the second position is configured to release movement of the cage for selectively moving the cage to the opened position and removing the needle from the cartridge body during a surgical procedure,
wherein the cage securement includes an abutment projecting from the cartridge receiving assembly toward the cage, wherein the abutment is operatively connected to the actuator, wherein the abutment is configured to be selectively moved via selective manipulation of the actuator from an engaged position to a disengaged position, wherein the abutment in the engaged position is engaged with the cage and configured to inhibit movement of the cage from the closed position toward an opened position, and wherein the abutment in the disengaged position is disengaged from the cage to release movement of the cage to the opened position.

18. A surgical instrument, comprising:
   a) a body having an actuator configured to be selectively manipulated by an operator;
   b) a shaft extending distally from the body;
   c) a cartridge receiving assembly projecting from a distal end portion of the shaft and configured to receive a suture cartridge, wherein the cartridge receiving assembly has a transmission mechanism operatively connected to the actuator and configured to be selectively driven via selective manipulation of the actuator; and d) a cage securement connected to and extending from the cartridge receiving assembly and configured to selectively move from a first position to a second position while connected to the cartridge receiving assembly, wherein the cage securement in the first position is configured to inhibit movement of a cage of the suture cartridge from a closed position toward an opened position, and wherein the cage securement in the second position is configured to release movement of the cage for selectively moving the cage to the opened position and removing the needle from the cartridge body during a surgical procedure,
  i. a cartridge body configured to be received by the cartridge receiving assembly,
  ii. a needle removably positioned within the cartridge body,
  iii. a drive assembly releasably coupled to the needle and configured to engage the transmission mechanism to thereby drive the needle along a predetermined path, and
  iv. a cage movably secured to the cartridge body and configured to selectively move relative to the cartridge body from a closed position to an opened position, wherein the cage in the closed position is configured to contain the needle within the cartridge body, and wherein the cage in the opened position is received within the elongate slot and configured to allow removal of the needle from the cartridge body.

19. The surgical instrument of claim 18, wherein the cartridge receiving assembly includes a first jaw and a second jaw, wherein the first jaw is movable relative to the second jaw and collectively configured to receive the suture cartridge therebetween, wherein the cage securement includes an abutment extending from the first jaw toward the second jaw, wherein the abutment is configured to move away from the second jaw and toward the first jaw as the cage securement moves from the first position to the second position, and wherein the abutment is configured to inhibit movement of the cage of the suture cartridge from the closed position toward the opened position up to a predetermined opening force.

* * * * *